US012050151B2

(12) United States Patent
Geiger et al.

(10) Patent No.: US 12,050,151 B2
(45) Date of Patent: Jul. 30, 2024

(54) BURNER INCLUDING AN ELECTRICAL PERMITTIVITY OR ELECTRICAL CAPACITANCE FLAME SENSOR

(71) Applicant: ClearSign Technologies Corporation, Seattle, WA (US)

(72) Inventors: Robert Geiger, Seattle, WA (US); Jackson Matthew Pleis, Carnation, WA (US); Donald Kendrick, Bellevue, WA (US); Christopher A. Wiklof, Everett, WA (US)

(73) Assignee: ClearSign Technologies Corporation, Tulsa, OK (US)

( * ) Notice: Subject to any disclaimer, the term of this patent is extended or adjusted under 35 U.S.C. 154(b) by 577 days.

(21) Appl. No.: 17/135,884

(22) Filed: Dec. 28, 2020

(65) Prior Publication Data

US 2021/0254826 A1    Aug. 19, 2021

Related U.S. Application Data

(63) Continuation-in-part of application No. PCT/US2019/039475, filed on Jun. 27, 2019, and a
(Continued)

(51) Int. Cl.
*F23N 1/02* (2006.01)
*F23D 11/40* (2006.01)
(Continued)

(52) U.S. Cl.
CPC ........... *G01M 15/14* (2013.01); *F23D 11/406* (2013.01); *F23D 14/145* (2013.01); *F23N 1/022* (2013.01);
(Continued)

(58) Field of Classification Search
None
See application file for complete search history.

(56) References Cited

U.S. PATENT DOCUMENTS 4,882,573 A * 11/1989 Leonard ................ G08B 17/12
340/578
5,439,374 A    8/1995 Jamieson
(Continued)

FOREIGN PATENT DOCUMENTS

EP    2591289 B1    11/2016
WO    2015123683 A1    8/2015
(Continued)

OTHER PUBLICATIONS

Oyvind Isaksen "A review of reconstruction techniques for capacitance tomography" Meas. Sci. Technol. 7 (1996) 325-337.
(Continued)

*Primary Examiner* — Jason Lau
(74) *Attorney, Agent, or Firm* — Christopher A. Wiklof; James C. Larsen; Launchpad IP

(57) ABSTRACT

A burner includes a flame sensor configured to detect at least one of permittivity, capacitance, or resistance across a flame region. The permittivity, capacitance, or resistance is used to determine the presence or absence of the flame in a combustion system. A combustion system supports a combustion reaction. The combustion system utilizes a combustion sensor, and optionally a plasma generator to stabilize the combustion reaction. A controller receives sensor signals from the combustion sensor and controls the plasma generator to stabilize the combustion reaction responsive to the sensor signals. The plasma generator stabilizes the combustion reaction by generating a plasma.

19 Claims, 31 Drawing Sheets

Related U.S. Application Data continuation-in-part of application No. PCT/US2019/039461, filed on Jun. 27, 2019.

(60) Provisional application No. 62/821,543, filed on Mar. 21, 2019, provisional application No. 62/756,468, filed on Nov. 6, 2018, provisional application No. 62/702,475, filed on Jul. 24, 2018, provisional application No. 62/694,890, filed on Jul. 6, 2018, provisional application No. 62/691,469, filed on Jun. 28, 2018.

(51) Int. Cl.
| | |
|---|---|
| *F23D 14/14* | (2006.01) |
| *F23N 5/02* | (2006.01) |
| *F23N 5/12* | (2006.01) |
| *F23N 5/18* | (2006.01) |
| *G01M 15/14* | (2006.01) |
| *G01N 33/00* | (2006.01) |

(52) U.S. Cl.
CPC ............ *F23N 5/022* (2013.01); *F23N 5/123* (2013.01); *F23N 5/184* (2013.01); *G01N 33/0027* (2013.01); *G01N 33/0062* (2013.01); *G01N 33/0073* (2013.01); *F23D 2208/10* (2013.01); *F23D 2212/103* (2013.01); *F23N 2237/26* (2020.01)

(56) References Cited

U.S. PATENT DOCUMENTS

| | | | |
|---|---|---|---|
| 6,429,020 | B1 | 8/2002 | Thornton et al. |
| 6,887,069 | B1 | 5/2005 | Thornton et al. |
| 7,096,722 | B2 | 8/2006 | Benson et al. |
| 7,492,269 | B2 | 2/2009 | Matteson et al. |
| 7,559,234 | B1 | 7/2009 | Chorpening et al. |
| 7,927,095 | B1 * | 4/2011 | Chorpening ............ F23N 1/022 700/274 |
| 2003/0184320 | A1 * | 10/2003 | Breen .................. G01N 27/041 324/691 |
| 2005/0250061 | A1 | 11/2005 | Lochschmied |
| 2013/0086949 | A1 * | 4/2013 | Charbonneau .......... F23D 14/78 65/134.4 |
| 2013/0139578 | A1 | 6/2013 | Hoehne et al. |
| 2014/0045128 | A1 | 2/2014 | Lee et al. |
| 2014/0248566 | A1 | 9/2014 | Krichtafovitch et al. |
| 2015/0141240 | A1 | 5/2015 | Roller et al. |
| 2015/0204239 | A1 | 7/2015 | Minto et al. |
| 2015/0226133 | A1 | 8/2015 | Minto et al. |
| 2016/0298836 | A1 | 10/2016 | Colannino et al. |
| 2018/0003083 | A1 | 1/2018 | Huntington et al. |
| 2018/0003378 | A1 | 1/2018 | Karkow et al. |
| 2019/0107287 | A1 * | 4/2019 | Kitabayashi ............ F24C 3/085 |
| 2019/0203933 | A1 * | 7/2019 | Khan ....................... F23G 7/08 |

FOREIGN PATENT DOCUMENTS

| | | |
|---|---|---|
| WO | 2015123701 A1 | 8/2015 |
| WO | 2016040681 A1 | 3/2016 |

OTHER PUBLICATIONS

He, et al. "Engine flame imaging using electrical capacitance tomography" Electronics Letters, Mar. 31, 2994, vol. 30, No. 7, pp. 559-560.

Waterfall, et al. "Flame vizualizations using electrical capacitance tomography (ECTO)" Proc. SPIE vol. 4188, pp. 242-250.

NETL "CCADS: Combustion Control and Diagnostics Sensor for Advanced Gas Turbines" Jun. 2008.

PCT International Search Report and Written Opinion for International Application No. PCT/US2019/039467 dated Oct. 21, 2019 16 pgs.

PCT International Preliminary Report and Written Opinion for International Application No. PCT/US2019/039467 dated Dec. 29, 2020, 11 pgs.

PCT International Search Report and Written Opinion for International Application No. PCT/US2019/039461 dated Oct. 21, 2019, 16 pgs.

PCT International Preliminary Report and Written Opinion for International Application No. PCT/US2019/039461 dated Dec. 29, 2020, 11 pgs.

PCT International Preliminary Report on Patentability for International Application No. PCT/US2019/039461 dated Dec. 29, 2020, 11 pgs.

* cited by examiner

BURNER INCLUDING AN ELECTRICAL PERMITTIVITY OR ELECTRICAL CAPACITANCE FLAME SENSOR

CROSS REFERENCE TO RELATED APPLICATIONS

The present application is a Continuation-in-Part Application that claims priority benefit from PCT Application No. PCT/US2019/039461, entitled "BURNER INCLUDING AN ELECTRICAL PERMITTIVITY OR ELECTRICAL CAPACITANCE FLAME SENSOR", filed Jun. 27, 2019 and PCT Application No. PCT/US2019/039475, entitled "COMBUSTION SYSTEM INCLUDING A COMBUSTION SENSOR AND A PLASMA GENERATOR", filed Jun. 27, 2019. PCT Applications No. PCT/US2019/039461 and PCT/US2019/039475, both claim priority benefit from U.S. Provisional Patent Application No. 62/756,468, entitled "PILOT BURNER WITH A FLAME SENSOR," filed Nov. 6, 2018, from U.S. Provisional Patent Application No. 62/821,543, entitled "COMBUSTION SYSTEM INCLUDING A COMBUSTION SENSOR AND A PLASMA GENERATOR," filed Mar. 21, 2019, from U.S. Provisional Patent Application No. 62/694,890, entitled "INDUSTRIAL BURNER INCLUDING A LOW TEMPERATURE PLASMA STABILIZED FLAME HOLDER," filed Jul. 6, 2018, from U.S. Provisional Patent Application No. 62/691,469, entitled "BURNER SYSTEM INCLUDING A PERFORATED FLAME HOLDER AND ELECTRO-CAPACITIVE SENSING," filed Jun. 28, 2018, and from U.S. Provisional Patent Application No. 62/702,475, entitled "VARIABLE COMPOSITION GAS MIXTURE SENSOR," filed Jul. 24, 2018. Each of the foregoing applications, to the extent not inconsistent with the disclosure herein, is incorporated by reference in its entirety.

The present application is related to U.S. Patent Application No. [TBD], entitled, "VARIABLE COMPOSITION GAS MIXTURE SENSOR," filed contemporaneously herewith.

SUMMARY OF THE DISCLOSURE

According to an embodiment, a burner includes a fuel source, an oxidant source, and a plenum wall defining an air plenum, the air plenum configured to receive fuel and oxidant respectively from the fuel source and the oxidant source, the air plenum further configured to convey the fuel and the oxidant to facilitate mixture of the fuel and the oxidant into a fuel-oxidant mixture. The burner can be a pilot burner. An ignition source may be disposed at a distal portion of the air plenum and oriented to ignite the fuel-oxidant mixture to produce a flame in a flame region. At least a first electrode and a second electrode are arranged adjacent to the flame region and configured to produce a time-varying electromagnetic field across the flame region. A change in electrical permittivity or electrical capacitance in the flame region is determined from the time-varying electromagnetic field. Whether the system measures electrical permittivity, electrical capacitance, or electrical resistance, etc. is substantially determined by detector circuitry. In practice, the presence of a flame affects substantially all such related electrical characteristics according to its position in an R/C detector circuit. For ease of understanding, one or another single characteristic may be described herein and is to be understood to have corresponding meaning to other characteristics, combinations of characteristics, inversions of characteristics, etc. Presence or absence of the flame may be determined from the electrical permittivity, capacitance, resistance, etc.

According to an embodiment, a combustion system includes a burner having at least a first electrode and a second electrode arranged adjacent to a flame region and configured to produce a time-varying electromagnetic field across the flame region and a controller configured to drive a signal across the first and the second electrodes and receive a detection signal indicative of presence or absence of a flame in the flame region. According to embodiments, a perforated reaction holder may be disposed a distance from the burner and oriented to receive a main fuel-oxidant mixture. The burner may be configured to preheat the perforated reaction holder.

According to an embodiment, a method includes receiving, in an air plenum, fuel and oxidant, and forming a fuel-oxidant mixture by conveying the fuel and the oxidant in the air plenum. The method includes producing a flame in a flame region by igniting the fuel-oxidant mixture with an ignition source disposed at an extent of the plenum, and producing a time-varying electromagnetic field across the flame region with a first and a second electrode arranged adjacent to the flame region. The method includes determining a change in electrical permittivity in the flame region based on the time-varying electromagnetic field, and controlling the flame based on the change in electrical permittivity.

In one embodiment, a combustion system includes a fuel and oxidant source configured to output fuel and oxidant into a furnace volume, a combustion sensor configured to sense a combustion reaction of the fuel and oxidant within the furnace volume, and a plasma generator positioned at least partially within the furnace volume and configured to stabilize the combustion reaction by generating a plasma. The combustion system includes a controller operatively coupled to the combustion sensor and the plasma generator, the controller being configured to receive sensor signals from the combustion sensor indicative of a condition of the combustion reaction and to control operation of the plasma generator responsive to the sensor signals. Various combustion sensors are contemplated, including combustion sensors positioned at least partially within the furnace volume and at least one combustion sensor that may be positioned outside the furnace volume.

In one embodiment, a combustion system includes a fuel and oxidant source configured to output fuel and oxidant into a furnace volume and a flame holder positioned within the furnace volume and aligned to receive the fuel and the oxidant. The flame holder is configured to hold a combustion reaction of the fuel and the oxidant. The combustion system includes a combustion sensor including one or more sensor electrodes positioned adjacent to the flame holder (e.g., within or outside of furnace volume walls) and configured to sense the combustion reaction at the flame holder. The combustion system may include a plasma generator positioned at least partially within the furnace volume and configured to stabilize the combustion reaction at the flame holder by outputting a plasma in a vicinity of the flame holder. The plasma generator may be operable to generate a low temperature plasma (e.g., a plasma formed as atomic or molecular radicals) and/or a high temperature plasma (e.g., a plasma formed as ions and electrons). The combustion system includes a controller operatively coupled to the combustion sensor and the plasma generator, configured to receive sensor signals from the combustion sensor indicative of a condition of the combustion reaction and to control operation of the plasma generator responsive to the sensor signals. For example, the controller may be configured to drive the plasma generator to output a low temperature plasma if and when the sensor signals indicate a stable combustion reaction or a combustion reaction with relatively minor oscillations in location and/or temperature. The controller may be configured to drive the plasma generator to output a high temperature plasma if and when the sensor signals indicate absence of combustion in the vicinity of the flame holder and/or relatively unstable combustion.

In one embodiment, a combustion system includes a fuel and oxidant source configured to output a swirling mixture of fuel and oxidant within a furnace volume. The combustion system includes an electro-capacitive (or, equivalently, electro-permittivity) combustion sensor including one or more sensor electrodes positioned adjacent to or within the furnace volume and configured to sense a combustion reaction of the fuel and the oxidant at a sensed combustion location. The combustion system includes a plasma generator positioned at least partially within the furnace volume and configured to stabilize the combustion reaction location by outputting a plasma including activated reaction-initiating atomic, electron, and/or molecular moieties. (E.g., the activated moieties may include radicals or electrons and ions, depending on plasma temperature.) The combustion system includes a controller operatively coupled to the electro-capacitive combustion sensor and the plasma generator, the controller being configured to receive sensor signals from the electro-capacitive combustion sensor indicative of a condition of the combustion reaction and to control operation of the plasma generator to generate a low temperature plasma and/or to generate a high temperature plasma responsive to the sensor signals.

In one embodiment, a method includes outputting fuel and oxidant into a furnace volume and sensing, with a combustion sensor, a combustion reaction of the fuel and the oxidant within the furnace volume. The method includes outputting, with the combustion sensor, sensor signals indicative of a characteristic of the combustion reaction. The method includes receiving, with a controller, sensor signals from the combustion sensor stabilizing the combustion reaction responsive to the sensor signals by controlling, with the controller, a plasma generator to generate a plasma in a vicinity of the selected combustion location.

According to an embodiment, a burner system includes a perforated flame holder disposed within a furnace volume defined by furnace walls. The perforated flame holder is supported by a support structure. The burner system includes a fuel and oxidant source aligned to supply a fuel and oxidant mixture to the perforated flame holder. The burner system includes a power source having first and second output terminals and first and second plasma generation electrodes respectively operatively coupled to the first and the second output terminals. At least one of the first and the second plasma generation electrodes is disposed adjacent to or within the perforated flame holder. The power source and the first and the second plasma generation electrodes are operable to cause a plasma to form within or adjacent to the perforated flame holder. For example, the power source may be an AC, DC, or pulsed power source and the plasma generation electrodes may include one or more corona electrodes and/or one or more dielectric barrier electrodes.

According to an embodiment, a method for improving flame stability in a burner includes delivering a fuel and oxidant mixture to a perforated flame holder, supporting a combustion reaction with the fuel and oxidant mixture in the perforated flame holder, forming a low temperature plasma in or adjacent to the perforated flame holder; and producing plasma enhanced ignition of the combustion reaction.

According to an embodiment, a burner system includes a main fuel source configured to output a fuel stream and an oxidant source configured to output an oxidant to mix with the fuel stream. The burner system includes a perforated flame holder aligned to receive a mixture of the fuel and the oxidant. The perforated flame holder is configured to hold a flame supported by the fuel and the oxidant. The burner system includes a flame sensor having a first sensor electrode, a second sensor electrode, and a sensor controller respectively coupled to the first and the second sensor electrodes via first and second electrical leads. The first and the second sensor electrodes are aligned such that a straight line or a fringing field between centers of the first and the second sensor electrodes passes through the perforated flame holder. The first and the second sensor electrodes and the sensor controller are configured to cooperate to measure a combustion reaction characteristic including the presence or absence of the flame held by the perforated flame holder.

According to an embodiment, a method for flame sensing in a perforated flame holder includes supporting first and second sensor electrodes adjacent to and in opposition across a perforated flame holder, and applying a time varying voltage to the first sensor electrode to produce a broadcast signal that propagates through the perforated flame holder. The broadcast signal may include, for example, a sinusoid having a carrier frequency at 10 to 100 kilohertz with a power generated by a 15 volt peak-to-peak driver signal in continuity with the first sensor electrode. The method includes receiving the broadcast signal with the second sensor electrode. The broadcast signal is modified according to the presence or absence of a flame in the perforated flame holder. The method includes converting the received signal into a digital received signal, analyzing the digital received signal with a signal analyzer to determine a state of a flame in the perforated flame holder, and outputting digital data corresponding to the state of the flame. The state of the flame can include presence, absence, or intermediate completeness of combustion.

According to an embodiment, a burner system includes a main fuel source configured to output a fuel stream and an oxidant source configured to output an oxidant to mix with the fuel stream. The burner system includes a perforated flame holder aligned to receive a mixture of the fuel and the oxidant. The perforated flame holder is configured to hold a flame supported by the fuel and the oxidant. The burner system includes a flame sensor having a first sensor electrode, a second sensor electrode, and a sensor controller respectively coupled to the first and the second sensor electrodes via first and second electrical leads. The first and the second sensor electrodes are aligned such that a signal from the first sensor electrode passes through a flame supported by the flame holder. The flame holder can be a perforated flame holder and the flame may be supported substantially within the perforated flame holder. The first and the second sensor electrodes and the sensor controller are configured to cooperate to measure the presence or absence of the flame held by the flame holder.

According to an embodiment, a burner system includes a perforated flame holder disposed within a furnace volume defined by furnace walls. The perforated flame holder is supported by a support structure. The burner system includes a fuel and oxidant source aligned to supply a fuel and oxidant mixture to the perforated flame holder. The burner system includes a power source having first and second output terminals and first and second plasma generation electrodes, respectively operatively coupled to the first and the second output terminals. At least one of the first and the second plasma generation electrodes is disposed adjacent to or within the perforated flame holder. The power source and the first and the second plasma generation electrodes are operable to cause a plasma to form within or adjacent to the perforated flame holder.

According to an embodiment, a burner system includes a fuel and oxidant source configured to support a combustion reaction by supplying a fuel and an oxidant into a furnace volume. The burner system includes a plasma generator including a power source having first and second output terminals and first and second plasma generation electrodes, respectively operatively coupled to the first and the second output terminals. At least one of the first and the second plasma generation electrodes is disposed in the combustion volume. The power source and the first and the second plasma generation electrodes are operable to cause a plasma to form within the combustion volume whereby the plasma is operable to enhance ignition of the combustion reaction within the combustion volume.

According to an embodiment, a burner system includes a main fuel source configured to output a fuel stream and an oxidant source configured to output an oxidant to mix with the fuel stream. The burner system includes a flame sensor. The flame sensor includes a first sensor electrode, a second sensor electrode, and a sensor controller respectively coupled to the first and the second sensor electrodes via first and second electrical leads. The first and the second sensor electrodes and the sensor controller are configured to cooperate to measure the presence or absence of a flame supported by a mixture of the fuel stream and the oxidant.

DETAILED DESCRIPTION

Figure 1:
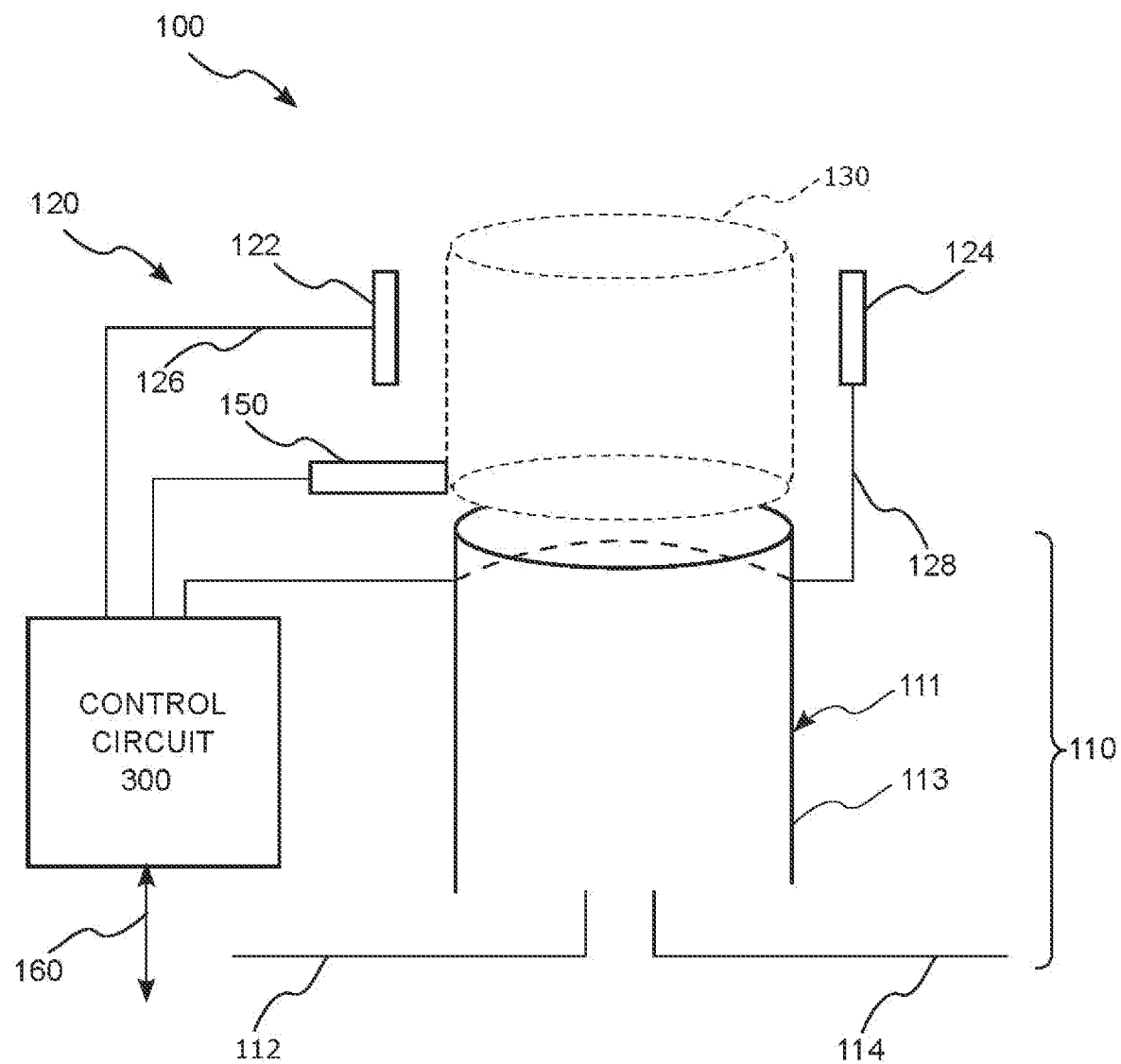
FIG. 1 is a block diagram of a burner having an integral electronic flame sensor, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

Reliable flame detection is a common challenge in many industrial burner applications. For example, detecting the presence of a flame may facilitate fuel shut-off, initiate a restart process, or the like. In other applications, detecting the presence of a flame in a particular region may facilitate modification of the flame to predetermined levels. Conventional methods of flame detection suffer from various shortcomings that are addressed by the present disclosure.

The apparatus and method(s) disclosed herein utilize electrodes disposed near but outside of a flame. The electrodes may detect small changes in electrical permittivity across a region where the flame is expected. These changes may be monitored to detect the presence or absence of flame and in some instances may detect qualities of a flame. The disclosed structures and methods of the present disclosure may not require an optical window, may not necessarily reside in or affect the flame, and may enjoy faster response time compared with conventional flame detection techniques. According to embodiments, the disclosed flame detection apparatus and method(s) measure changes in an electrical characteristic (e.g., permittivity, resistance, and/or capacitance) across the flame space (e.g., flame region) adjacent to the electrodes.

The device may measure permittivity across the flame space by broadcasting an excitation signal from one electrode and measuring the signal received at a second electrode. The magnitude of the received signal is directly proportional to the permittivity of the medium therebetween, and may therefore differentiate between air, or an uncombusted mixture of air and fuel, and the ionized region of a flame.

As used herein, the terms perforated flame holder, perforated reaction holder, porous flame holder, porous reaction holder, duplex, and duplex tile shall be considered synonymous unless context indicated otherwise.

FIG. 1 is a block diagram showing features of a burner 100 having an electronic flame sensor referred to herein as a flame sensor 120, according to embodiments. The burner 100 includes a fuel and oxidant source 110 including a fuel source 112, an oxidant (e.g., air) source 114, and an air plenum 111 defined by a plenum wall 113. The air plenum 111 may be configured to receive the fuel and the oxidant respectively from the fuel source 112 and the oxidant source 114. The air plenum 111 further may be configured to convey the fuel and the oxidant to facilitate mixture of the fuel and the oxidant into a fuel-oxidant mixture. According to an embodiment, the burner 100 includes an ignition source 150 disposed at a distal portion of the air plenum 111 and oriented to ignite the fuel-oxidant mixture to produce a flame in a flame region 130.

The flame sensor 120 may include at least a first electrode 122, a second electrode 124, and a control circuit 300. The first electrode 122 and the second electrode 124 may be disposed adjacent to the flame region 130 and configured to produce a time-varying electromagnetic field across the flame region 130. A change in electrical permittivity or electrical capacitance in the flame region 130 is determined from the time-varying electromagnetic field.

According to an embodiment, the burner 100 is a pilot burner. The pilot burner 100 can be configured to support a pilot flame.

According to an embodiment, at least the first electrode 122 and the second electrode 124 are disposed opposite each other across the flame region 130. The first electrode 122 may be configured to broadcast an excitation signal to produce the time-varying electromagnetic field between the first and the second electrodes 122, 124. The second electrode 124 may be configured to receive a detection signal, the detection signal including the broadcast excitation signal as affected by the change in electrical permittivity between the first and the second electrodes 122, 124. According to an embodiment, the first and the second electrodes 122, 124 are patch electrodes.

According to another embodiment, at least the first or the second electrode 122, 124 may be disposed on a fuel riser (not shown) that passes through at least a portion of the air plenum 111. A tip of the fuel riser 454, including a fuel nozzle, may be seen in FIG. 4, according to an embodiment. The other of at least the first or the second electrode 122, 124 may be disposed peripheral to a distal end of the air plenum 111 (e.g., see 422, 424 of FIG. 4).

According to an embodiment, the control circuit 300 is configured to generate the excitation signal and provide the excitation signal to the first electrode 122. The control circuit 300, described in greater detail below, may be further configured to receive the detection signal from the second electrode 124 and to determine a magnitude of the electrical permittivity of the flame region 130 by measuring or calculating a signal characteristic from the detection signal.

According to an embodiment, the control circuit 300 may be further configured to identify a flame characteristic by comparing the determined magnitude of the electrical permittivity against an index of flame characteristics corresponding to respective electrical permittivity magnitudes. The control circuit 300 may be further configured to alter a supply rate of the fuel supplied by the fuel source 112 based on the identified characteristic of the flame.

According to an embodiment, the identified characteristic of the flame is a presence or absence of the flame as determined by comparison of the magnitude of the electrical permittivity with a threshold electrical permittivity, and the control circuit 300 terminates the supply of fuel when the flame is indicated to be absent. The control circuit 300 may further include circuitry configured to drive the ignition source 150 responsive to the identified characteristic of the flame.

Additionally or alternatively, the identified characteristic of the flame is a presence or absence of the flame as determined by comparison of the magnitude of the electrical permittivity with a threshold electrical permittivity, and the control circuit 300 drives the ignition source 150 when the flame is indicated to be absent.

According to an embodiment, the control circuit 300 is further configured to compare the detection signal to a threshold detection signal, and to produce a binary result signal indicating presence or absence of the flame.

According to an embodiment, the control circuit 300 is configured to produce an output signal indicating a strength of the flame between the first and the second electrodes 122, 124. The output signal can be an analog signal between 4 mA and 20 mA. The analog signal can correspond to a strength of combustion activity between the first and the second electrodes 122, 124.

According to an embodiment, the control circuit 300 may be configured to adjust characteristics of the excitation signal, including at least one of magnitude, duty cycle, pulse width, wave shape, and frequency delivered to the first electrode 122. According to an embodiment, the excitation signal is a time-varying electrical voltage. The excitation signal may be a sinusoidal electromagnetic wave generated, e.g., by direct digital synthesis, or may be another wave shape such as a square wave or pulse, and the excitation signal's broadcast by the first electrode 122 may result in an electromagnetic field across the flame region 130. According to an embodiment, the excitation signal may be generated periodically.

According to an embodiment, the control circuit 300 may further control a rate of supply of the fuel source 112 and the oxidant source 114. Control of the fuel and the oxidant sources 112, 114 may be implemented as independent controls with a plurality of rates, or maybe implemented as a master shutoff or turn-on control, e.g., in cases where rate is more finely controlled manually or by other means. In some embodiments, the control circuit 300 may include circuitry for communication to and/or from other sensors, actuators, circuitry or the like via one or more conductors or wireless transmission 160 (see, e.g., mention of I/O, input conductor(s) 260, and output conductor(s) 262 below with respect to FIG. 2).

According to an embodiment, the burner 100 may further include a first conductor 126 in electrical continuity between the first electrode 122 and the control circuit 300, and at least partly disposed peripherally to the plenum defining the air plenum 111, and a second conductor 128 in electrical continuity between the second electrode 124 and the control circuit 300, and at least partly disposed peripherally to the plenum defining the air plenum. The first and the second conductors 126, 128 may be at least partly disposed peripherally to the plenum defining the air plenum 111. The first or the second electrode 122, 124 may be in electrical continuity with a conductive tubular structure (e.g., a fuel riser) disposed axially within the air plenum 111. Additionally or alternatively, the first or the second electrode 122, 124 may be in electrical continuity with the conductive tubular structure disposed peripherally to the air plenum 111. According to an embodiment, the burner 100 with the flame sensor 120 may be incorporated in a combustion system such as, but not limited to that described below in relation to FIG. 2.

Figure 2:
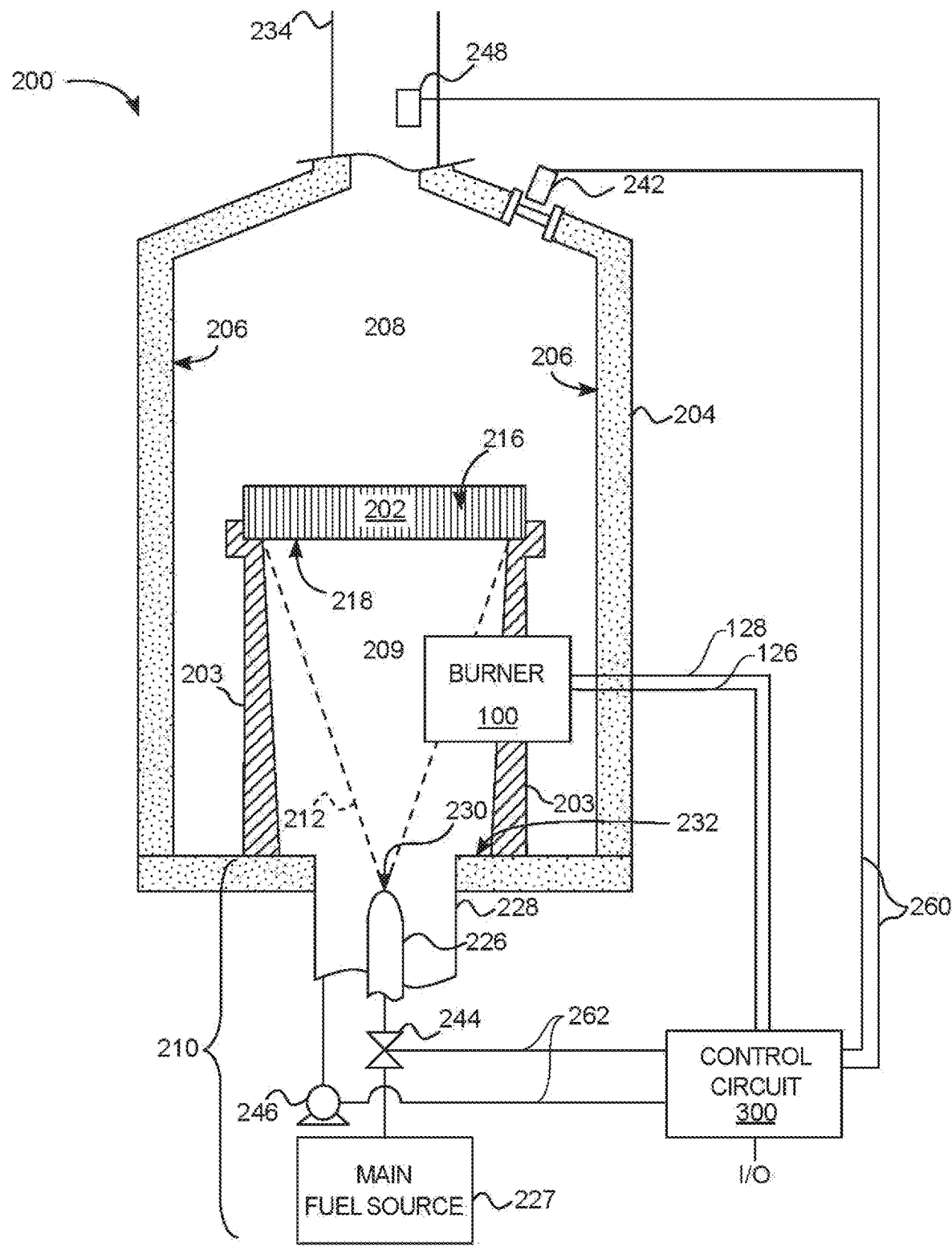
FIG. 2 is a diagrammatic depiction of a combustion system, according to an embodiment.

FIG. 2 is a diagrammatic depiction of a combustion system 200, according to an embodiment. The combustion system 200 includes a plenum defining a combustion volume 208, a burner 100 (such as the burner 100 described above), and a perforated reaction holder support structure 203 disposed within the combustion volume 208. The combustion system 200 includes a perforated reaction holder 202 supported by the perforated reaction holder support structure 203 and disposed a distance from the burner 100.

The combustion volume 208 may be defined by one or more furnace walls 206. The furnace wall 206 may include a combustion volume floor 232. The combustion volume 208 may include a mixing region 209 between a perforated reaction holder 202 and the combustion volume floor 232 (or in some instances a furnace wall 206). The burner 100 may be at least partly disposed in the mixing region 209 of the combustion volume 208.

The combustion system 200 may further include a main fuel and oxidant source 210 configured to provide and direct a main fuel and a main oxidant (e.g., air) toward the perforated reaction holder 202 into the mixing region 209 such that the main fuel and the main oxidant become mixed into a main fuel and oxidant mixture 212 as the main fuel and the main oxidant traverse a distance between the main fuel and oxidant source 210 and the perforated reaction holder 202. The mixing region 209 may be configured to facilitate mixture of the main fuel and the main oxidant into the main fuel-oxidant mixture 212. The main fuel and oxidant source 210 may include a main fuel source 227, a fuel nozzle 226, and a main fuel reservoir (not numbered separately), configured to provide and direct the main fuel toward the perforated reaction holder 202. A fuel valve 244 may control supply of the main fuel to the fuel nozzle 226. The main fuel and oxidant source 210 may further include a main oxidant source 228 or conduit configured to output and direct the main oxidant, e.g., via a blower 246, toward the perforated reaction holder 202. The fuel nozzle 226 may be configured to emit the main fuel through a fuel orifice 230.

According to an embodiment, the perforated reaction holder support structure 203 may be configured to support the perforated reaction holder 202 at the distance from the main fuel and oxidant source 210. FIG. 2 depicts the perforated reaction holder support structure 203 as supporting the perforated reaction holder 202 from the combustion volume floor 232. However, it will be recognized that the perforated reaction holder support structure 203 may alternatively support the perforated reaction holder 202 from another portion or portions of a furnace body 204.

According to an embodiment, a burner, such as the burner 100 described above with respect to FIG. 1 including a flame sensor 120, may be disposed upstream of the perforated reaction holder 202. The burner 100 is configured and arranged to preheat the perforated reaction holder 202, and may be configured to provide a flame at least during a start-up of the combustion system 200. In some embodiments, the burner 100 may be configured to provide the flame perpetually during operation of the combustion system 200. In some embodiments, the burner 100 may be mounted to or otherwise disposed at the perforated reaction holder support structure 203, similar to the illustration in FIG. 2. In other embodiments, the burner 100 may be disposed at another location upstream from the perforated reaction holder 202, such as at the combustion volume floor 232 that is defined by the furnace body 204. The burner 100 may be configured to cause heating of the perforated reaction holder 202. The perforated reaction holder 202 may be configured to support a combustion reaction of the main fuel and oxidant mixture 212 substantially within perforations 216 of the perforated flame holder 202 after the burner 100 preheats the perforated reaction holder 202.

The combustion system 200 may further include a control circuit 300 operatively coupled to the burner 100 and other elements of the combustion system 200. The control circuit 300 may incorporate the features described with respect to the control circuit 300 of FIG. 1 (which is described in greater detail below with respect to FIG. 3). That is, the control circuit 300 may be configured to include an excitation signal source (see element 320 in FIG. 3) configured to generate an excitation signal and provide the excitation signal to the first electrode 122, detection circuitry (see element 330 in FIG. 3) configured to receive a detection signal from the second electrode 124, and an output electrically connected to at least one of the fuel source 112 and the oxidant source 114 and configured to control a supply rate of at least one of the fuel and the oxidant.

According to an embodiment, the combustion system 200 may further include at least one sensor disposed at least partially within the combustion volume 208 and electrically connected to the control circuit 300. For example, the control circuit 300 may be configured to respond to input received via input conductor(s) 260 (or in some embodiments via a wireless signal) electrically connected to a heat sensor 242 and/or an oxygen sensor 248 disposed at the furnace wall 206.

The control circuit 300 may include one or more outputs 262 for electrical connection with burner controls such as the main fuel valve 244 and blower 246 to control at least one of a main fuel supply rate and/or a main oxidant supply rate, a position of the fuel nozzle 226, an orientation of the fuel nozzle 226, and a distance between the perforated reaction holder 202 and the main fuel source. In some embodiments, this control may be responsive to a signal from the at least one sensor (e.g., the sensor inputs noted above).

In one embodiment, the burner 100 acts as a pilot burner that supports a pilot flame. The pilot flame can support combustion of a main fuel and oxidant at the perforated flame holder 202.

In one embodiment, the burner 100 is not positioned as shown in FIG. 2, but rather burner 100 includes the main fuel nozzle 226 and supports the combustion reaction within the perforated flame holder 202. The first and the second electrodes 122 and 124 can be positioned adjacent to or on opposite sides of the perforated flame holder 202. The first and the second electrodes 122 and 124 can cooperate with the control circuit 300 to detect the presence of a flame within perforated flame holder 202. The control circuit 300 can control one or more of the ignition source 150 and the output of the main fuel and oxidant responsive to conditions sensed by the first and the second electrodes 122, 124.

Figure 3:
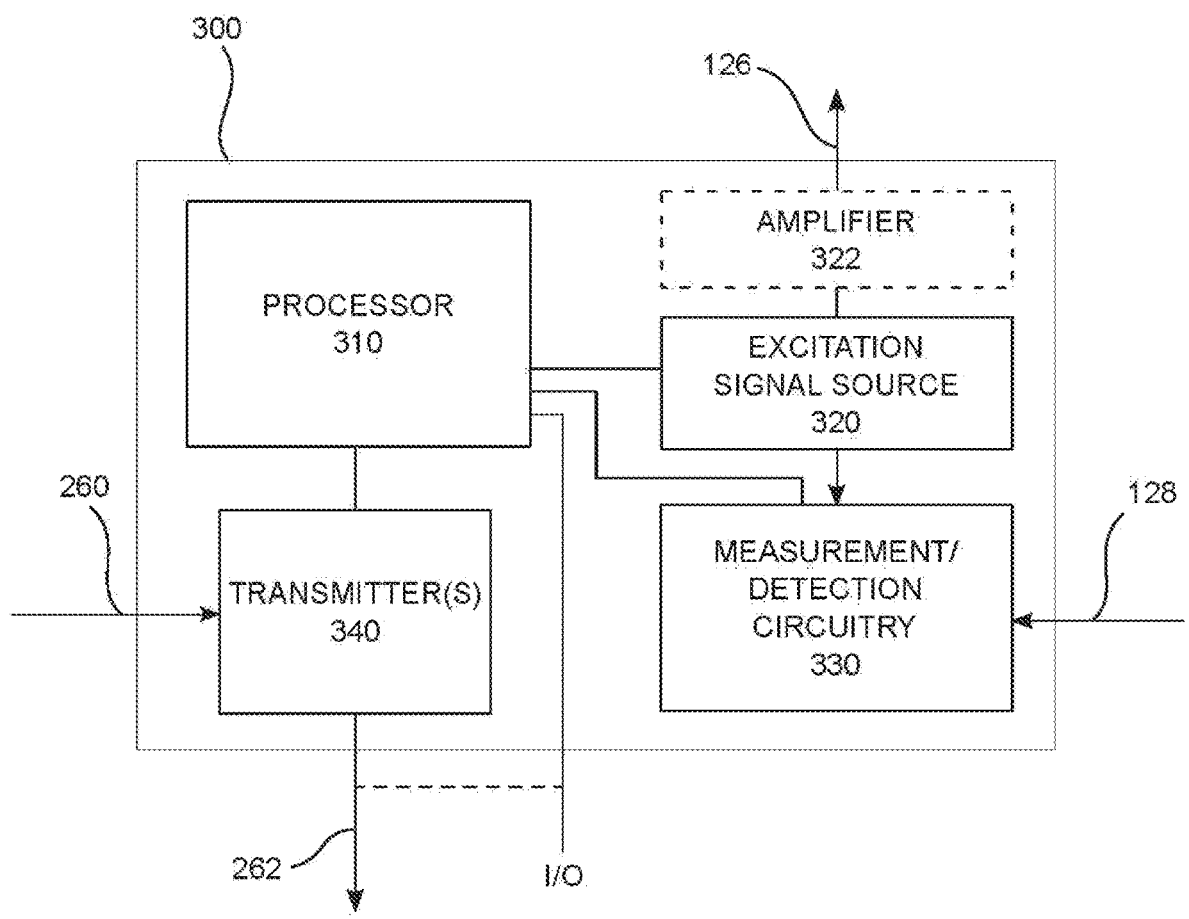
FIG. 3 is a block diagram illustrating elements of a control circuit of the burner of FIG. 1, according to an embodiment.

FIG. 3 is a block diagram illustrating the control circuit 300 of the burner 100, according to an embodiment. The control circuit 300 may include at least one processor 310, an excitation signal source 320, and measurement and/or detection circuitry 330. In some embodiments, the control circuit 300 may also include one or more transmitters 340. The transmitter(s) 340 may be electrically connected to the fuel valve 244 and/or blower 246 to control the supply of main fuel and main oxidant. The processor 310 may be a microcontroller, microprocessor, signal processor, ASIC, PLD, or the like, configured to receive data from other elements of the control circuit 300 and/or from external sources, process the data and transmit data to the other elements of the control circuit 300 and/or external destinations. Specifically, the processor 310 may be disposed in electrical communication with the excitation signal source 320, the measurement and/or detection circuitry 330 and the transmitter 340, along with various discrete components and, in some embodiments, a non-transient computer readable medium such a read-only memory (ROM), random access memory (RAM) or variants thereof, such as an electrically-erasable programmable read only memory (EE-PROM).

The processor 310 may further communicate, e.g., via transmitter(s) 340 with sensors or actuators corresponding to other features of a system in which the burner 100 may be employed. For example, the burner 100 may be utilized in a combustion system such as the combustion system 200 shown in FIG. 2 and described above, or with sensors related to threshold burner temperatures, ambient conditions, manual switches, time-of-day- or season-based timers, shut-down controls, and/or the like, any of which may provide signals to the control circuit 300 for controlling operation of the burner 100. Likewise, the control circuit 300 may provide signals to circuitry and/or actuators distinct from the control circuit 300, to monitoring-screens or control-screens, sensors, or the like, e.g., for monitoring and/or controlling parameters or characteristics of the burner 100 and/or elements thereof, or for monitoring and/or controlling elements of other external systems such as described herein with respect to the combustion system 200 of FIG. 2.

The excitation signal source 320 may be a signal generator or other circuitry configured to selectively provide a time-varying excitation signal (e.g., a voltage) to the first electrode 122 via the first conductor 126. In some embodiments, the control circuit 300 may include an amplifier 322 configured to amplify the generated excitation signal provided to the first electrode 122 from the excitation signal source 320. The excitation signal source 320 may be configured to effect the aforementioned adjustment of characteristics of the excitation signal, including at least one of the characteristics including wave shape, magnitude, and frequency of the excitation signal, or to provide a non-time varying signal (e.g., direct current) to the first electrode 122.

According to an embodiment, the generated excitation signal is a square wave, and the excitation signal source 320 may be further configured to control at least one or more of pulse width, duty cycle, and modulation. The generated excitation signal's wave shape may be another shape, such as a sinusoid, sawtooth, triangle, or other shape. The excitation signal source 320 may generate the excitation signal according to known methods, such as by direct digital synthesis. The generated excitation signal's broadcast by the first electrode 122 may result in an electromagnetic field across the flame region 130. The processor 310 may be configured to control the configuration of the excitation signal source 320 in response to an input. For example, the excitation signal source 320 may be controlled responsive to a sensor input received by the processor 310, or in response to a calculated value reaching a predetermined range or value such as a value calculated or retrieved from memory by the processor 310, or in response to a human-entered command. For example, in some embodiments the processor 310 may receive a feedback signal from a combustion system (e.g., combustion system 200 of FIG. 2 described herein) indicating a temperature condition or other value at some portion of the combustion system. That feedback signal may be used in a calculation or as a direct comparison to a predetermined value, the result of such calculation or comparison causing the processor 310 to signal an actuator or the like to control a change in configuration of the combustion system 200, such as supply rate of the main fuel and/or main oxidant, speed or direction of a swirler, fuel dispersion characteristics or the like.

The measurement and/or detection circuitry 330 may be in electrical communication with the second electrode 124 via the second conductor 128 to receive a detection signal. In some embodiments, the first and second conductors 126, 128 may be partly replaced by wireless circuitry, such that control of the time varying signal and transmission of the detection signal may be communicated wirelessly between the control circuit 300 and circuitry, such as a signal amplifier (not shown), disposed remotely from the control circuit 300 at the burner 100.

The measurement and/or detection circuitry 330 may be configured to compare the detection signal against the excitation signal to determine a permittivity or capacitance of the flame region 130. According to an embodiment, the measurement and/or detection circuitry 330 may receive the excitation signal from the excitation signal source 320 and the detection signal and amplify a difference between the two signals. That difference reflects the electric field resistance (i.e., permittivity) of the medium between the first and second electrodes. The greater the differential, the greater is the permittivity of the medium. For purposes of this application, permittivity (also referred to as "distributed capacitance") is a measure of how an electric field is affected by a dielectric medium. It has been recognized that permittivity of air (as a dielectric medium) is different from permittivity of a flame (as another dielectric medium). Accordingly, when a flame is present in the flame region 130, the permittivity between the first and second electrodes 122, 124 is different from the permittivity when a flame is not present. Permittivity $\varepsilon$ of a medium in the flame region 130 is based on a capacitance C measured between the electrodes 122, 124, the area A of the electrode (e.g., second electrode 124), and the distance d between the two electrodes 122, 124 and is determined as follows:

$$\varepsilon = C\frac{d}{A}.$$

The control circuit 300 may compare the magnitude of measured permittivity to a threshold permittivity, or in some embodiments may simply monitor a significant change in the measured permittivity in order to detect the presence of a flame. For example, permittivity of the area between the first electrode 122 and the second electrode 124 may be calculated periodically and compared with a predetermined threshold permittivity value, or a range of such values. When the calculated permittivity exceeds the predetermined threshold permittivity value, or is outside the range of such values, the measurement and/or detection circuit 330 may provide a signal to the processor indicating a change in the presence or absence of the flame.

According to an alternative embodiment, the measurement and/or detection circuit 330 may compare the determined permittivity with an index of values corresponding to different flame characteristics. For example, the flame may have a different permittivity at different fuel supply rates, or when using different fuels, or at different flame temperatures. Accordingly, a characteristic of a flame may be determined from comparing a determined permittivity of the flame region 130 against a predetermined index of flame characteristics. Alternatively, the measurement and/or detection circuit 330 may merely report the determined permittivity of the flame region 130 to the processor 310, and the processor 310 may identify the flame characteristic via the determined permittivity. Each indexed flame characteristic may cause the processor 310 to perform a respective action according to a perceived need associated with the corresponding flame characteristic.

According to another embodiment, a change in the detection signal over time may be monitored to detect presence or absence or a flame. For example, a base value of the detection signal may be recorded at a predetermined state. When the detection signal is outside a predetermined range that includes that base value, the detection signal may be determined as indicating a change in the permittivity of the flame region 130, e.g., a change from presence of a flame to absence of the flame, or vice versa. In some instances, an average value of the detection signal over a predetermined period may be monitored. For example, a value of the detection signal may be periodically recorded and a plurality of the recorded values may be averaged. This can mitigate variances in the flame's position or composition that in some circumstances would otherwise cause the measurement and/or detection circuit 330 or the processor 310 to incorrectly perceive changes in flame presence, which could lead to, e.g., untimely fuel shut-off based on an instantaneous value of the detection signal.

In instances where area of the electrodes and distance between the electrodes is static, the control circuit 300 determines capacitance between the first and second electrodes 122, 124 in order to determine the magnitude of the permittivity. Characteristics of the excitation signal are intentionally generated, and therefore known. Thus, a change in a characteristic of the detection signal compared with the excitation signal indicates a change in permittivity. Capacitance can be determined in several conventional ways, each of which is contemplated by the inventors. For example, capacitance can be calculated from the time (e.g., rise time) the detection signal takes to reach a particular voltage (magnitude).

According to an embodiment, therefore, the permittivity of the flame region 130 without a flame will be measurably different from the permittivity of the flame region 130 when a flame is present.

The control circuit 300 may be implemented on a circuit board disposed a distance from the burner 100. For example, the control circuit 300 may be disposed outside the combustion volume 208, such as at a distal end of the burner 100, and/or distal from the flame region 130.

Figure 4:
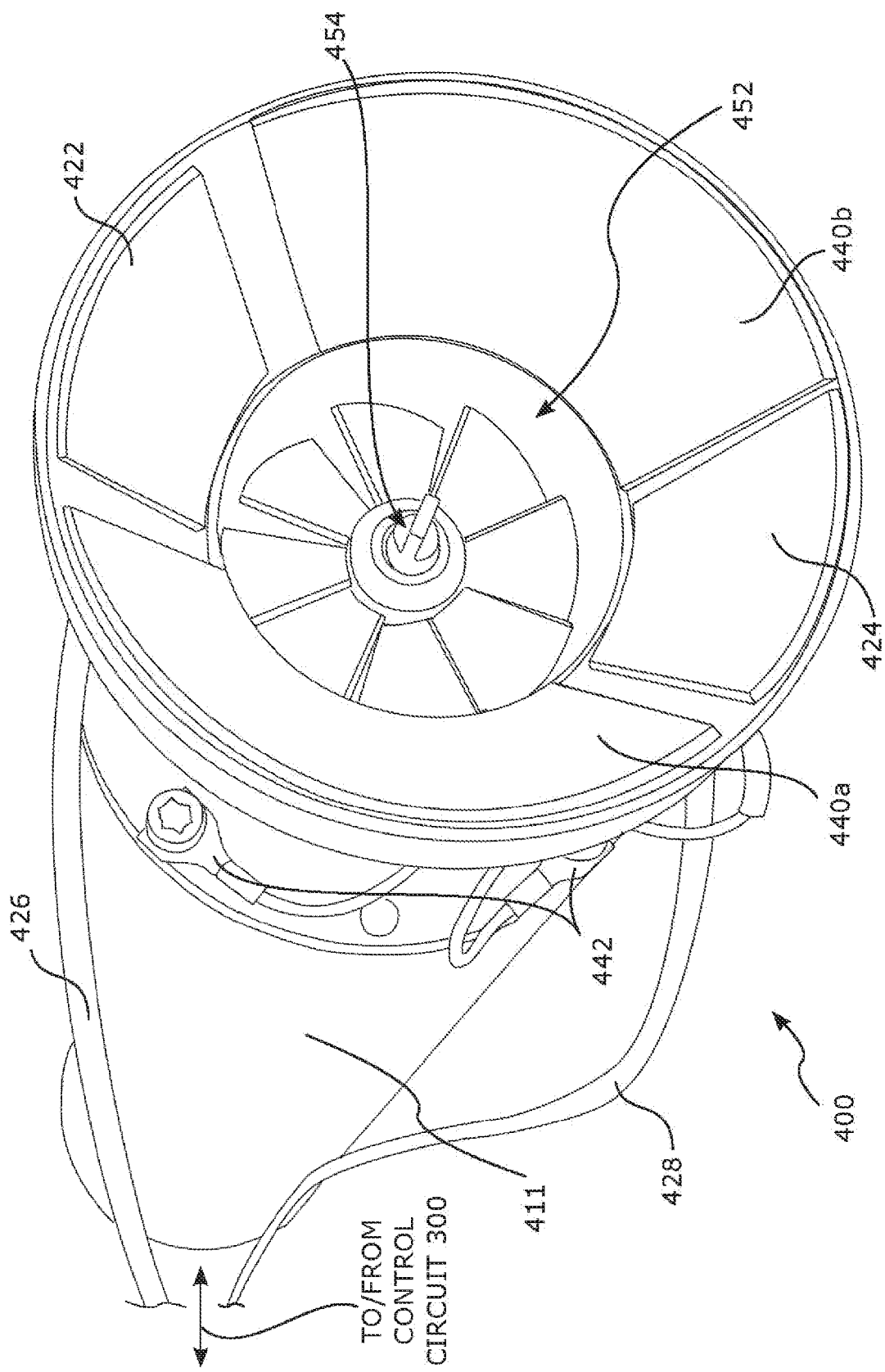
FIG. 4 is a view of a burner, according to an embodiment.

FIG. 4 is an oblique view of a burner 400, according to an embodiment. The burner 400 incorporates features described above with respect to FIGS. 1 and 3. First and second electrodes 422 and 424 may be disposed at a periphery of a flame region (e.g., flame region 130). Additionally or alternatively, a first electrode 454 may be disposed on or coincident with a fuel riser 454 and the electrodes 422, 424 may operate as second electrodes. Fuel and oxidant may be supplied through an air plenum 411 of the burner 400. The fuel and oxidant may each be supplied from a respective supply conduit (not shown) respectively in fluid connection with a fuel reservoir via a valve (e.g., fuel control valve 244 in FIG. 2) and an air supply via a blower (e.g., blower 246 in FIG. 2). The first and second electrodes 422, 424 may be patch electrodes and may be configured in electrical connection to a controller (e.g., control circuit 300 described above) respectively via first and second conductors 426, 428. In an embodiment, as illustrated, the burner 400 may include a swirler 452 configured to swirl the oxidant as it is propagated from the oxidant source (e.g., oxidant source 114). This permits the swirled oxidant to entrain fuel emitted from a fuel nozzle (which may be coincident with a first electrode 454), thus aiding mixture of the fuel and oxidant to a substantially homogeneous fuel and oxidant mixture. Elements 440a, 440b may be electrically connected to ground 442 in illustrative embodiments.

In some embodiments, the controller may be configured to offset a time varying signal from two or more of the electrodes 422, 424, 440a, 440b, and/or 454 such that the effect of the time varying signal from one electrode may be assessed at one or more of the other electrodes. By this operation not only the presence or absence, but additional flame characteristics may be assessed, such as a relative position or size of the flame.

Although the disclosure focuses on use of the flame sensor 120 to detect presence or absence of a flame, it will be appreciated by those having skill in the art that the flame sensor 120 may be used to detect a flame at another portion of a combustion system 200. For example, a flame sensor 120 may be positioned to detect flame presence or other characteristics downstream at a main flame holder, such as a perforated flame holder. In another example, a flame sensing device similar to the flame sensor 120 of the burner 100 described above may be implemented to detect presence or absence of undesirable flashback upstream from a perforated flame holder or other flame holder. In some embodiments, the flame sensor 120 may be configured to sense the presence, absence, or another quality of non-flame combustion products downstream from a flame holder.

Figure 5:
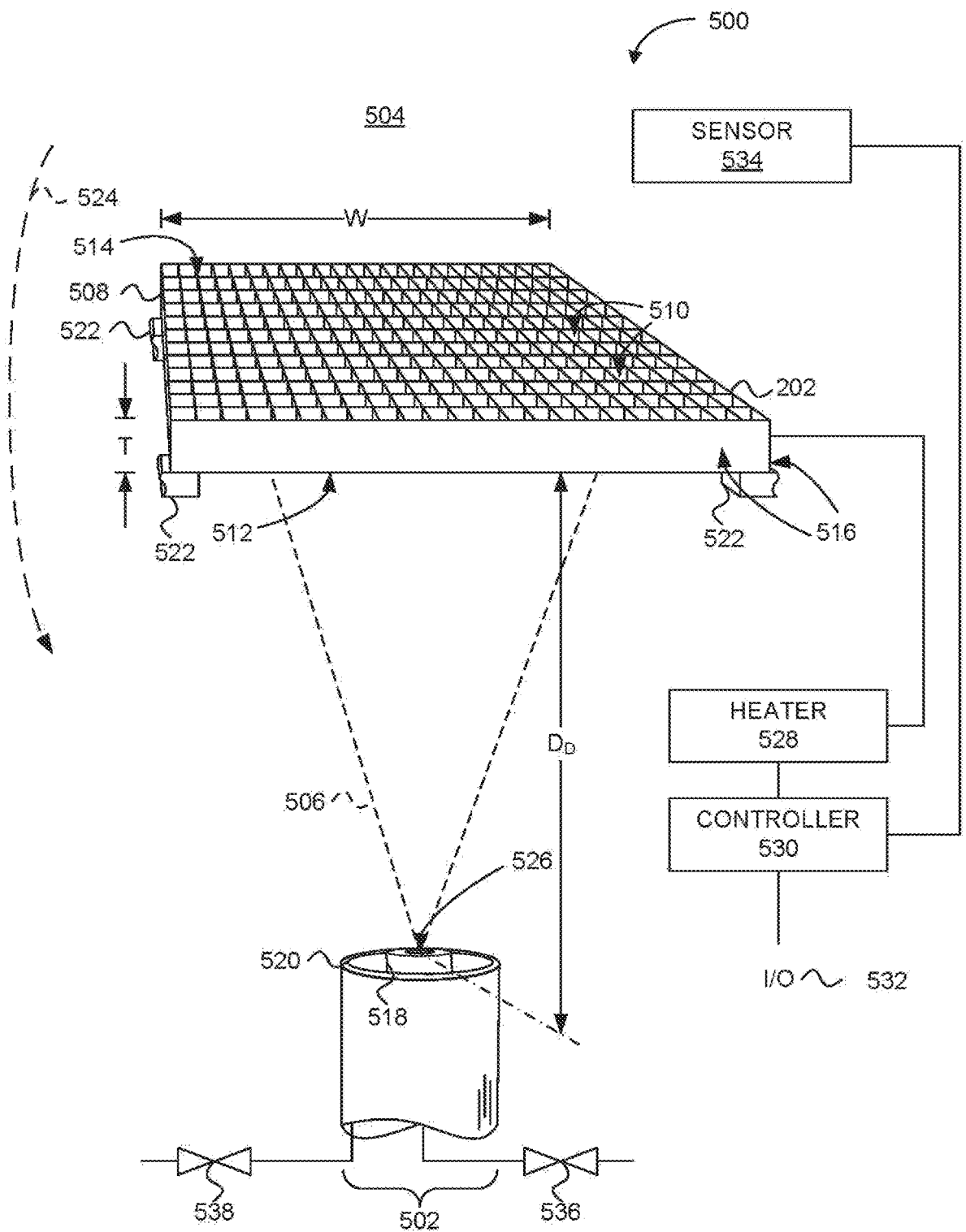
FIG. 5 is a simplified diagram of a combustion system including a perforated flame holder configured to hold a combustion reaction, according to an embodiment.

FIG. 5 is a simplified diagram of a burner system 500 including a perforated flame holder 202 configured to hold a combustion reaction, according to an embodiment. As used herein, the terms perforated flame holder, perforated reaction holder, porous flame holder, porous reaction holder, duplex, and duplex tile shall be considered synonymous unless further definition is provided.

Experiments performed by the inventors have shown that perforated flame holders 202 described herein can support very clean combustion. Specifically, in experimental use of burner systems 500 ranging from scale to full scale, output of oxides of nitrogen (NOx) was measured to range from low single digit parts per million (ppm) down to undetectable (less than 1 ppm) concentration of NOx at the stack. These remarkable results were measured at 3% (dry) oxygen ($O_2$) concentration with undetectable carbon monoxide (CO) at stack temperatures typical of industrial furnace applications (1700-1600° F.). Moreover, these results did not require any extraordinary measures such as selective catalytic reduction (SCR), selective non-catalytic reduction (SNCR), water/steam injection, external flue gas recirculation (FGR), or other heroic extremes that may be required for conventional burners to even approach such clean combustion.

According to embodiments, the burner system 500 includes a fuel and oxidant source 502 disposed to output fuel and oxidant into a combustion volume 504 to form a fuel and oxidant mixture 506. As used herein, the terms fuel and oxidant mixture and fuel stream may be used interchangeably and considered synonymous depending on the context, unless further definition is provided. As used herein, the terms combustion volume, combustion chamber, furnace volume, and the like shall be considered synonymous unless further definition is provided. The perforated flame holder 202 is disposed in the combustion volume 504 and positioned to receive the fuel and oxidant mixture 506.

Figure 6:
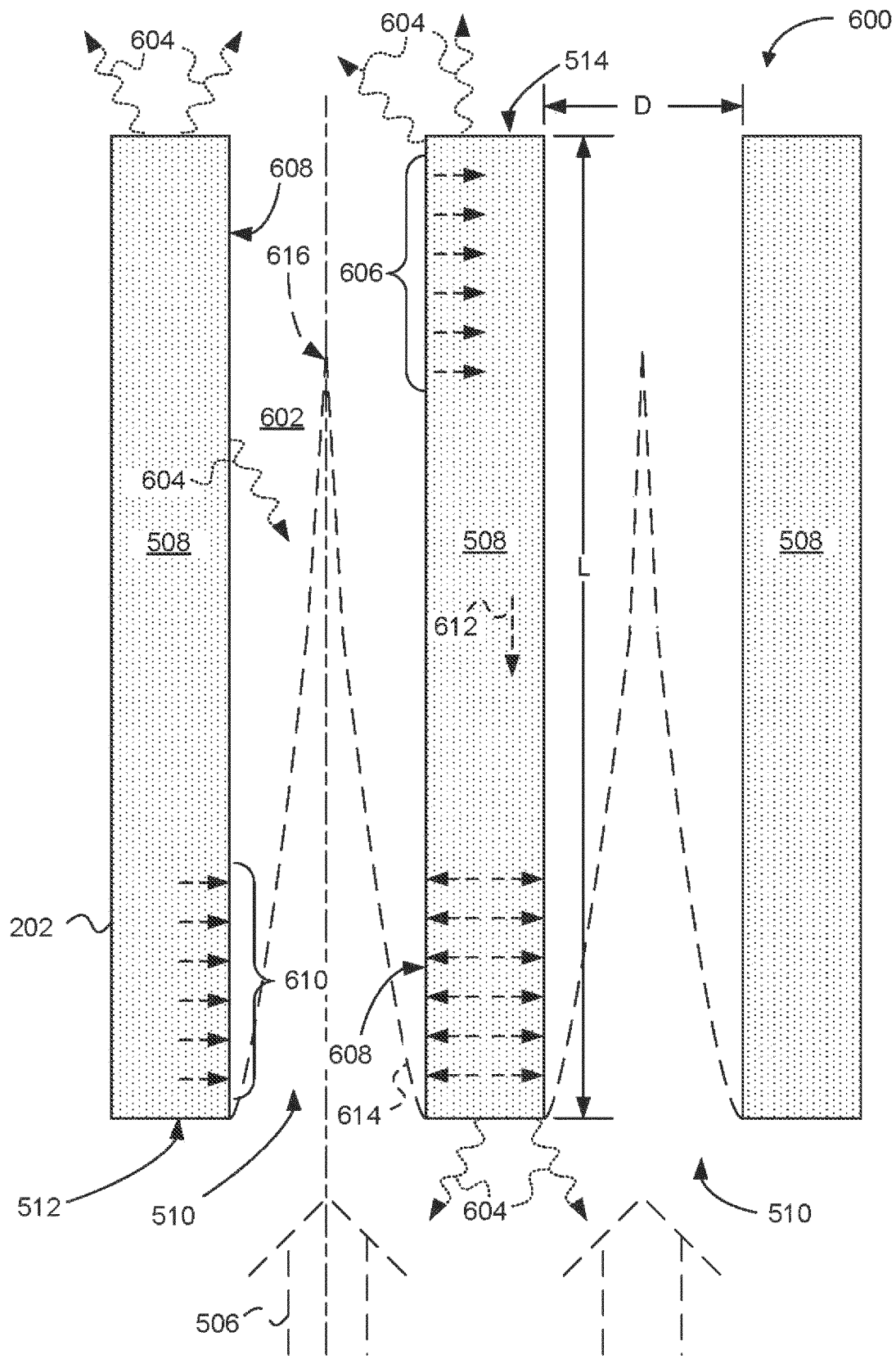
FIG. 6 is a side sectional diagram of a portion of the perforated flame holder of FIG. 5, according to an embodiment.

FIG. 6 is a side sectional diagram 600 of a portion of the perforated flame holder 202 of FIGS. 2 and 5, according to an embodiment. Referring to FIGS. 5 and 6, the perforated flame holder 202 includes a perforated flame holder body 508 defining a plurality of perforations 510 aligned to receive the fuel and oxidant mixture 506 from the fuel and oxidant source 502. As used herein, the terms perforation, pore, aperture, elongated aperture, and the like, in the context of the perforated flame holder 202, shall be considered synonymous unless further definition is provided. The perforations 510 are configured to collectively hold a combustion reaction 606 supported by the fuel and oxidant mixture 506.

The fuel can include hydrogen, a hydrocarbon gas, a vaporized hydrocarbon liquid, an atomized hydrocarbon liquid, or a powdered or pulverized solid. The fuel can be a single species or can include a mixture of gas(es), vapor(s), atomized liquid(s), and/or pulverized solid(s). For example, in a process heater application the fuel can include fuel gas or byproducts from the process that include carbon monoxide (CO), hydrogen ($H_2$), and methane ($CH_4$). In another application the fuel can include natural gas (mostly $CH_4$) or propane ($C_3H_8$). In another application, the fuel can include #2 fuel oil or #6 fuel oil. Dual fuel applications and flexible fuel applications are similarly contemplated by the inventors. The oxidant can include oxygen carried by air, flue gas, and/or can include another oxidant, either pure or carried by a carrier gas. The terms oxidant and oxidizer shall be considered synonymous herein.

According to an embodiment, the perforated flame holder body 508 can be bounded by an input face 512 disposed to receive the fuel and oxidant mixture 506, an output face 514 facing away from the fuel and oxidant source 502, and a peripheral surface 516 defining a lateral extent of the perforated flame holder 202. The plurality of perforations 510 which are defined by the perforated flame holder body 508 extend from the input face 512 to the output face 514. The plurality of perforations 510 can receive the fuel and oxidant mixture 506 at the input face 512. The fuel and oxidant mixture 506 can then combust in or near the plurality of perforations 510 and combustion products can exit the plurality of perforations 510 at or near the output face 514.

According to an embodiment, the perforated flame holder 202 is configured to hold a majority of the combustion reaction 606 within the perforations 510. For example, on a steady-state basis, more than half the molecules of fuel output into the combustion volume 504 by the fuel and oxidant source 502 may be converted to combustion products between the input face 512 and the output face 514 of the perforated flame holder 202. According to an alternative interpretation, more than half of the heat or thermal energy output by the combustion reaction 606 may be output between the input face 512 and the output face 514 of the perforated flame holder 202. As used herein, the terms heat, heat energy, and thermal energy shall be considered synonymous unless further definition is provided. As used above, heat energy and thermal energy refer generally to the released chemical energy initially held by reactants during the combustion reaction 606. As used elsewhere herein, heat, heat energy and thermal energy correspond to a detectable temperature rise undergone by real bodies characterized by heat capacities. Under nominal operating conditions, the perforations 510 can be configured to collectively hold at least 80% of the combustion reaction 606 between the input face 512 and the output face 514 of the perforated flame holder 202. In some experiments, the inventors produced a combustion reaction 606 that was apparently wholly contained in the perforations 510 between the input face 512 and the output face 514 of the perforated flame holder 202. According to an alternative interpretation, the perforated flame holder 202 can support combustion between the input face 512 and the output face 514 when combustion is "time-averaged." For example, during transients, such as before the perforated flame holder 202 is fully heated, or if too high a (cooling) load is placed on the system, the combustion may travel somewhat downstream from the output face 514 of the perforated flame holder 202. Alternatively, if the cooling load is relatively low and/or the furnace temperature reaches a high level, the combustion may travel somewhat upstream of the input face 512 of the perforated flame holder 202.

While a "flame" is described in a manner intended for ease of description, it should be understood that in some instances, no visible flame is present. Combustion occurs primarily within the perforations 510, but the "glow" of combustion heat is dominated by a visible glow of the perforated flame holder 202 itself. In other instances, the inventors have noted transient "huffing" or "flashback" wherein a visible flame momentarily ignites in a region lying between the input face 512 of the perforated flame holder 202 and a fuel nozzle 518, within the dilution region DD. Such transient huffing or flashback is generally short in duration such that, on a time-averaged basis, a majority of combustion occurs within the perforations 510 of the perforated flame holder 202, between the input face 512 and the output face 514. In still other instances, the inventors have noted apparent combustion occurring downstream from the output face 514 of the perforated flame holder 202, but still a majority of combustion occurred within the perforated flame holder 202 as evidenced by continued visible glow from the perforated flame holder 202 that was observed.

The perforated flame holder 202 can be configured to receive heat from the combustion reaction 606 and output a portion of the received heat as thermal radiation 604 to heat-receiving structures (e.g., furnace walls and/or radiant section working fluid tubes) in or adjacent to the combustion volume 504. As used herein, terms such as radiation, thermal radiation, radiant heat, heat radiation, etc., are to be construed as being substantially synonymous, unless further definition is provided. Specifically, such terms refer to blackbody-type radiation of electromagnetic energy, primarily at infrared wavelengths, but also at visible wavelengths owing to elevated temperature of the perforated flame holder body 508.

Referring especially to FIG. 6, the perforated flame holder 202 outputs another portion of the received heat to the fuel and oxidant mixture 506 received at the input face 512 of the perforated flame holder 202. The perforated flame holder body 508 may receive heat from the combustion reaction 606 at least in heat receiving regions 606 of perforation walls 608. Experimental evidence has suggested to the inventors that the position of the heat receiving regions 606, or at least the position corresponding to a maximum rate of receipt of heat, can vary along the length of the perforation walls 608. In some experiments, the location of maximum receipt of heat was apparently between ⅓ and ½ of the distance from the input face 512 to the output face 514 (i.e., somewhat nearer to the input face 512 than to the output face 514). The inventors contemplate that the heat receiving regions 606 may lie nearer to the output face 514 of the perforated flame holder 202 under other conditions. Most probably, there is no clearly defined edge of the heat receiving regions 606 (or for that matter, heat output regions 610, described below). For ease of understanding, the heat receiving regions 606 and the heat output regions 610 will be described as particular regions 606, 610.

The perforated flame holder body 508 can be characterized by a heat capacity. The perforated flame holder body 508 may hold thermal energy from the combustion reaction 606 in an amount corresponding to the heat capacity multiplied by temperature rise, and transfer the thermal energy from the heat receiving regions 606 to the heat output regions 610 of the perforation walls 608. Generally, the heat output regions 610 are nearer to the input face 512 than are the heat receiving regions 606. According to one interpretation, the perforated flame holder body 508 can transfer heat from the heat receiving regions 606 to the heat output regions 610 via thermal radiation, depicted graphically as 604. According to another interpretation, the perforated flame holder body 508 can transfer heat from the heat receiving regions 606 to the heat output regions 610 via heat conduction along heat conduction paths 612. The inventors contemplate that multiple heat transfer mechanisms including conduction, radiation, and possibly convection may be operative in transferring heat from the heat receiving regions 606 to the heat output regions 610. In this way, the perforated flame holder 202 may act as a heat source to maintain the combustion reaction 606, even under conditions where a combustion reaction 606 would not be stable when supported from a conventional flame holder.

The inventors believe that the perforated flame holder 202 causes the combustion reaction 606 to begin within thermal boundary layers 614 formed adjacent to the walls 608 of the perforations 510. Insofar as combustion is generally understood to include a large number of individual reactions, and since a large portion of combustion energy is released within the perforated flame holder 202, it is apparent that at least a majority of the individual reactions occur within the perforated flame holder 202. As the relatively cool fuel and oxidant mixture 506 approaches the input face 512, the flow is split into portions that respectively travel through individual perforations 510. The hot perforated flame holder body 508 transfers heat to the fluid, notably within the thermal boundary layers 614 that progressively thicken as more and more heat is transferred to the incoming fuel and oxidant mixture 506. After reaching a combustion temperature (e.g., the auto-ignition temperature of the fuel), the reactants continue to flow while a chemical ignition delay time elapses, over which time the combustion reaction 606 occurs. Accordingly, the combustion reaction 606 is shown as occurring within the thermal boundary layers 614. As flow progresses, the thermal boundary layers 614 merge at a merger point 616. Ideally, the merger point 616 lies between the input face 512 and the output face 514 that define the ends of the perforations 510. At some position along the length of a perforation 510, the combustion reaction 606 outputs more heat to the perforated flame holder body 508 than it receives from the perforated flame holder body 508. The heat is received at the heat receiving region 606, is held by the perforated flame holder body 508, and is transported to the heat output region 610 nearer to the input face 512, where the heat is transferred into the cool reactants (and any included diluent) to bring the reactants to the ignition temperature.

In an embodiment, each of the perforations 510 is characterized by a length L defined as a reaction fluid propagation path length between the input face 512 and the output face 514 of the perforated flame holder 202. As used herein, the term reaction fluid refers to matter that travels through a perforation 510. Near the input face 512, the reaction fluid includes the fuel and oxidant mixture 506 (optionally including nitrogen, flue gas, and/or other "non-reactive" species). Within the combustion reaction 606 region, the reaction fluid may include plasma associated with the combustion reaction 606, molecules of reactants and their constituent parts, any non-reactive species, reaction intermediates (including transition states), and reaction products. Near the output face 514, the reaction fluid may include reaction products and byproducts, non-reactive gas, and excess oxidant.

The plurality of perforations 510 can be each characterized by a transverse dimension D between opposing perforation walls 608. The inventors have found that stable combustion can be maintained in the perforated flame holder 202 if the length L of each perforation 510 is at least four times the transverse dimension D of the perforation 510. In other embodiments, the length L can be greater than six times the transverse dimension D. For example, experiments have been run where L is at least eight, at least twelve, at least sixteen, and at least twenty-four times the transverse dimension D. Preferably, the length L is sufficiently long for the thermal boundary layers 614 to form adjacent to the perforation walls 608 in a reaction fluid flowing through the perforations 510 to converge at the merger points 616 within the perforations 510 between the input face 512 and the output face 514 of the perforated flame holder 202. In experiments, the inventors have found L/D ratios between 12 and 48 to work well (i.e., produce low NOx, produce low CO, and maintain stable combustion).

The perforated flame holder body 508 can be configured to convey heat between adjacent perforations 510. The heat conveyed between the adjacent perforations 510 can be selected to cause heat output from the combustion reaction portion 606 in a first perforation 510 to supply heat to stabilize a combustion reaction portion 606 in an adjacent perforation 510.

Referring especially to FIG. 5, the fuel and oxidant source 502 can further include the fuel nozzle 518, configured to output the fuel, and an oxidant source 520 configured to output a fluid including the oxidant. For example, the fuel nozzle 518 can be configured to output pure fuel. The oxidant source 520 can be configured to output combustion air carrying oxygen, and optionally, flue gas.

The perforated flame holder 202 can be held by a perforated flame holder support structure 522 configured to hold the perforated flame holder 202 at a dilution distance DD away from the fuel nozzle 518. The fuel nozzle 518 can be configured to emit a fuel jet selected to entrain the oxidant to form the fuel and oxidant mixture 506 as the fuel jet and the oxidant travel along a path to the perforated flame holder 202 through the dilution distance DD between the fuel nozzle 518 and the perforated flame holder 202. Additionally or alternatively (particularly when a blower is used to deliver the oxidant contained in combustion air), the oxidant or combustion air source 520 can be configured to entrain the fuel and the fuel and the oxidant travel through the dilution distance DD. In some embodiments, a flue gas recirculation path 524 can be provided. Additionally or alternatively, the fuel nozzle 518 can be configured to emit a fuel jet selected to entrain the oxidant and to entrain flue gas as the fuel jet travels through the dilution distance DD between the fuel nozzle 518 and the input face 512 of the perforated flame holder 202.

The fuel nozzle 518 can be configured to emit the fuel through one or more fuel orifices 526 having an inside diameter dimension that is referred to as "nozzle diameter." The perforated flame holder support structure 522 can support the perforated flame holder 202 to receive the fuel and oxidant mixture 506 at the distance DD away from the fuel nozzle 518 greater than 20 times the nozzle diameter. In another embodiment, the perforated flame holder 202 is disposed to receive the fuel and oxidant mixture 506 at the distance DD away from the fuel nozzle 518 between 100 times and 1100 times the nozzle diameter. Preferably, the perforated flame holder support structure 522 is configured to hold the perforated flame holder 202 at a distance about 200 times or more of the nozzle diameter away from the fuel nozzle 518. When the fuel and oxidant mixture 506 travels about 200 times the nozzle diameter or more, the mixture is sufficiently homogenized to cause the combustion reaction 606 to produce minimal NOx.

The fuel and oxidant source 502 can alternatively include a premix fuel and oxidant source, according to an embodiment. A premix fuel and oxidant source can include a premix chamber (not shown), a fuel nozzle configured to output fuel into the premix chamber, and an oxidant (e.g., combustion air) channel configured to output the oxidant into the premix chamber. A flame arrestor can be disposed between the premix fuel and oxidant source and the perforated flame holder 202 and be configured to prevent flame flashback into the premix fuel and oxidant source.

The oxidant source 520, whether configured for entrainment in the combustion volume 504 or for premixing, can include a blower configured to force the oxidant through the fuel and oxidant source 502.

The perforated flame holder support structure 522 can be configured to support the perforated flame holder 202 from a floor or wall (not shown) of the combustion volume 504, for example. In another embodiment, the perforated flame holder support structure 522 supports the perforated flame holder 202 from the fuel and oxidant source 502. Alternatively, the perforated flame holder support structure 522 can suspend the perforated flame holder 202 from an overhead structure (such as a flue, in the case of an up-fired system). The perforated flame holder support structure 522 can support the perforated flame holder 202 in various orientations and directions.

The perforated flame holder 202 can include a single perforated flame holder body 508. In another embodiment, the perforated flame holder 202 can include a plurality of adjacent perforated flame holder sections that collectively provide a tiled perforated flame holder 202.

The perforated flame holder support structure 522 can be configured to support the plurality of perforated flame holder sections. The perforated flame holder support structure 522 can include a metal superalloy, a cementitious, and/or ceramic refractory material. In an embodiment, the plurality of adjacent perforated flame holder sections can be joined with a fiber reinforced refractory cement.

The perforated flame holder 202 can have a width dimension W between opposite sides of the peripheral surface 516 at least twice a thickness dimension T between the input face 512 and the output face 514. In another embodiment, the perforated flame holder 202 can have a width dimension W between opposite sides of the peripheral surface 516 at least three times, at least six times, or at least nine times the thickness dimension T between the input face 512 and the output face 514 of the perforated flame holder 202.

In an embodiment, the perforated flame holder 202 can have a width dimension W less than a width of the combustion volume 504. This can allow the flue gas recirculation path 524 from above to below the perforated flame holder 202 to lie between the peripheral surface 516 of the perforated flame holder 202 and the combustion volume wall (not shown).

Referring again to both FIGS. 5 and 6, the perforations 510 can be of various shapes. In an embodiment, the perforations 510 can include elongated squares, each having a transverse dimension D between opposing sides of the squares. In another embodiment, the perforations 510 can include elongated hexagons, each having a transverse dimension D between opposing sides of the hexagons. In yet another embodiment, the perforations 510 can include hollow cylinders, each having a transverse dimension D corresponding to a diameter of the cylinder. In another embodiment, the perforations 510 can include truncated cones or truncated pyramids (e.g., frustums), each having a transverse dimension D radially symmetric relative to a length axis that extends from the input face 512 to the output face 514. In some embodiments, the perforations 510 can each have a lateral dimension D equal to or greater than a quenching distance of the flame based on standard reference conditions. Alternatively, the perforations 510 may have lateral dimension D less than a standard reference quenching distance.

In one range of embodiments, each of the plurality of perforations 510 has a lateral dimension D between 0.05 inch and 1.0 inch. Preferably, each of the plurality of perforations 510 has a lateral dimension D between 0.1 inch and 0.5 inch. For example, the plurality of perforations 510 can each have a lateral dimension D of about 0.2 to 0.4 inch.

The void fraction of a perforated flame holder 202 is defined as the total volume of all perforations 510 in a section of the perforated flame holder 202 divided by a total volume of the perforated flame holder 202 including perforated flame holder body 508 and perforations 510. The perforated flame holder 202 should have a void fraction between 0.10 and 0.90. In an embodiment, the perforated flame holder 202 can have a void fraction between 0.30 and 0.80. In another embodiment, the perforated flame holder 202 can have a void fraction of about 0.70. Using a void fraction of about 0.70 was found to be especially effective for producing very low NOx.

The perforated flame holder 202 can be formed from a fiber reinforced cast refractory material and/or a refractory material such as an aluminum silicate material. For example, the perforated flame holder 202 can be formed to include mullite or cordierite. Additionally or alternatively, the perforated flame holder body 508 can include a metal superalloy such as Inconel or Hastelloy. The perforated flame holder body 508 can define a honeycomb. Honeycomb is an industrial term of art that need not strictly refer to a hexagonal cross section and most usually includes cells of square cross section. Honeycombs of other cross-sectional areas are also known.

The inventors have found that the perforated flame holder 202 can be formed from VERSAGRID® ceramic honeycomb, available from Applied Ceramics, Inc. of Doraville, South Carolina.

The perforations 510 can be parallel to one another and normal to the input and the output faces 512, 514. In another embodiment, the perforations 510 can be parallel to one another and formed at an angle relative to the input and the output faces 512, 514. In another embodiment, the perforations 510 can be non-parallel to one another. In another embodiment, the perforations 510 can be non-parallel to one another and non-intersecting. In another embodiment, the perforations 510 can be intersecting. The perforated flame holder body 508 can be one piece or can be formed from a plurality of sections.

In another embodiment, which is not necessarily preferred, the perforated flame holder 202 may be formed from reticulated ceramic material. The term "reticulated" refers to a netlike structure. Reticulated ceramic material is often made by dissolving a slurry into a sponge of specified porosity, allowing the slurry to harden, and burning away the sponge and curing the ceramic.

In another embodiment, which is not necessarily preferred, the perforated flame holder 202 may be formed from a ceramic material that has been punched, bored or cast to create channels.

In another embodiment, the perforated flame holder 202 can include a plurality of tubes or pipes bundled together. The plurality of perforations 510 can include hollow cylinders and can optionally also include interstitial spaces between the bundled tubes. In an embodiment, the plurality of tubes can include ceramic tubes. Refractory cement can be included between the tubes and configured to adhere the tubes together. In another embodiment, the plurality of tubes can include metal (e.g., superalloy) tubes. The plurality of tubes can be held together by a metal tension member circumferential to the plurality of tubes and arranged to hold the plurality of tubes together. The metal tension member can include stainless steel, a superalloy metal wire, and/or a superalloy metal band.

The perforated flame holder body 508 can alternatively include stacked perforated sheets of material, each sheet having openings that connect with openings of subjacent and superjacent sheets. The perforated sheets can include perforated metal sheets, ceramic sheets and/or expanded sheets. In another embodiment, the perforated flame holder body 508 can include discontinuous packing bodies such that the perforations 510 are formed in the interstitial spaces between the discontinuous packing bodies. In one example, the discontinuous packing bodies include structured packing shapes. In another example, the discontinuous packing bodies include random packing shapes. For example, the discontinuous packing bodies can include ceramic Raschig ring, ceramic Berl saddles, ceramic Intalox saddles, and/or metal rings or other shapes (e.g., Super Raschig Rings) that may be held together by a metal cage.

The inventors contemplate various explanations for why burner systems 500 including the perforated flame holder 202 provide such clean combustion.

According to an embodiment, the perforated flame holder 202 may act as a heat source to maintain the combustion reaction 606 even under conditions where the combustion reaction 606 would not be stable when supported by a conventional flame holder. This capability can be leveraged to support combustion using a leaner fuel-to-oxidant mixture than is typically feasible. Thus, according to an embodiment, at the point where the fuel stream 506 contacts the input face 512 of the perforated flame holder 202, an average fuel-to-oxidant ratio of the fuel stream 506 is below a (conventional) lower combustion limit of the fuel component of the fuel stream 506—lower combustion limit defines the lowest concentration of fuel at which the fuel and oxidant mixture 506 will burn when exposed to a momentary ignition source under normal atmospheric pressure and an ambient temperature of 25° C. (77° F.).

The perforated flame holder 202 and systems including the perforated flame holder 202 described herein were found to provide substantially complete combustion of CO (single digit ppm down to undetectable, depending on experimental conditions), while supporting low NOx. According to one interpretation, such a performance can be achieved due to a sufficient mixing used to lower peak flame temperatures (among other strategies). Flame temperatures tend to peak under slightly rich conditions, which can be evident in any diffusion flame that is insufficiently mixed. By sufficiently mixing, a homogenous and slightly lean mixture can be achieved prior to combustion. This combination can result in reduced flame temperatures, and thus reduced NOx formation. In one embodiment, "slightly lean" may refer to 3% $O_2$, i.e., an equivalence ratio of ~0.87. Use of even leaner mixtures is possible, but may result in elevated levels of $O_2$. Moreover, the inventors believe the perforation walls 608 may act as a heat sink for the combustion fluid. This effect may alternatively or additionally reduce combustion temperatures and lower NOx.

According to another interpretation, production of NOx can be reduced if the combustion reaction 606 occurs over a very short duration of time. Rapid combustion causes the reactants (including oxygen and entrained nitrogen) to be exposed to NOx-formation temperature for a time too short for NOx formation kinetics to cause significant production of NOx. The time required for the reactants to pass through the perforated flame holder 202 is very short compared to a conventional flame. The low NOx production associated with perforated flame holder combustion may thus be related to the short duration of time required for the reactants (and entrained nitrogen) to pass through the perforated flame holder 202.

Figure 7:
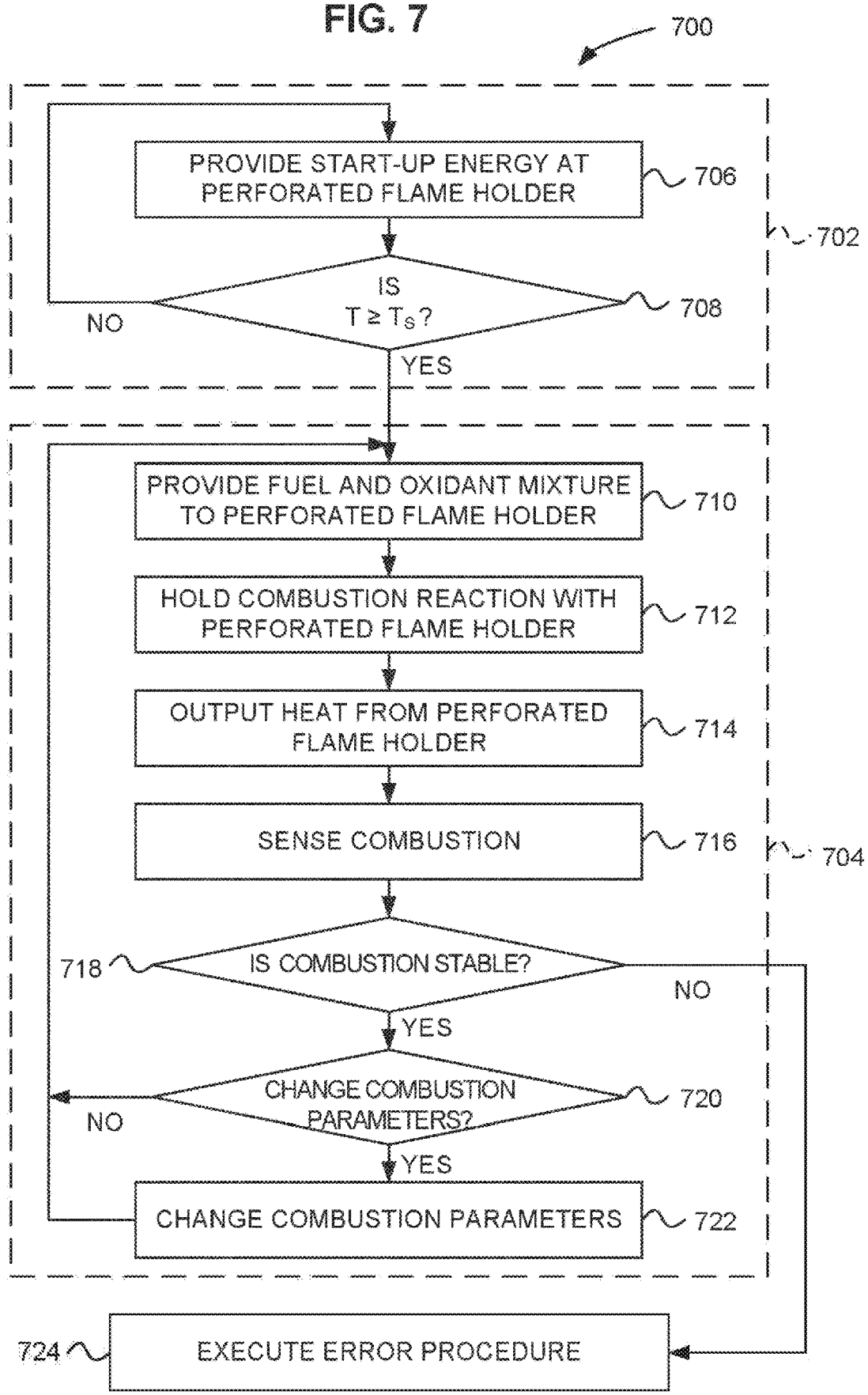
FIG. 7 is a flow chart showing a method for operating a combustion system including the perforated flame holder shown and described herein, according to an embodiment.

FIG. 7 is a flow chart showing a method 700 for operating a burner system including the perforated flame holder shown and described herein. To operate a burner system including a perforated flame holder, the perforated flame holder is first heated to a temperature sufficient to maintain combustion of the fuel and oxidant mixture.

According to a simplified description, the method 700 begins with step 702, wherein the perforated flame holder is preheated to a start-up temperature, $T_S$. After the perforated flame holder is raised to the start-up temperature, the method proceeds to step 704, wherein the fuel and the oxidant are provided to the perforated flame holder and combustion is held by the perforated flame holder.

According to a more detailed description, step 702 begins with step 706, wherein start-up energy is provided at the perforated flame holder. Simultaneously or following providing start-up energy, a decision step 708 determines whether the temperature T of the perforated flame holder is at or above the start-up temperature, $T_S$. As long as the temperature of the perforated flame holder is below its start-up temperature, the method 700 loops between steps 706 and 708 within the preheat step 702. In decision step 708, if the temperature T of at least a predetermined portion of the perforated flame holder is greater than or equal to the start-up temperature, the method 700 proceeds to overall step 704, wherein the fuel and the oxidant is supplied to and combustion is held by the perforated flame holder.

Step 704 may be broken down into several discrete steps, at least some of which may occur simultaneously.

Proceeding from decision step 708, a fuel and oxidant mixture is provided to the perforated flame holder, as shown in step 710. The fuel and the oxidant may be provided by a fuel and oxidant source that includes a separate fuel nozzle and oxidant (e.g., combustion air) source, for example. In this approach, the fuel and the oxidant are output in one or more directions selected to cause the fuel and oxidant mixture to be received by the input face of the perforated flame holder. The fuel may entrain the combustion air (or alternatively, the combustion air may dilute the fuel) to provide a fuel and oxidant mixture at the input face of the perforated flame holder at a fuel dilution selected for a stable combustion reaction that can be held within the perforations of the perforated flame holder.

Proceeding to step 712, the combustion reaction is held by the perforated flame holder.

In step 714, heat may be output from the perforated flame holder. The heat output from the perforated flame holder may be used to power an industrial process, heat a working fluid, generate electricity, or provide motive power, for example.

In optional step 716, the presence of combustion may be sensed. Various sensing approaches have been used and are contemplated by the inventors. Generally, combustion held by the perforated flame holder is very stable and no unusual sensing requirement is placed on the system. Combustion sensing may be performed using an infrared sensor, a video sensor, an ultraviolet sensor, a charged species sensor, thermocouple, thermopile, flame rod, and/or other combustion sensing apparatuses. In an additional or alternative variant of step 716, a flame or other ignition source may be provided to cause ignition of the fuel and oxidant mixture in the event combustion is lost at the perforated flame holder.

Proceeding to decision step 718, if combustion is sensed not to be stable, the method 700 may exit to step 724, wherein an error procedure is executed. For example, the error procedure may include turning off fuel flow, re-executing the preheating step 702, outputting an alarm signal, igniting a stand-by combustion system, or other steps. According to embodiments, the error procedure may include introducing activated particles into the flame region 130 to initiate and/or stabilize combustion. The activated particles may include radicals (as a low temperature plasma) and/or ions and electrons (as a high temperature plasma). Methods of providing activated particles are disclosed in related applications, incorporated by reference above.

If, in decision step 718, combustion in the perforated flame holder is determined to be stable, the method 700 proceeds to decision step 720, wherein it is determined if combustion parameters should be changed. If no combustion parameters are to be changed, the method loops (within step 704) back to step 710, and the combustion process continues. If a change in combustion parameters is indicated, the method 700 proceeds to step 722, wherein the combustion parameter change is executed. After changing the combustion parameter(s), the method loops (within step 704) back to step 710, and combustion continues.

Combustion parameters may be scheduled to be changed, for example, if a change in heat demand is encountered. For example, if less heat is required (e.g., due to decreased electricity demand, decreased motive power requirement, or lower industrial process throughput), the fuel and oxidant flow rate may be decreased in step 722. Conversely, if heat demand is increased, then fuel and oxidant flow may be increased. Additionally or alternatively, if the combustion system is in a start-up mode, then fuel and oxidant flow may be gradually increased to the perforated flame holder over one or more iterations of the loop within step 704.

Referring again to FIG. 5, the burner system 500 includes a heater 528 operatively coupled to the perforated flame holder 202. As described in conjunction with FIGS. 6 and 7, the perforated flame holder 202 operates by outputting heat to the incoming fuel and oxidant mixture 506. After combustion is established, this heat is provided by the combustion reaction 606; but before combustion is established, the heat is provided by the heater 528.

Various heating apparatuses have been used and are contemplated by the inventors. In some embodiments, the heater 528 can include a flame holder configured to support a flame disposed to heat the perforated flame holder 202. The fuel and oxidant source 502 can include a fuel nozzle 518 configured to emit a fuel stream 506 and an oxidant source 520 configured to output oxidant (e.g., combustion air) adjacent to the fuel stream 506. The fuel nozzle 518 and oxidant source 520 can be configured to output the fuel stream 506 to be progressively diluted by the oxidant (e.g., combustion air). The perforated flame holder 202 can be disposed to receive a diluted fuel and oxidant mixture 506 that supports a combustion reaction 606 that is stabilized by the perforated flame holder 202 when the perforated flame holder 202 is at an operating temperature. A start-up flame holder, in contrast, can be configured to support a start-up flame at a location corresponding to a relatively unmixed fuel and oxidant mixture that is stable without stabilization provided by the heated perforated flame holder 202.

The burner system 500 can further include a controller 530 operatively coupled to the heater 528 and to a data interface 532. For example, the controller 530 can be configured to control a start-up flame holder actuator configured to cause the start-up flame holder to hold the start-up flame when the perforated flame holder 202 needs to be pre-heated and to not hold the start-up flame when the perforated flame holder 202 is at an operating temperature (e.g., when $T \geq T_S$).

Various approaches for actuating a start-up flame are contemplated. In one embodiment, the start-up flame holder includes a mechanically-actuated bluff body configured to be actuated to intercept the fuel and oxidant mixture 506 to cause heat-recycling and/or stabilizing vortices and thereby hold a start-up flame; or to be actuated to not intercept the fuel and oxidant mixture 506 to cause the fuel and oxidant mixture 506 to proceed to the perforated flame holder 202. In another embodiment, a fuel control valve, blower, and/or damper may be used to select a fuel and oxidant mixture 506 flow rate that is sufficiently low for a start-up flame to be jet-stabilized; and upon reaching a perforated flame holder 202 operating temperature, the flow rate may be increased to "blow out" the start-up flame. In another embodiment, the heater 528 may include an electrical power supply operatively coupled to the controller 530 and configured to apply an electrical charge or voltage to the fuel and oxidant mixture 506. An electrically conductive start-up flame holder may be selectively coupled to a voltage ground or other voltage selected to attract the electrical charge in the fuel and oxidant mixture 506. The attraction of the electrical charge was found by the inventors to cause a start-up flame to be held by the electrically conductive start-up flame holder.

In another embodiment, the heater 528 may include an electrical resistance heater configured to output heat to the perforated flame holder 202 and/or to the fuel and oxidant mixture 506. The electrical resistance heater 528 can be configured to heat up the perforated flame holder 202 to an operating temperature. The heater 528 can further include a power supply and a switch operable, under control of the controller 530, to selectively couple the power supply to the electrical resistance heater 528.

An electrical resistance heater 528 can be formed in various ways. For example, the electrical resistance heater 528 can be formed from KANTHAL® wire (available from Sandvik Materials Technology division of Sandvik AB of Hallstahammar, Sweden) threaded through at least a portion of the perforations 510 defined by the perforated flame holder body 508. Alternatively, the heater 528 can include an inductive heater, a high-energy beam heater (e.g., microwave or laser), a frictional heater, electro-resistive ceramic coatings, or other types of heating technologies.

Other forms of start-up apparatuses are contemplated. For example, the heater 528 can include an electrical discharge igniter or hot surface igniter configured to output a pulsed ignition to the oxidant and the fuel. Additionally or alternatively, a start-up apparatus can include a pilot flame apparatus disposed to ignite the fuel and oxidant mixture 506 that would otherwise enter the perforated flame holder 202. The electrical discharge igniter, hot surface igniter, and/or pilot flame apparatus can be operatively coupled to the controller 530, which can cause the electrical discharge igniter or pilot flame apparatus to maintain combustion of the fuel and oxidant mixture 506 in or upstream from the perforated flame holder 202 before the perforated flame holder 202 is heated sufficiently to maintain combustion.

The burner system 500 can further include a sensor 534 operatively coupled to the controller 530. The sensor 534 can include a heat sensor configured to detect infrared radiation or a temperature of the perforated flame holder 202. The control circuit 530 can be configured to control the heater 528 responsive to input from the sensor 534. Optionally, a fuel control valve 536 can be operatively coupled to the controller 530 and configured to control a flow of the fuel to the fuel and oxidant source 502. Additionally or alternatively, an oxidant blower or damper 538 can be operatively coupled to the controller 530 and configured to control flow of the oxidant (or combustion air).

The sensor 534 can further include a combustion sensor operatively coupled to the control circuit 530, the combustion sensor 534 being configured to detect a temperature, video image, and/or spectral characteristic of the combustion reaction 606 held by the perforated flame holder 202. The fuel control valve 536 can be configured to control a flow of the fuel from a fuel source to the fuel and oxidant source 502. The controller 530 can be configured to control the fuel control valve 536 responsive to input from the combustion sensor 534. The controller 530 can be configured to control the fuel control valve 536 and/or the oxidant blower or damper 538 to control a preheat flame type of heater 528 to heat the perforated flame holder 202 to an operating temperature. The controller 530 can similarly control the fuel control valve 536 and/or the oxidant blower or damper 538 to change the fuel and oxidant mixture 506 flow responsive to a heat demand change received as data via the data interface 532.

Figure 8A:
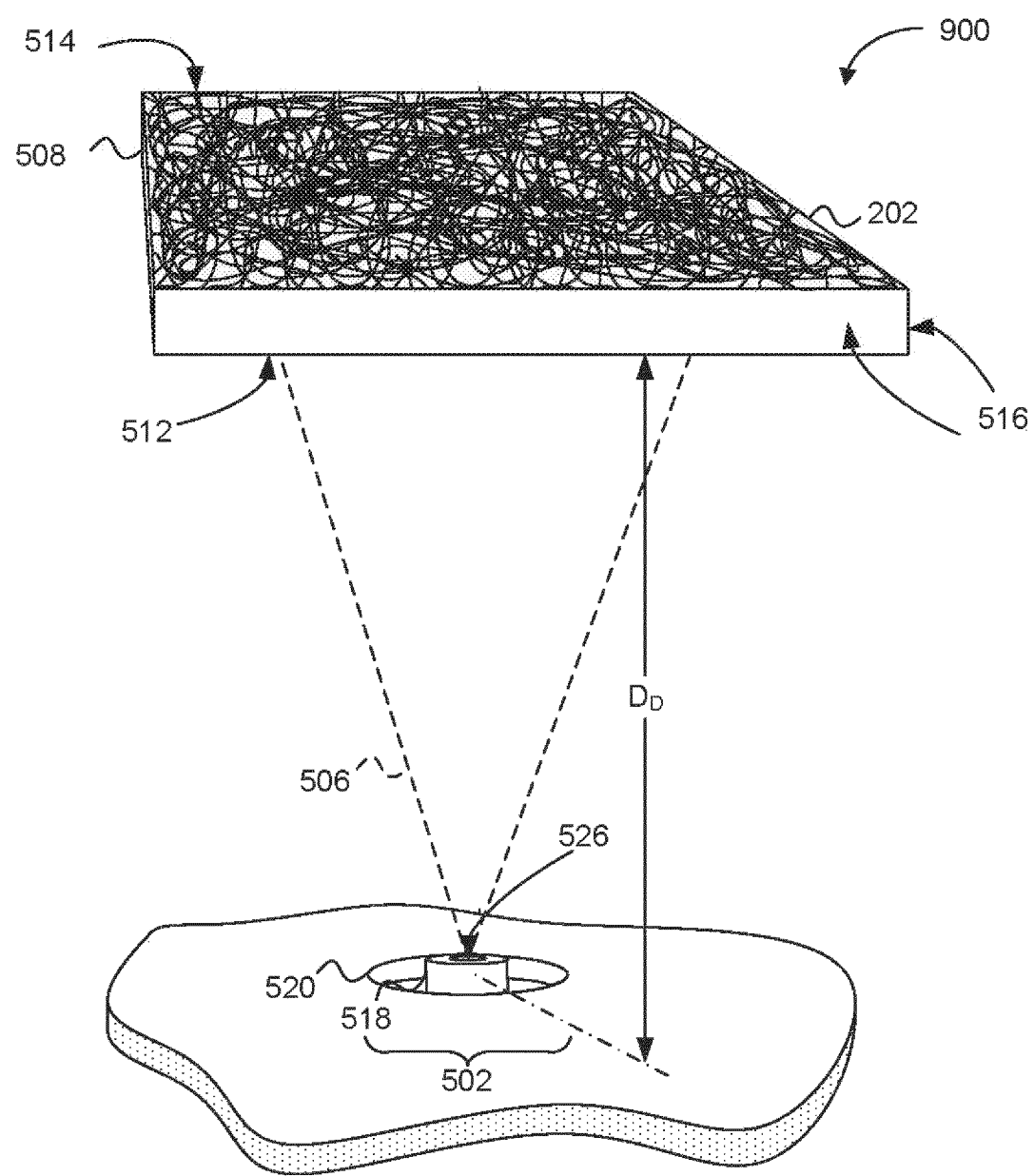
FIG. 8A is a simplified perspective view of a combustion system, including another alternative perforated flame holder, according to an embodiment.
Figure 8B:
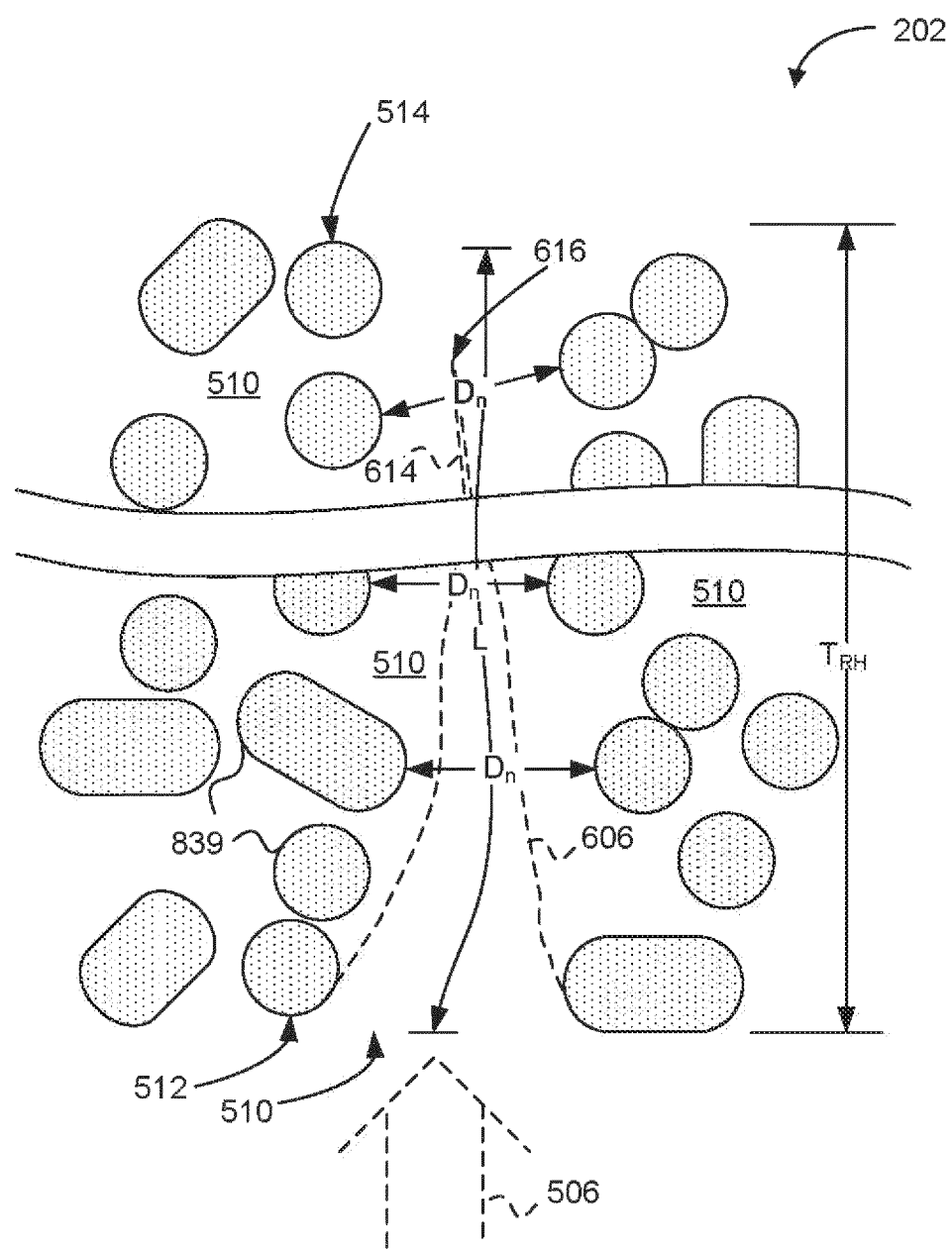
FIG. 8B is a simplified side sectional diagram of a portion of the reticulated ceramic perforated flame holder of FIG. 8A, according to an embodiment.

FIG. 8A is a simplified perspective view of a combustion system 800, including another alternative perforated flame holder 202, according to an embodiment. The perforated flame holder 202 is a reticulated ceramic perforated flame holder, according to an embodiment. FIG. 8B is a simplified side sectional diagram of a portion of the reticulated ceramic perforated flame holder 202 of FIG. 8A, according to an embodiment. The perforated flame holder 202 of FIGS. 8A, 8B can be implemented in the various combustion systems described herein, according to an embodiment. The perforated flame holder 202 is configured to support a combustion reaction (e.g., combustion reaction 602 of FIG. 6) of the fuel and oxidant mixture 506 received from the fuel and oxidant source 502 at least partially within the perforated flame holder 202. According to an embodiment, the perforated flame holder 202 can be configured to support a combustion reaction of the fuel and oxidant mixture 506 upstream, downstream, within, and adjacent to the reticulated ceramic perforated flame holder 202.

According to an embodiment, the perforated flame holder body 508 can include reticulated fibers 839. The reticulated fibers 839 can define branching perforations 510 that weave around and through the reticulated fibers 839. According to an embodiment, the perforations 510 are formed as passages between the reticulated fibers 839.

According to an embodiment, the reticulated fibers 839 are formed as a reticulated ceramic foam. According to an embodiment, the reticulated fibers 839 are formed using a reticulated polymer foam as a template. According to an embodiment, the reticulated fibers 839 can include alumina silicate. According to an embodiment, the reticulated fibers 839 can be formed from extruded mullite or cordierite. According to an embodiment, the reticulated fibers 839 can include Zirconia. According to an embodiment, the reticulated fibers 839 can include silicon carbide.

The term "reticulated fibers" refers to a netlike structure. According to an embodiment, the reticulated fibers 839 are formed from an extruded ceramic material. In reticulated fiber embodiments, the interaction between the fuel and oxidant mixture 506, the combustion reaction, and heat transfer to and from the perforated flame holder body 508 can function similarly to the embodiment shown and described above with respect to FIGS. 5-7. One difference in activity is a mixing between perforations 510, because the reticulated fibers 839 form a discontinuous perforated flame holder body 508 that allows flow back and forth between neighboring perforations 510.

According to an embodiment, the network of reticulated fibers 839 is sufficiently open for downstream reticulated fibers 839 to emit radiation for receipt by upstream reticulated fibers 839 for the purpose of heating the upstream reticulated fibers 839 sufficiently to maintain combustion of a fuel and oxidant mixture 506. Compared to a continuous perforated flame holder body 508, heat conduction paths (such as heat conduction paths 612 in FIG. 6) between reticulated fibers 839 are reduced due to separation of the reticulated fibers 839. This may cause relatively more heat to be transferred from a heat-receiving region or area (such as heat receiving region 606 in FIG. 6) to a heat-output region or area (such as heat-output region 610 of FIG. 6) of the reticulated fibers 839 via thermal radiation (shown as element 604 in FIG. 6).

According to an embodiment, individual perforations 510 may extend between an input face 512 to an output face 514 of the perforated flame holder 202. Perforations 510 may have varying lengths L. According to an embodiment, because the perforations 510 branch into and out of each other, individual perforations 510 are not clearly defined by a length L.

According to an embodiment, the perforated flame holder 202 is configured to support or hold a combustion reaction (see element 602 of FIG. 6) or a flame at least partially between the input face 512 and the output face 514. According to an embodiment, the input face 512 corresponds to a surface of the perforated flame holder 202 proximal to the fuel nozzle 518 or to a surface that first receives fuel. According to an embodiment, the input face 512 corresponds to an extent of the reticulated fibers 839 proximal to the fuel nozzle 518. According to an embodiment, the output face 514 corresponds to a surface distal to the fuel nozzle 518 or opposite the input face 512. According to an embodiment, the input face 512 corresponds to an extent of the reticulated fibers 839 distal to the fuel nozzle 518 or opposite to the input face 512.

According to an embodiment, the formation of thermal boundary layers 614, transfer of heat between the perforated flame holder body 508 and the gases flowing through the perforations 510, a characteristic perforation width dimension D, and the length L can each be regarded as related to an average or overall path through the perforated reaction holder 202. In other words, the dimension D can be determined as a root-mean-square of individual Dn values determined at each point along a flow path. Similarly, the length L can be a length that includes length contributed by tortuosity of the flow path, which may be somewhat longer than a straight-line distance $T_{RH}$ from the input face 512 to the output face 514 through the perforated reaction holder 202. According to an embodiment, the void fraction (expressed as (total perforated reaction holder 202 volume—reticulated fiber 839 volume)/total volume) is about 70%.

According to an embodiment, the reticulated ceramic perforated flame holder 202 is a tile about 1"×4"×4". According to an embodiment, the reticulated ceramic perforated flame holder 202 includes about 100 pores per square inch of surface area. Other materials and dimensions can also be used for a reticulated ceramic perforated flame holder 202 in accordance with principles of the present disclosure.

According to an embodiment, the reticulated ceramic perforated flame holder 202 can include shapes and dimensions other than those described herein. For example, the perforated flame holder 202 can include reticulated ceramic tiles that are larger or smaller than the dimensions set forth above. Additionally, the reticulated ceramic perforated flame holder 202 can include shapes other than generally cuboid shapes.

According to an embodiment, the reticulated ceramic perforated flame holder 202 can include multiple reticulated ceramic tiles. The multiple reticulated ceramic tiles can be joined together such that each ceramic tile is in direct contact with one or more adjacent reticulated ceramic tiles. The multiple reticulated ceramic tiles can collectively form a single perforated flame holder 202. Alternatively, each reticulated ceramic tile can be considered a distinct perforated flame holder 202.

Figure 9:
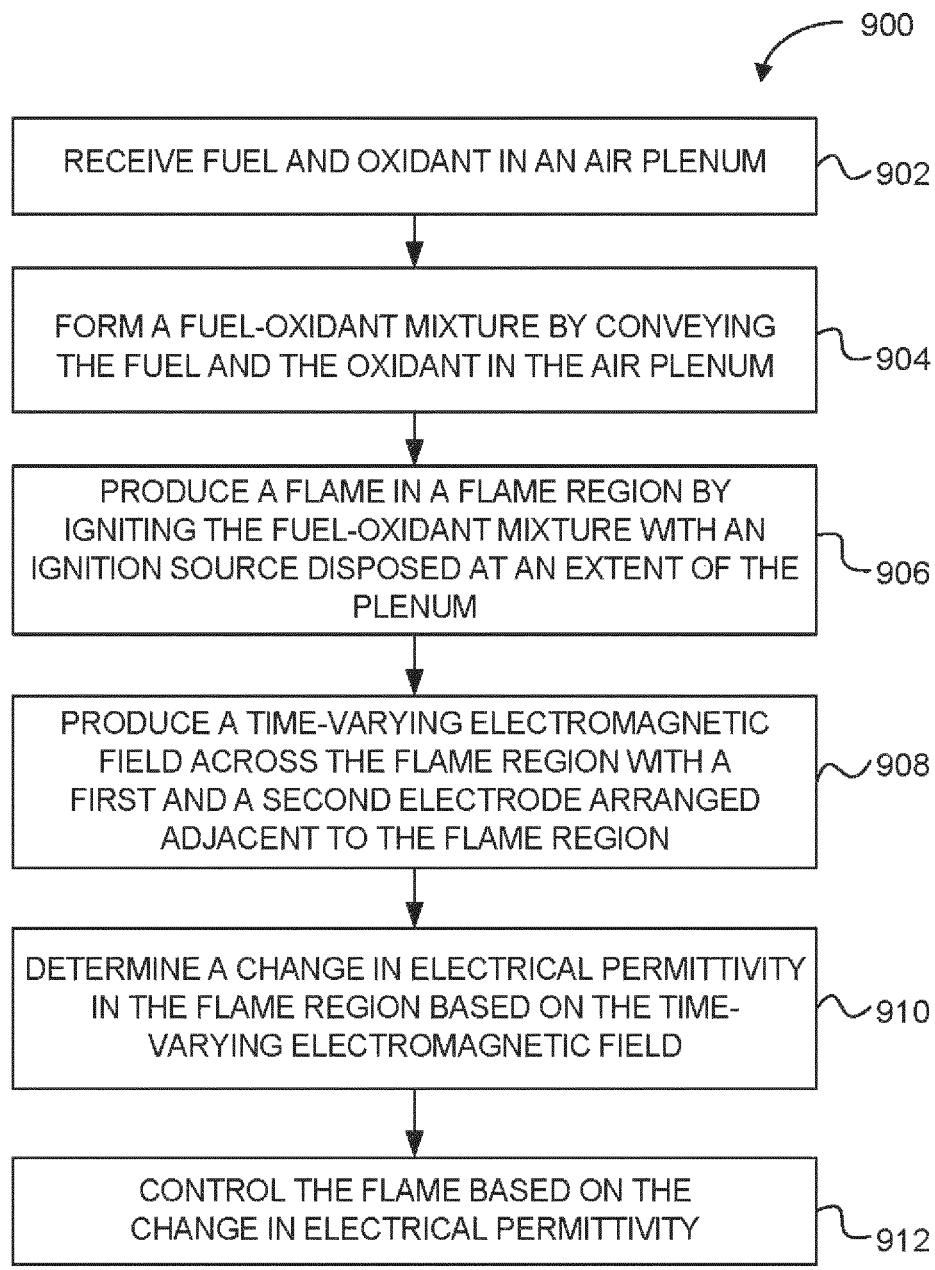
FIG. 9 is a flow chart showing a method, according to an embodiment.

FIG. 9 is a flow chart showing a method 900, according to an embodiment.

According to an embodiment, in step 902, the method 900 includes receiving, in an air plenum, fuel and oxidant. In step 904, the method 900 includes forming a fuel-oxidant mixture by conveying the fuel and the oxidant in the air plenum. In step 906, the method 900 includes producing a flame in a flame region by igniting the fuel-oxidant mixture with an ignition source disposed at an extent of the plenum. In step 908, the method 900 includes producing a time-varying electromagnetic field across the flame region with a first and a second electrode arranged adjacent to the flame region. In step 910, the method 900 includes determining a change in electrical permittivity in the flame region based on the time-varying electromagnetic field. In step 912, the method 900 includes controlling the flame based on the change in electrical permittivity.

Figure 10A:
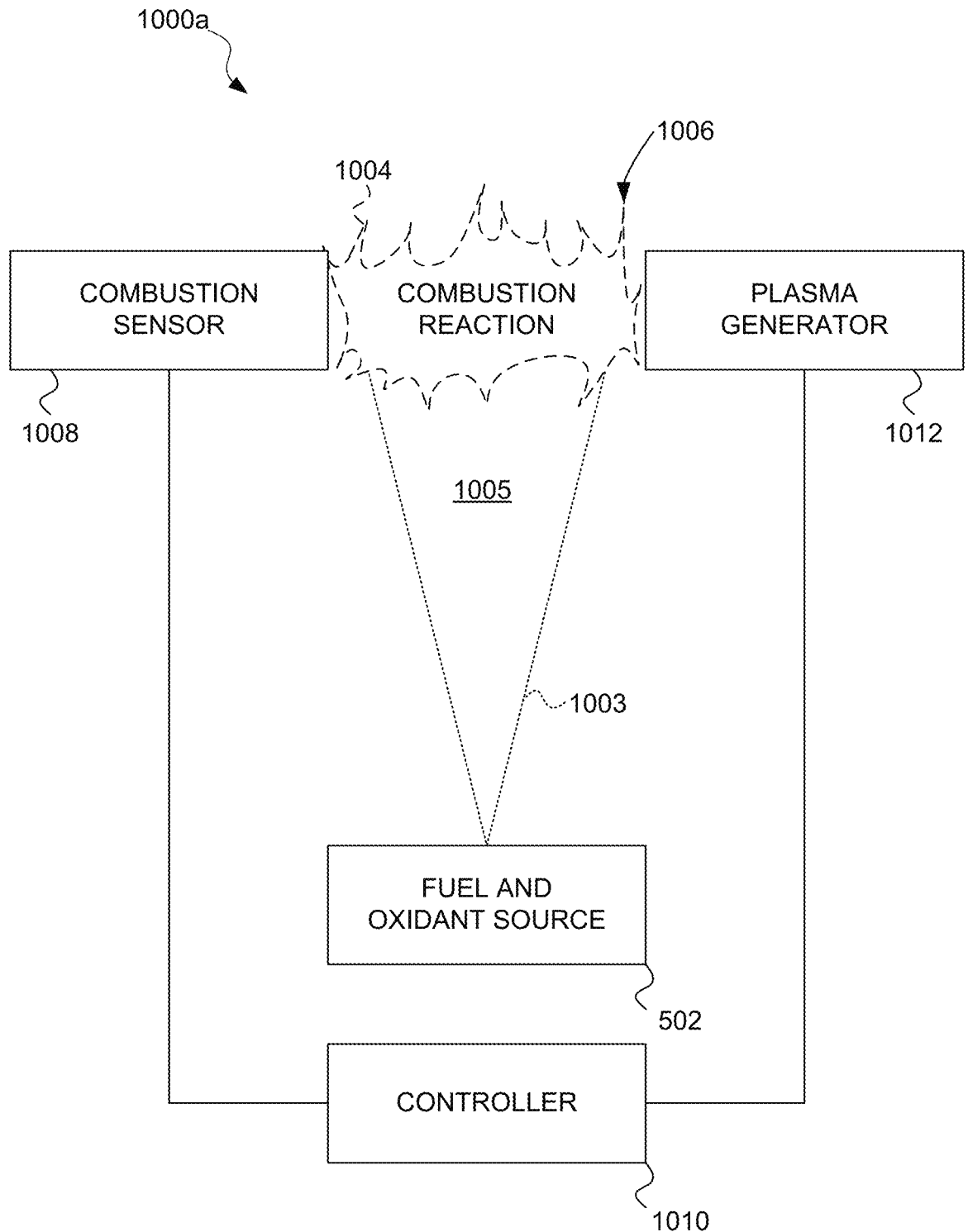
FIG. 10A is a block diagram of a combustion system including a plasma generator and a combustion sensor, according to an embodiment.

FIG. 10A is a block diagram of a combustion system 1000a, according to an embodiment. The combustion system 1000a may include a fuel and oxidant source 502, a combustion sensor 1008 positioned in a furnace volume 1005, a plasma generator 1012, and a controller 1010. In one embodiment, the combustion sensor 1008 can be configured to sense a combustion reaction of the fuel and the oxidant within the furnace volume 1005. In an alternative embodiment, the combustion sensor 1008 can be positioned within the furnace volume 1005. In one embodiment, the plasma generator 1012 can be positioned at least partially within the furnace volume 1005 and configured to stabilize the combustion reaction by generating a plasma. In one embodiment, the controller 1010 can be operatively coupled to the combustion sensor 1008 and the plasma generator 1012, and configured to receiving sensor signals from the combustion sensor 1008 indicative of a condition of the combustion reaction and to control operation of the plasma generator 1012 responsive to the sensor signals. The fuel and oxidant source 502, the combustion sensor 1008, the plasma generator 1012, the controller 1010, and a power source may work together to support a combustion reaction 1004 at a selected combustion location 1006 within the furnace volume 1005.

In one embodiment, the fuel and oxidant source 502 outputs fuel and oxidant into the furnace volume 1005. The fuel and oxidant can mix together to form a fuel and oxidant mixture 1003. The fuel and the oxidant can mix together to form the fuel and oxidant mixture 1003 as the fuel and the oxidant travel toward the selected combustion location 1006. Alternatively, the fuel and oxidant source 502 can output a premixed fuel and oxidant mixture 1003, according to an embodiment.

In one embodiment, the combustion system 1000a can include an ignition source to ignite the combustion reaction 1004 at the selected combustion location 1006. Once the combustion reaction 1004 has been ignited at the selected combustion location 1006 within the furnace volume 1005, the combustion system 1000a may operate to promote stability of the combustion reaction 1004 at the selected combustion location 1006. In an embodiment, the plasma generator 1012 may be driven to form a high temperature plasma to ignite the combustion reaction during an ignition phase, and then form a low temperature plasma to stabilize the combustion reaction during an operation phase.

In one embodiment, the plasma generator 1012 helps to stabilize the combustion reaction 1004. The plasma generator 1012 can help to stabilize the combustion reaction 1004 by generating a low temperature plasma in the vicinity of the combustion reaction 1004. The low temperature plasma can energize the mixture of fuel and oxidant 1003 to promote stable combustion of the fuel and oxidant mixture 1003. For example, if the combustion reaction 1004 is unstable at the selected combustion location 1006, the plasma generator 1012 can generate the low temperature plasma to energize the fuel and oxidant mixture 1003 to promote stable combustion of the fuel and oxidant mixture 1003.

Generating the low temperature plasma can include generating and outputting oxygen radicals. Generating the low temperature plasma can include ejecting electrons from one or more electrodes of the plasma generator 1012.

In one embodiment, the plasma generator 1012 can output a high temperature plasma including a gaseous mixture of ions and electrons. The high temperature plasma can help ignite the combustion reaction 1004 when the combustion reaction 1004 is absent.

In one embodiment, the plasma generator 1012 includes a power source and multiple electrodes. The power source may drive the plasma generator 1012 to generate the plasma. The power source may include a pulsed power source that may be operated to output nanosecond pulses such that the plasma generator 1012 is driven to generate the low temperature plasma. The low temperature plasma may produce plasma enhanced ignition of the fuel and oxidant mixture 1003.

In one embodiment, the plasma generator 1012 includes a power source having first and second output terminals, and first and second plasma generation electrodes. The first and the second plasma generation electrodes are respectively operatively coupled to the first and the second output terminals. The power source and the first and the second plasma generation electrodes may be operable to cause a low temperature plasma to form within or adjacent to a selected location for the combustion reaction.

In one embodiment, the combustion system 1000a utilizes the combustion sensor 1008 and the controller 1010 to monitor the state of the combustion reaction 1004. The combustion sensor 1008 may be coupled to the controller 1010. The combustion sensor 1008 may sense one or more parameters indicative of the state of the combustion reaction 1004. The combustion sensor 1008 may pass sensor signals to the controller 1010. The controller 1010 may analyze the sensor signals with a signal analyzer in order to ascertain the condition of the combustion reaction 1004 based on the sensor signals. Accordingly, the controller 1010 can include the signal analyzer. Alternatively, the signal analyzer can be part of the combustion sensor 1008 separate from the controller 1010.

In one embodiment, the controller 1010 controls the operation of the plasma generator 1012 based on feedback from the combustion sensor 1008. If the sensor signals from the combustion sensor 1008 indicate that the combustion reaction 1004 is not stable, the controller 1010 may cause the plasma generator 1012 to generate the plasma in order to stabilize the combustion reaction 1004. The controller 1010 can be coupled to the power source. The controller 1010 can selectively control generation of the plasma by selectively controlling the power source responsive to the sensor signals.

In one embodiment, the fuel and oxidant source 502 imparts a swirling motion to the fuel and oxidant mixture 1003. The swirling motion may promote a swirl stabilized combustion reaction 1004 of the fuel and oxidant mixture 1003 at the selected combustion location 1006. The plasma generator 1012 can further stabilize the swirl stabilized combustion reaction 1004 at the selected combustion location 1006 by generating the plasma in the vicinity of the selected combustion location 1006.

In one embodiment, the combustion sensor 1008 is an electro-capacitive combustion sensor. The electro-capacitive combustion sensor 1008 can include a plurality of capacitive electrodes positioned to detect characteristics of the combustion reaction 1004 by sensing capacitance in a vicinity of the selected combustion location 1006.

In one embodiment, the combustion sensor 1008 includes a flame rod or an ultraviolet scanner.

In one embodiment, the plasma generator 1012 is configured to selectively generate a low temperature plasma and a high temperature plasma. The controller 1010 can cause the plasma generator to generate the high temperature plasma when the combustion reaction 1006 is not present, as indicated by the combustion sensor 1008. The high temperature plasma can help to ignite the combustion reaction 1006. The controller 1010 can cause the plasma generator 1012 to generate the low temperature plasma when the combustion reaction is present, as indicated by the combustion sensor 1008. The low temperature plasma can help stabilize the combustion reaction 1004. The combustion sensor 1008 may output signals indicating that the combustion reaction 106 would benefit from the low temperature plasma.

In an embodiment, an electro-capacitive combustion sensor and a plasma generator may be operated in a time-sequenced "ping-pong" approach such that the plasma generator does not interfere with the combustion sensor when the combustion sensor is operated. Turning off the combustion sensor when the plasma generator is operated may further reduce possible failure modes where the plasma might short circuit energy to ground through the sensor electrode(s).

Figure 10B:
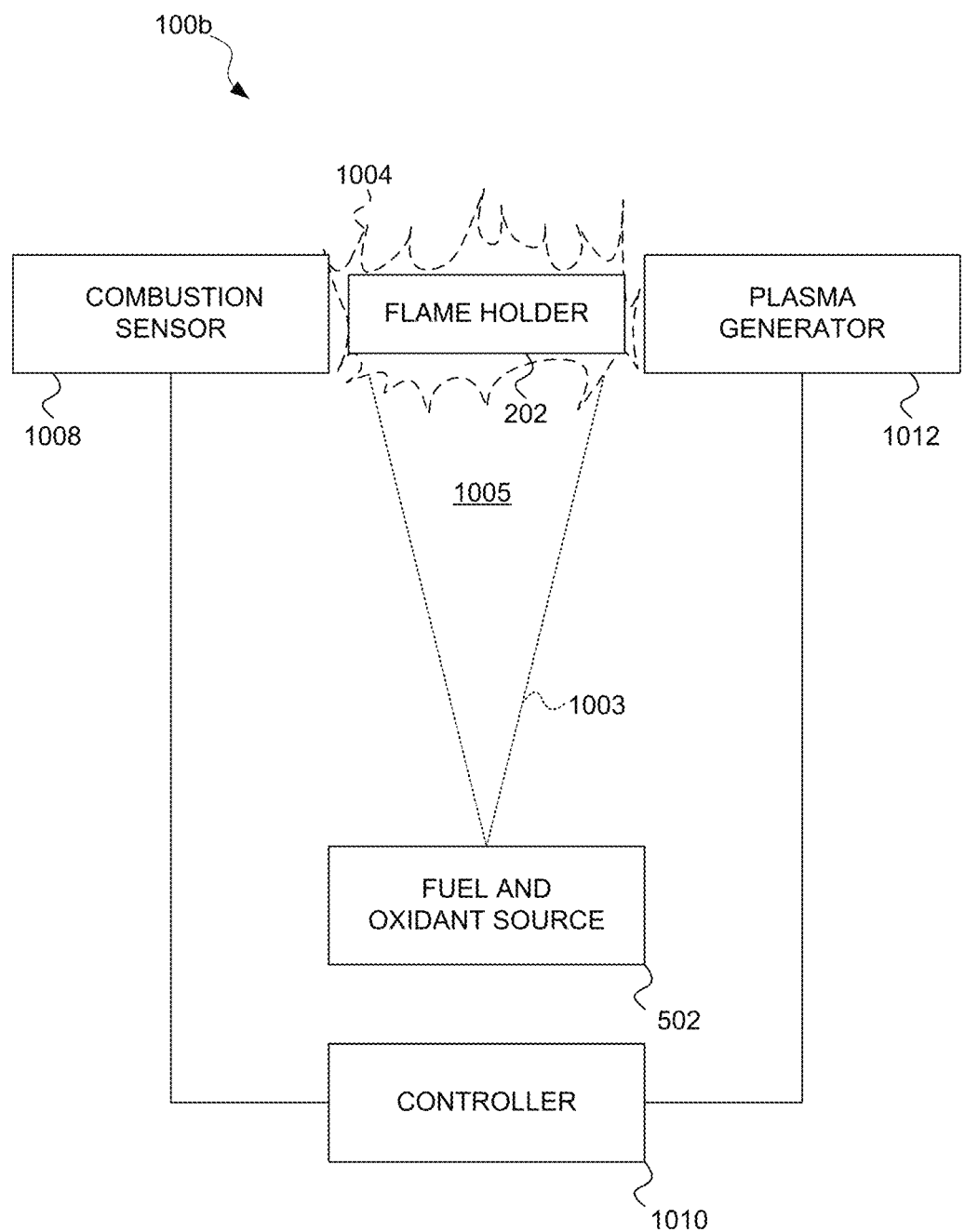
FIG. 10B is a block diagram of a combustion system including a plasma generator, a combustion sensor, and a perforated flame holder, according to an embodiment.

FIG. 10B is a block diagram of a combustion system 1000b, according to an embodiment. The combustion system 1000b may include a fuel and oxidant source 502 configured to output fuel and oxidant into a furnace volume, a flame holder 202 positioned within the furnace volume 1005. The flame holder 202 may be aligned to receive the fuel and oxidant mixture 1003 from the fuel and oxidant source 502 and to hold a combustion reaction 1004 of the fuel and oxidant mixture 1003. The combustion system 1000b includes a combustion sensor 1008 including one or more sensor electrodes positioned adjacent to the flame holder 202 and configured to sense the combustion reaction 1004 at the flame holder 202. The combustion system 1000b includes a low temperature plasma generator positioned at least partially within the furnace volume and configured to stabilize the combustion reaction at the flame holder 202 by outputting a low temperature plasma in a vicinity of the flame holder 202. The combustion system 1000b includes a controller 1010 operatively coupled to the combustion sensor 1008 and a low temperature plasma generator 1012 and configured to receive sensor signals from the combustion sensor 1008 indicative of a condition of the combustion reaction 1004.

In one embodiment, the plasma generator 1012 is positioned adjacent to the flame holder 202. The plasma generator 1012 may help to stabilize the combustion reaction 1004 held by the flame holder 202. The plasma generator 1012 can help to stabilize the combustion reaction 1004 by generating the plasma in the vicinity of the combustion reaction 1004. The plasma can energize the mixture of fuel and oxidant 1003 to promote stable combustion of the fuel and oxidant mixture 1003. For example, if the combustion reaction 1004 is unstable at the flame holder 202, the plasma generator 1012 can generate the plasma to energize the fuel and oxidant mixture 1003 to promote stable combustion of the fuel and oxidant mixture 1003.

In one embodiment, the combustion sensor 1008 is positioned adjacent to the flame holder 202. The combustion sensor 1008 may be positioned to detect one or more parameters indicative of the combustion reaction 1004 held by the flame holder 202. The combustion sensor 1008 may output sensor signals to the controller 1010 indicative of characteristics of the combustion reaction 1004 held by the flame holder 202.

In one embodiment, the combustion sensor 1008 detects whether the combustion reaction 1004 is held by the flame holder 202. In one embodiment, the combustion sensor 1008 detects whether the combustion reaction 1004 held by the flame holder 202 is stable. Instability of the combustion reaction 1004 can correspond to the combustion reaction 1004 having a temperature outside an expected range. Instability of the combustion reaction 1004 can correspond to the combustion reaction 1004 not being present at the flame holder 202, such as if the combustion reaction 1004 is present upstream from the flame holder 202, or too far downstream from the flame holder 202. In one embodiment, instability of the combustion reaction 1004 can correspond to the combustion reaction 1004 being entirely absent from the furnace volume 1005.

In one embodiment, the controller 1010 controls the plasma generator 1012 responsive to the sensor signals output by the combustion sensor 1008. In particular, the controller 1010 can cause the plasma generator 1012 to generate the plasma to assist in stabilizing the combustion reaction 1004 responsive to the sensor signals indicating instability or other abnormal or undesired parameters of the combustion reaction 1004.

In one embodiment, the flame holder 202 is a perforated flame holder 202 including a plurality of perforations extending between an input surface proximal to the fuel and oxidant source 502 and an output surface distal from the fuel and oxidant source 502. The perforated flame holder 202 can be configured to hold the combustion reaction 1004 at least partially within the perforations of the perforated flame holder 202.

In one embodiment, the flame holder 202 is a bluff body flame holder. The bluff body flame holder 202 can include one or more bluff bodies configured to receive the fuel and oxidant mixture 1003 and to hold the combustion reaction 1004. In another embodiment, the flame holder 202 may include a gutter. In embodiments, the flame holder 202 may be fueled such that the flame holder 202 includes a distal pilot burner. In another embodiment, the flame holder 202 may include a swirler positioned to add swirl to the fuel and oxidant mixture 1003 such that the swirl caused the combustion reaction to be positioned at the desired location 1006.

Figure 11A:
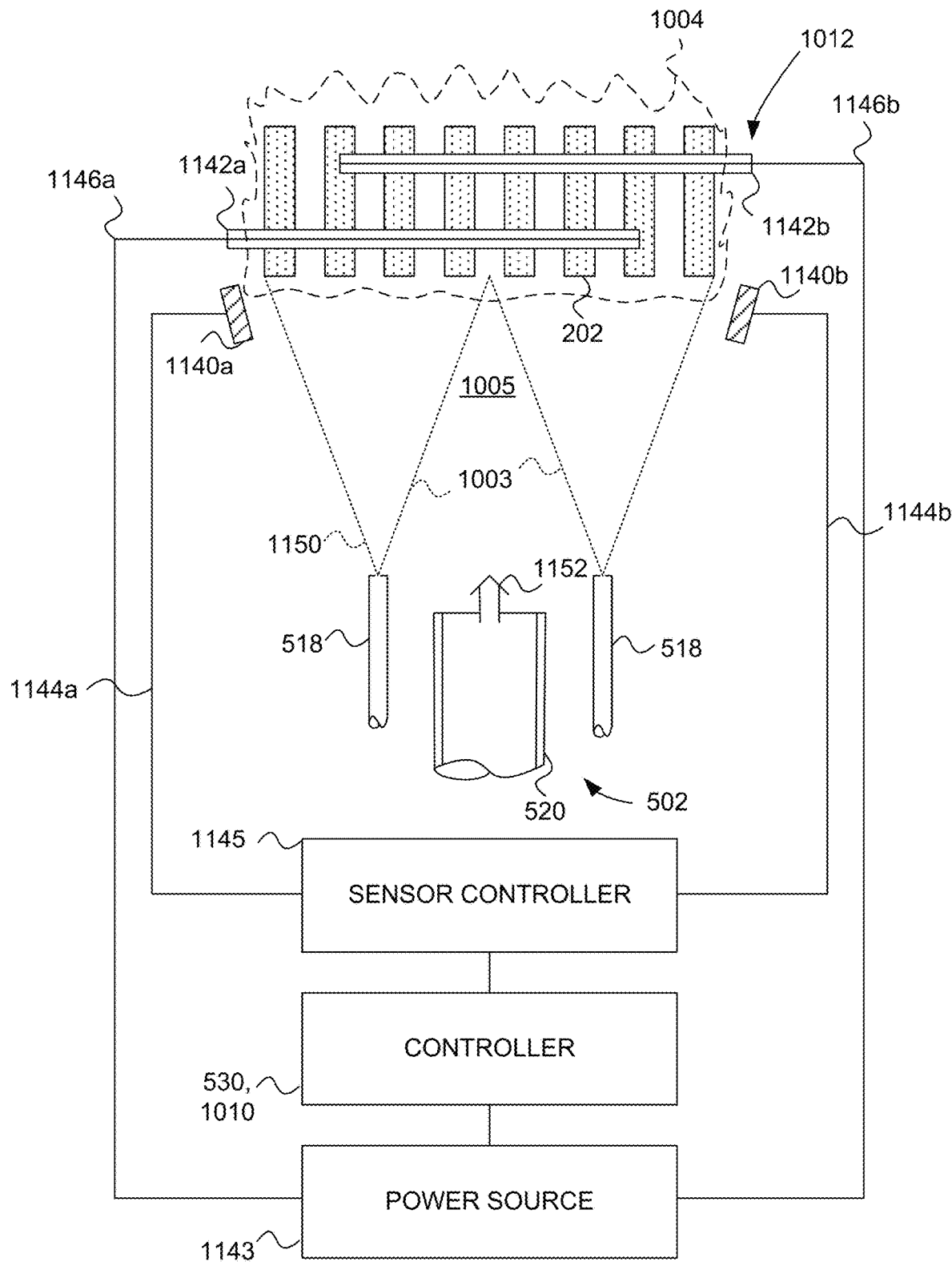
FIG. 11A is a diagram of a combustion system, according to an embodiment.

FIG. 11A is a diagram of a combustion system 1100a, according to an embodiment. The combustion system 1100a includes the fuel and oxidant source 502, a perforated flame holder 202, a plasma generator 1012, a combustion sensor 1008, a sensor controller 1145, and a controller 530, 1010. Specific attributes of the controller 530, 1010, which may be referenced by either number, may vary according to embodiment as selected according to application requirements. The components of the combustion system 1100a work together to support a stable combustion reaction 1004 held by the perforated flame holder 202.

In one embodiment, the fuel and oxidant source 502 includes one or more fuel nozzles 518 and an oxidant source 520. The one or more fuel nozzles 518 output a fuel 1150 into the furnace volume 1005 toward the perforated flame holder 202. The oxidant source 520 outputs an oxidant 1152 into the furnace volume 1005. The fuel 1150 and the oxidant 1152 mix together to form the fuel and oxidant mixture 1003 as they travel toward the perforated flame holder 202. The oxidant 1152 may essentially consist of air, and may be referred to as combustion air. The combustion air 1152 may be natural draft or may be delivered from a blower, for example.

In one embodiment, the perforated flame holder 202 is aligned to receive the fuel and oxidant mixture 1003. The perforated flame holder 202 is configured to hold a combustion reaction 1004 of the fuel and oxidant mixture 1003.

In one embodiment, it is possible that the combustion reaction 1004 can become unstable. Accordingly, the plasma generator 1012 is configured to generate a low temperature plasma in the vicinity of the perforated flame holder 202. The low temperature plasma can energize the fuel and oxidant mixture 1003 in order to stabilize the combustion reaction 1004 held by the perforated flame holder 202.

In one embodiment, the low temperature plasma generator 1012 includes one or more first plasma generation electrodes 1142a, one or more second plasma generation electrodes 1142b, the power source 1143, one or more first conductive leads 1146a, and one or more second conductive leads 1146b. The one or more first conductive leads 1146a couple the one or more first plasma generation electrodes 1142a to the power source 1143. The one or more second conductive leads 1146b couple the one or more second plasma generation electrodes 1142b to the power source 1143. Optionally, the power source 1143, one or more first and second conductive leads 1146a, 1146b, and one or more first and second plasma generation electrodes 1142a, 1142b may operate in a DC or pulsed DC mode, wherein polarity is maintained, or in a pulsed bipolar mode wherein polarity is switched.

In one embodiment, the power source 1143 causes the first and the second plasma generation electrodes 1142a, 1142b to generate a low temperature plasma in the vicinity of the perforated flame holder 202. The power source 1143 drives the first and the second plasma generation electrodes 1142a, 1142b to generate a low temperature plasma. The power source 1143 may be operated to output nanosecond pulses to the first and the second plasma generation electrodes 1142a, 1142b via the first and the second conductive leads 1146a, 1146b in order to generate the low temperature plasma. The low temperature plasma may produce plasma-enhanced ignition of the fuel and oxidant mixture 1003 at the perforated flame holder 202.

In one embodiment, at least one of the first and the second plasma generation electrodes 1142a, 1142b may be disposed adjacent to or within the perforated flame holder 202. The power source 1143 and the first and the second plasma generation electrodes 1142a, 1142b can be operated to cause a low temperature plasma to form within or adjacent to the perforated flame holder 202, according to an embodiment. The low temperature plasma may be capable of stabilizing a combustion reaction 1004 held by the perforated flame holder 202.

According to an embodiment, the low temperature plasma may have a temperature too low to ignite the fuel and oxidant mixture 1003 but may have sufficient energy to maintain ignition of the fuel and oxidant mixture 1003.

Figure 12:
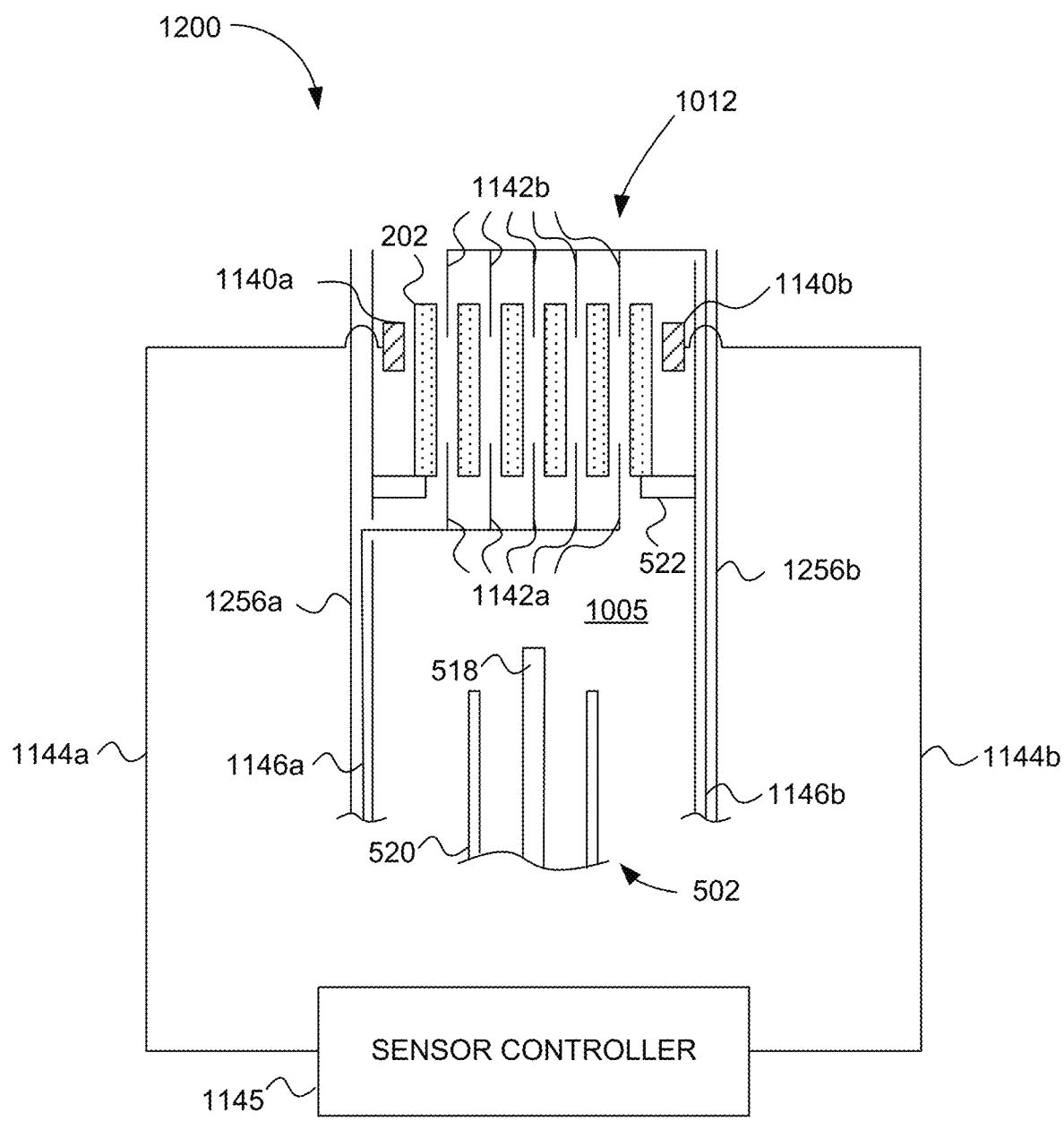
FIG. 12 illustrates a combustion system, according to an embodiment.

Referring to FIG. 12, according to an embodiment, the perforated flame holder 202 may be supported by a support structure 203, 522 (see FIGS. 2 and 5). The perforated flame holder support structure 522 may include a ceramic material (for example, silicon carbide). The perforated flame holder support structure 522 may include at least two hollow support legs 1256a, 1256b (see FIGS. 12 and 20), according to an embodiment. The first and the second conductive electrical leads 1146a, 1146b may be respectively routed from the power source 1143 to the first and the second plasma generation electrodes 1142*a*, 1142*b* through the hollow support legs 1256*a*, 1256*b* of the perforated flame holder support structure 522. In an embodiment, the bottom ends of the hollow support legs 1256*a*, 1256*b* may be open to receive cooling airflow. The hollow support legs 1256*a*, 1256*b* may protect the first and the second conductive electrical leads 1146*a*, 1146*b* from high operating temperatures in the furnace volume 1005.

In another embodiment, a conventional bluff body flame holder may be substituted for a perforated flame holder 202.

Figure 11B:
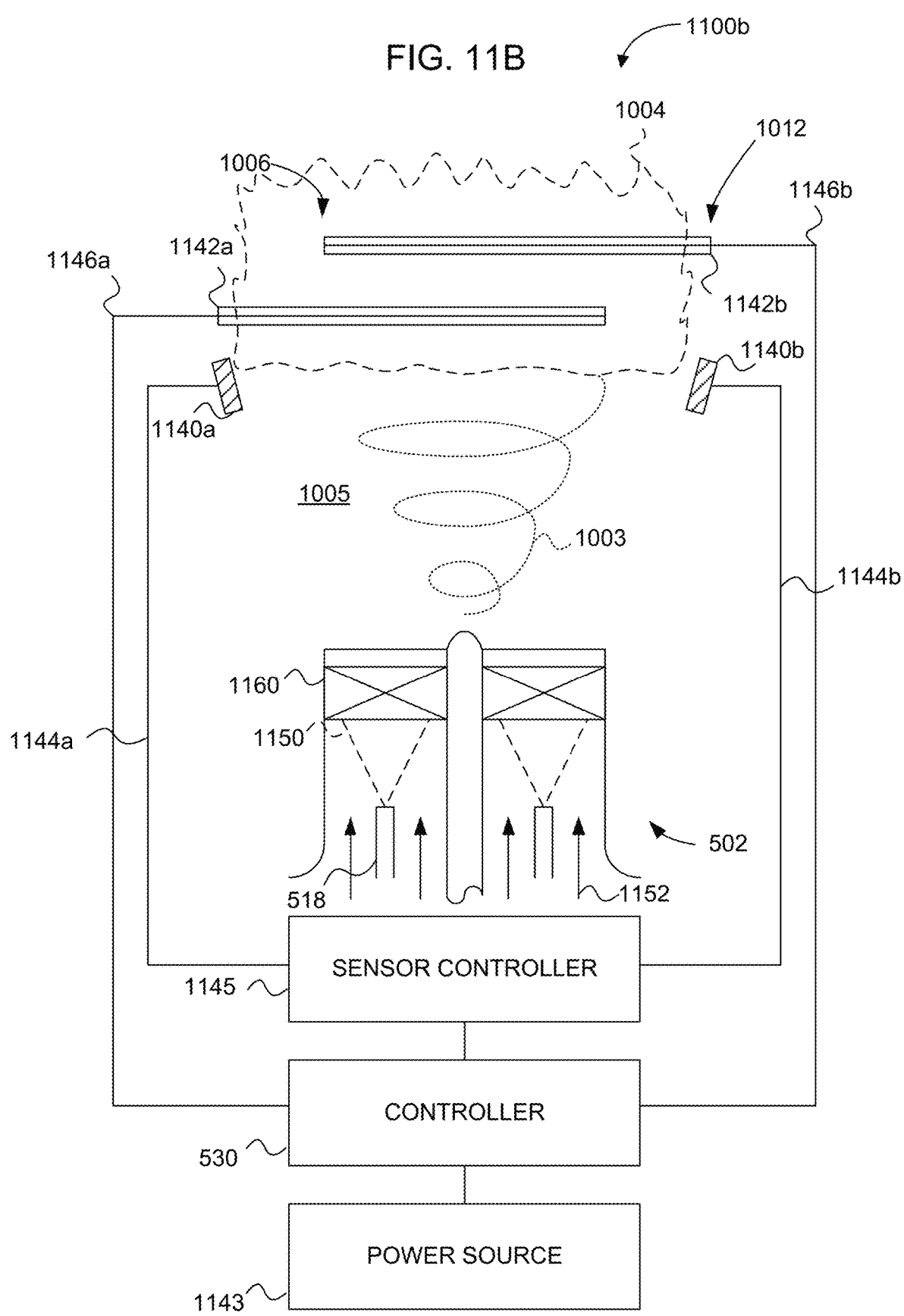
FIG. 11B is a diagram of a combustion system, according to an embodiment.

In one embodiment, the first and the second plasma generation electrodes 1142*a*, 1142*b* may be arranged to form a gap in a direction parallel to combustion fluid flow, as shown in FIGS. 11A, 11B and 12. In another embodiment, the first and the second plasma generation electrodes 1142*a*, 1142*b* may be arranged to form a gap in a direction perpendicular to combustion fluid flow (e.g., see FIGS. 13, 14, and 15).

In one embodiment, the combustion sensor 1008 includes a first sensor electrode 1140*a*, a second sensor electrode 1140*b*, a sensor controller 1145, a first sensor lead 1144*a*, and a second sensor lead 1144*b*. The first sensor lead 1144*a* couples the first sensor electrode 1140*a* to the sensor controller 1145. The second sensor lead 1144*b* couples the second sensor electrode 1140*b* to the sensor controller 1145.

In one embodiment, the first and the second sensor electrodes 1140*a*, 1140*b* are aligned such that a straight line or a fringing field between centers of the first and the second sensor electrodes 1140*a*, 1140*b* passes through an intended combustion location 1006, such as through a perforated flame holder 202. In one embodiment, the first and the second sensor electrodes 1140*a*, 1140*b* are aligned such that a signal emitted from the first sensor electrode 1140*b* and received by the second sensor electrode 1140*b* passes through a flame held by the perforated flame holder 202, according to an embodiment. The first and the second sensor electrodes 1140*a*, 1140*b* and the controller 502 may be configured to cooperate to measure the presence or absence of the combustion reaction 1004 held by the perforated flame holder 202, or to sense other parameters of the combustion reaction 1004. In one embodiment, the first and the second sensor electrodes 1140*a*, 1140*b* and the sensor controller 1145 are configured to cooperate to measure a combustion reaction characteristic including the presence or absence of the flame held by the perforated flame holder. The sensor controller 1145 can be configured to output the sensor signals to the controller 502. The combustion sensor 1008 can be useful for ensuring that combustion system parameters (e.g., fuel flow rate, oxidant flow rate, and heating) are balanced sufficiently to keep the flame within the perforated flame holder 202. Other flame sensing technologies have shown themselves to be less effective for this purpose.

In one embodiment, the sensor controller 1145 receives sensor signals from the first and the second sensor electrodes 1140*a*, 1140*b*. The sensor signals indicate one or more parameters or characteristics of the combustion reaction 1004. The sensor controller 1145 analyzes the sensor signals and determines whether the combustion reaction 1004 is stable. The sensor controller 1145 passes sensor signals or sensor data to the controller 502.

In one embodiment, the sensor controller 1145 is part of the controller 502. Alternatively, the sensor controller 1145 can be separate from and communicatively coupled to the controller 502.

In one embodiment, the controller 502 controls the plasma generator 1012 responsive to the sensor signals from the combustion sensor 1008. The controller 502 can control the plasma generator 1012 to generate plasma in the vicinity of the perforated flame holder 202 in order to stabilize the combustion reaction 1004 if the sensor signals indicate that the combustion reaction 1004 is not stable.

In one embodiment, the controller 502 controls the plasma generator 1012 by controlling the power source 1143. The controller 502 can control the power source 1143 to cause the first and the second plasma generation electrodes 1142*a*, 1142*b* to generate the low temperature plasma in the vicinity of, and even within, the perforated flame holder 202 in order to stabilize the combustion reaction 1004.

In one embodiment, the combustion sensor 1008 is an electro-capacitive combustion sensor. In an embodiment, the combustion sensor 1008 includes one or more pairs of sensor electrodes 1140 positioned adjacent to the flame holder 202 and configured to sense parameters of the combustion reaction by sensing capacitance between each of the one or more pairs of sensor electrodes 1140 in a vicinity of the flame holder 202. The controller 502 detects the capacitance between the first and the second sensor electrodes 1140*a*, 1140*b*. The controller 502 determines whether the combustion reaction 1004 is stable, or indeed present, based on the capacitance between the first and the second sensor electrodes 1140*a*, 1140*b*.

In one embodiment, the first and the second sensor electrodes 1140*a*, 1140*b* can be positioned differently than shown in FIGS. 11A, 11B. In one embodiment, the first and the second sensor electrodes 1140*a*, 1140*b* can be positioned such that an intended flame position 1006, such as a perforated flame holder 202 is directly in between the first and the second sensor electrodes 1140*a*, 1140*b*. In one embodiment, the first and the second sensor electrodes 1140*a*, 1140*b* can be positioned slightly above the perforated flame holder 202. In one embodiment, the first and the second sensor electrodes 1140*a*, 1140*b* can be positioned slightly below the perforated flame holder 202.

According to an embodiment, the combustion sensor 1008 can include a plurality of tiers of sensor electrodes 1140 positioned at selected locations adjacent to the perforated flame holder 202. Each pair of sensor electrodes 1140 may include a first sensor electrode 1140*a* and a second sensor electrode 1140*b*. The controller 502 may make tomographic images of the perforated flame holder 202 based on the capacitance between the pairs of sensor electrodes 640. The images represent slices of the perforated flame holder 202 based on the capacitances between the pairs of sensor electrodes 1140. The capacitance between pairs of sensor electrodes 1140 depends, in part, on the dielectric constant of the material(s) between the pairs of sensor electrodes 1140. In particular, the dielectric constant within the perforations 510 of the perforated flame holder 202 can change based on the characteristics of the combustion reaction 1004 within the perforations 510. Therefore, the images produced based on the capacitances between the pairs of sensor electrodes 1140 can give an indication of a combustion reaction within the perforations 510 or a concentration or flow of the fuel, the oxidant, and the flue gasses at various locations in the perforated flame holder 202 based on the dielectric constant at the various locations of the perforated flame holder 202. The control circuit 502 can analyze the images and can control the plasma generator 1012 to generate plasma to stabilize the combustion reaction 1004 responsive to the electro-capacitive tomography images generated from the pairs of sensor electrodes 1140.

In one embodiment, each pair of sensor electrodes 1140 includes two sensor electrodes 1140 generally facing each other, with the perforated flame holder 202 positioned between the pair of sensor electrodes 1140. The control circuit 502 controls each pair of sensor electrodes 1140 to make a plurality of images of the perforated flame holder 202, according to an embodiment.

In one embodiment, the plurality of sensor electrodes 1140 includes one or more first pairs of sensor electrodes 1140 facing each other in a first orientation substantially perpendicular to a primary direction of a flow of the fuel and oxidant mixture 1003 toward the perforated flame holder 202. The first pairs of sensor electrodes 1140 sense the capacitance of the perforated flame holder 202 along an X direction substantially perpendicular to a primary direction of the flow of the fuel and oxidant mixture 1003 toward the perforated flame holder 202. The primary direction of the flow of the fuel and oxidant mixture 1003 toward the perforated flame holder 202 can correspond to a Z direction.

In one embodiment, the plurality of sensor electrodes 1140 includes one or more second pairs of sensor electrodes 1140 facing each other in a second orientation substantially perpendicular to the first orientation and the primary direction of the flow of the fuel and oxidant mixture 1003 toward the perforated flame holder 202. The second pairs of sensor electrodes 1140 sense the capacitance of the perforated flame holder 202 along a Y direction substantially perpendicular to the primary direction of the flow of the fuel and oxidant mixture 1003 and substantially perpendicular to the orientation of the first pairs of sensor electrodes 1140.

In one embodiment, the plurality of sensor electrodes 1140 can include pairs of sensor electrodes 1140 oriented transverse to both the first pairs of sensor electrodes 1140 and the second pairs of sensor electrodes 1140.

In one embodiment, the combustion system 1100a does not include the first and the second plasma generation electrodes 1142a, 1142b. In another embodiment, the combustion system 1100a does not include the sensor electrodes 1140.

According to an embodiment, the plasma generator 1012 includes an electrical power source having first and second output terminals and first and second plasma generation electrodes 1142a, 1142b, respectively operatively coupled to the first and the second output terminals. The electrical power source and the first and the second plasma generation electrodes 1142a, 1142b may be operable to cause a high temperature plasma to form within or adjacent to a selected location for the combustion reaction. The electrical power source can include the radiofrequency pulse power source 1143. The electrical power source can be the radiofrequency pulse power source 1143.

According to one embodiment, the controller is 502 configured to cause the electrical power source and the first and the second plasma generation electrodes 1142a, 1142b to cooperate to cause the high temperature plasma to form when the controller 502 determines that a combustion reaction is absent within the furnace volume. In another embodiment, the controller 502 is configured to cause the electrical power source and the first and the second plasma generation electrodes 1142a, 1142b to cooperate to cause a low temperature plasma to form when the controller determines that a combustion reaction is present within the furnace volume. The controller 502 may be configured to cause the electrical power source and the first and the second plasma generation electrodes 1142a, 1142b to cooperate to cause a low temperature plasma to form when the controller 502 determines that a combustion reaction is present but unstable within the furnace volume.

In one embodiment, the plasma generator 1012 includes a low temperature plasma generator. The low temperature plasma generator includes a plasma generator also configured to generate a high temperature plasma. The controller 502 may be configured to cause the plasma generator to generate a high temperature plasma responsive to sensor signals indicative of combustion reaction non-ignition. The controller 502 may be configured to cause the plasma generator to generate a high temperature plasma responsive to sensor signals indicative of combustion reaction blowout.

In one embodiment, the plasma generator 1012 is configured to selectively generate both a low temperature plasma and a high temperature plasma.

In one embodiment, the power source 1143 is a pulsed power source. In one embodiment, the pulsed power source 1143 is operable to output nanosecond electrical pulses having a duration of between 1000 picoseconds and 300 nanoseconds. In one embodiment, the pulsed power source 1143 is operable to output at least 10 kilovolt nanosecond electrical pulses. In one embodiment, the pulsed power source 1143 is operable to output about 30 kilovolt nanosecond electrical pulses. In one embodiment, the pulsed power source 1143 is operable to output nanosecond electrical pulses at a duty cycle of between 1% and 50%. In one embodiment, the pulsed power source 1143 is operable to output pulses at a rate of 10 kilohertz to 100 kilohertz. In one embodiment, the pulsed power source 1143 is a radio frequency pulsed power source.

In one embodiment, the combustion sensor 1008 further includes an amplifier operatively coupled to the first sensor electrode 1140a. The amplifier is capable of outputting a 15 volt peak-to-peak signal. The combustion sensor 1008 was configured to output 15 volt peak-to-peak voltage from the first sensor electrode 1140a in one configuration. The inventors contemplate that the combustion sensor 1008 may be configured to use a somewhat higher voltage to measure combustion in a larger or longer range system.

FIG. 11B is an illustration of a combustion system 1100b, according to an embodiment. The combustion system 1100b includes a swirler 1160 as part of the the fuel and oxidant source 502 that forms a swirl stabilized combustion reaction 1004 at a selected combustion location 1006.

In one embodiment, the fuel and oxidant source 502 includes one or more swirlers 1160. The fuel and oxidant source 502 outputs the fuel 1150 and the oxidant 1152 upstream from the swirler 1160. The fuel 1150 and the oxidant 1152 pass through the swirler 1160. The swirler 1160 imparts a swirling motion to the fuel 1150 and the oxidant 1152. The swirling fuel 1150 and the swirling oxidant 1152 mix together to form the fuel and oxidant mixture 1003. The fuel and oxidant mixture 1003 has a swirling motion as the fuel and oxidant mixture 1003 travels toward the selected combustion location 1006. The swirling fuel and oxidant mixture 1003 support a swirl stabilized combustion reaction 1004 at the selected combustion location 1006. Those of skill in the art will recognize, in light of the present disclosure, that other mechanisms and schemes for imparting a swirling motion to one or both of the fuel 1150 and the oxidant 1152 may be implemented without departing from the scope of the present disclosure.

In one embodiment, a combustion system 1100b includes a fuel and oxidant source 502 configured to output a swirling mixture of fuel and oxidant within a furnace volume. The combustion system 1100b includes an electro-capacitive combustion sensor including one or more electrodes positioned within the furnace volume and configured to sense a combustion reaction of the fuel and the oxidant at a selected combustion location 1006. The combustion system 1100*b* includes a plasma generator positioned at least partially within the furnace volume and configured to stabilize the combustion reaction location 1006 by outputting a plasma. The combustion system 1100*b* includes a controller operatively coupled to the electro-capacitive combustion sensor and the plasma generator and configured to receive sensor signals from the electro-capacitive combustion sensor indicative of a condition of the combustion reaction and to control operation of the plasma generator to generate a low temperature plasma or to generate a high temperature plasma responsive to the sensor signals. In an embodiment, the fuel and oxidant source includes a swirler.

In one embodiment, a combustion system 1100*b* includes a fuel and oxidant source 502 configured to output a swirling mixture of fuel and oxidant toward a selected combustion location 1006 within a furnace volume. The combustion system 1100*b* includes an electro-capacitive combustion sensor including a first sensor electrode, and a second sensor electrode. The first and the second sensor electrodes may be aligned such that a straight line or a fringing field between the first and the second sensor electrodes passes through the selected combustion location 1006. The combustion system 1100*b* includes a low temperature plasma generator including first and second plasma generation electrodes positioned within the selected combustion location 1006. The low temperature plasma generator may be configured to stabilize the combustion reaction at the selected combustion location 1006 by generating, with the first and the second plasma generation electrodes, a low temperature plasma within or adjacent to the selected combustion location 1006. The combustion system 1100*b* includes a controller operatively coupled to the electro-capacitive combustion sensor and the low temperature plasma generator and configured to receive sensor signals from the first and the second sensor electrodes indicative of a condition of the combustion reaction and to control operation of the low temperature plasma generator responsive to the sensor signals.

In one embodiment, a combustion system includes a main fuel source configured to output a fuel stream, and an oxidant source configured to output an oxidant to mix with the fuel stream. The combustion system includes a flame sensor including a first sensor electrode, a second sensor electrode, and a sensor controller respectively coupled to the first and the second sensor electrodes via first and second electrical leads. The first and the second sensor electrodes and the sensor controller may be configured to cooperate to measure the presence or absence of a flame supported by a mixture of the fuel stream and the oxidant. The burner system may optionally include a perforated flame holder aligned to receive the mixture of fuel and oxidant, and configured to hold the flame supported by the fuel and the oxidant. The first and the second sensor electrodes and the sensor controller are configured to cooperate to measure the presence or absence of the flame held by the perforated flame holder.

In one embodiment, a burner system includes a main fuel source configured to output a fuel stream, and an oxidant source configured to output an oxidant to mix with the fuel stream. The burner system includes a flame sensor including a first sensor electrode, a second sensor electrode, and a sensor controller respectively coupled to the first and the second sensor electrodes via first and second electrical leads. The first and the second sensor electrodes and the sensor controller may be configured to cooperate to measure the presence or absence of a flame supported by a mixture of the fuel stream and the oxidant. In an embodiment, the burner system further includes a perforated flame holder aligned to receive the mixture of the fuel stream and the oxidant, and configured to hold the flame supported by the fuel and the oxidant. The first and the second sensor electrodes and the sensor controller are configured to cooperate to measure the presence or absence of the flame held by the perforated flame holder. In an embodiment, the first and the second sensor electrodes are aligned adjacent to the perforated flame holder.

In one embodiment, the plasma generator 1012, the combustion sensor 1008, and the controller 502 operate to stabilize the combustion reaction 1004 as described above in relation to FIG. 11A. In particular, the controller 502 controls the plasma generator 112 to generate plasma responsive to sensor signals provided by the combustion sensor 108 in order to stabilize the combustion reaction 1004.

FIG. 12 illustrates a combustion system 1200 including another arrangement of the first and the second plasma generation electrodes 1142*a*, 1142*b* aligned to form gaps in a direction parallel to the combustion fluid flow, according to an embodiment. The tips of opposing electrodes 1142 may be aligned across a discharge gap (in a manner akin to a bed of nails). The first and the second plasma generation electrodes 1142*a*, 1142*b* may be corona electrodes or dielectric barrier discharge electrodes, for example.

Alternatively, the first and the second plasma generation electrodes 1142*a*, 1142*b* may be arranged to form gaps in a direction transverse to the combustion fluid flow.

In one embodiment, while FIG. 12 does not show the sensor controller 1145, the sensor controller 1145 may also be present as shown in FIG. 11A. Alternatively, the sensor controller 1145 may be part of the controller 1145. Additionally, though the power source 1143 is not shown in FIG. 12, the power source 1143 may also be present.

In one embodiment, the first and the second conductive leads 1146*a* and 1146*b* can be positioned within the hollow support legs 1256*a* and 1256*b* of the perforated flame holder support structure 522. Though not shown in FIG. 12, the first and the second sensor leads 1144*a*, 1144*b* may also be routed through the hollow support legs 1256*a*, 1256*a*, according to an embodiment.

Figure 13:
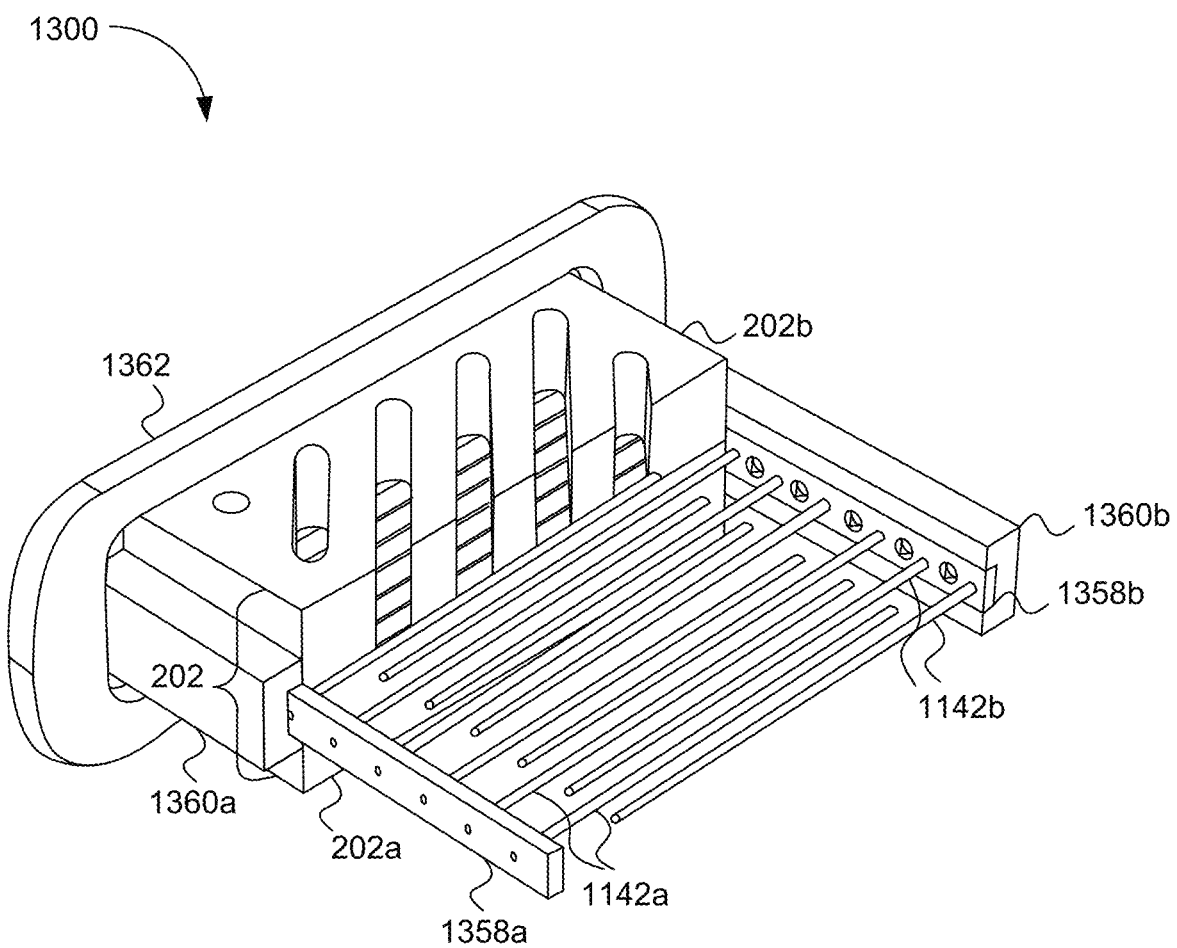
FIG. 13 is a view of a 3D model of a portion of a flame holder assembly, according to an embodiment.

FIG. 13 is a view of a 3D model 1300 of a portion of a perforated flame holder 202 assembly having transversely aligned first and second plasma generation electrodes 1142*a*, 1142*b*, according to an embodiment. The first and the second plasma generation electrodes 1142*a*, 1142*b* may be disposed within elongated holes formed in the perforated flame holder 202. The perforated flame holder 202 and the first and the second plasma generation electrodes 1142*a*, 1142*b* may be arranged in an assembly having the first and the second plasma generation electrodes 1142*a*, 1142*b* sandwiched between upstream and downstream perforated flame holder halves 202*a*, 202*b*. Additionally or alternatively, the first and the second plasma generation electrodes 1142*a*, 1142*b* may be respectively mechanically and electrically coupled to conductive rails 1358*a*, 1358*b*.

In an embodiment, the conductive rails 1358*a*, 1358*b* may be backed by ceramic blocks 1360*a*, 1360*b*. The ceramic blocks 1360*a*, 1360*b* and the upstream and the downstream perforated flame holder halves 202*a*, 202*b* may be clamped together by one or more ceramic clamps 1362. Preferably, the first and the second plasma generation electrodes 1142*a*, 1142*b* may be disposed across the lateral extent of the perforated flame holder 202. Additionally or alternatively, similar to the combustion system 1100*a* of FIG. 11A, the first and the second plasma generation electrodes 1142a, 1142b may be disposed within elongated holes formed in the perforated flame holder 202.

Figure 14:
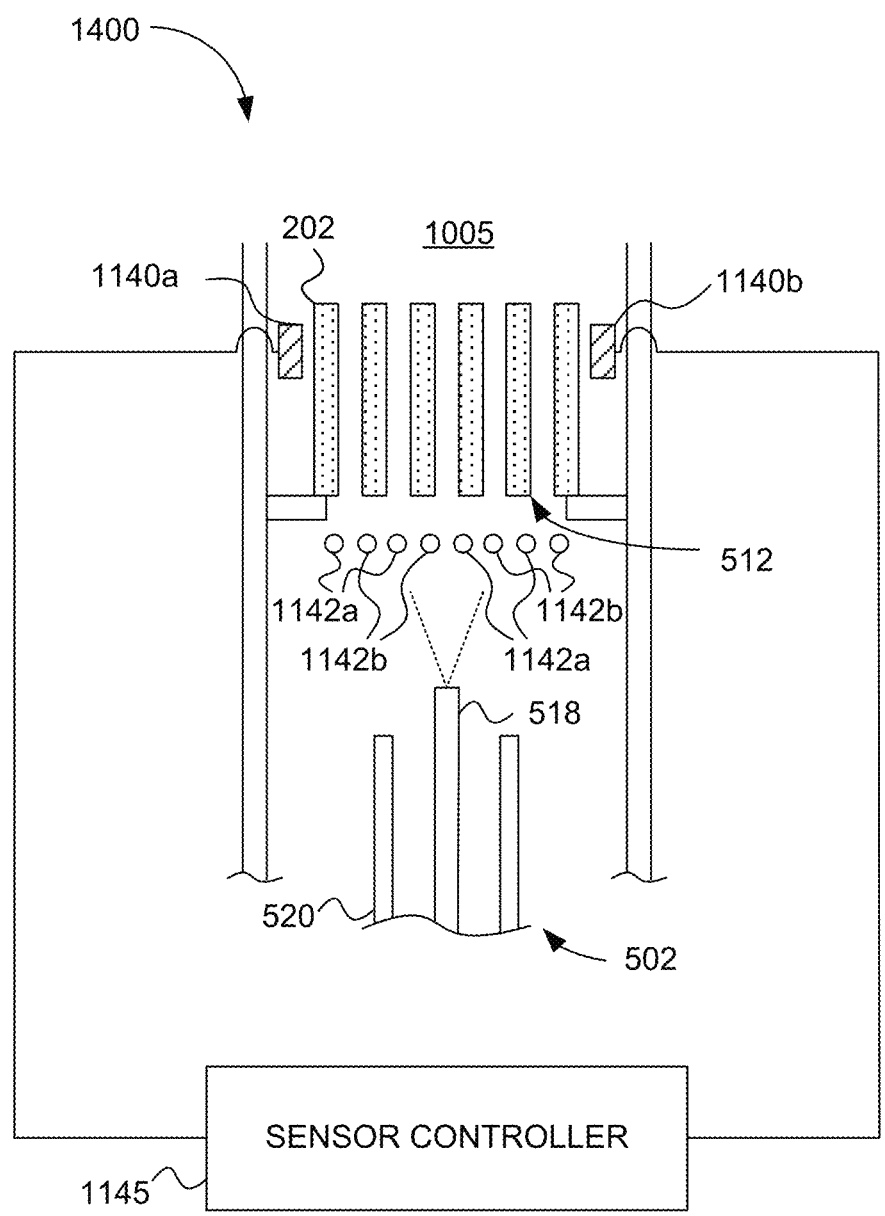
FIG. 14 illustrates a combustion system, according to an embodiment.

FIG. 14 illustrates a combustion system 1400 including another arrangement of the first and the second plasma generation electrodes 1142a, 1142b disposed adjacent to the input face 512 of the perforated flame holder 202.

Figure 15:
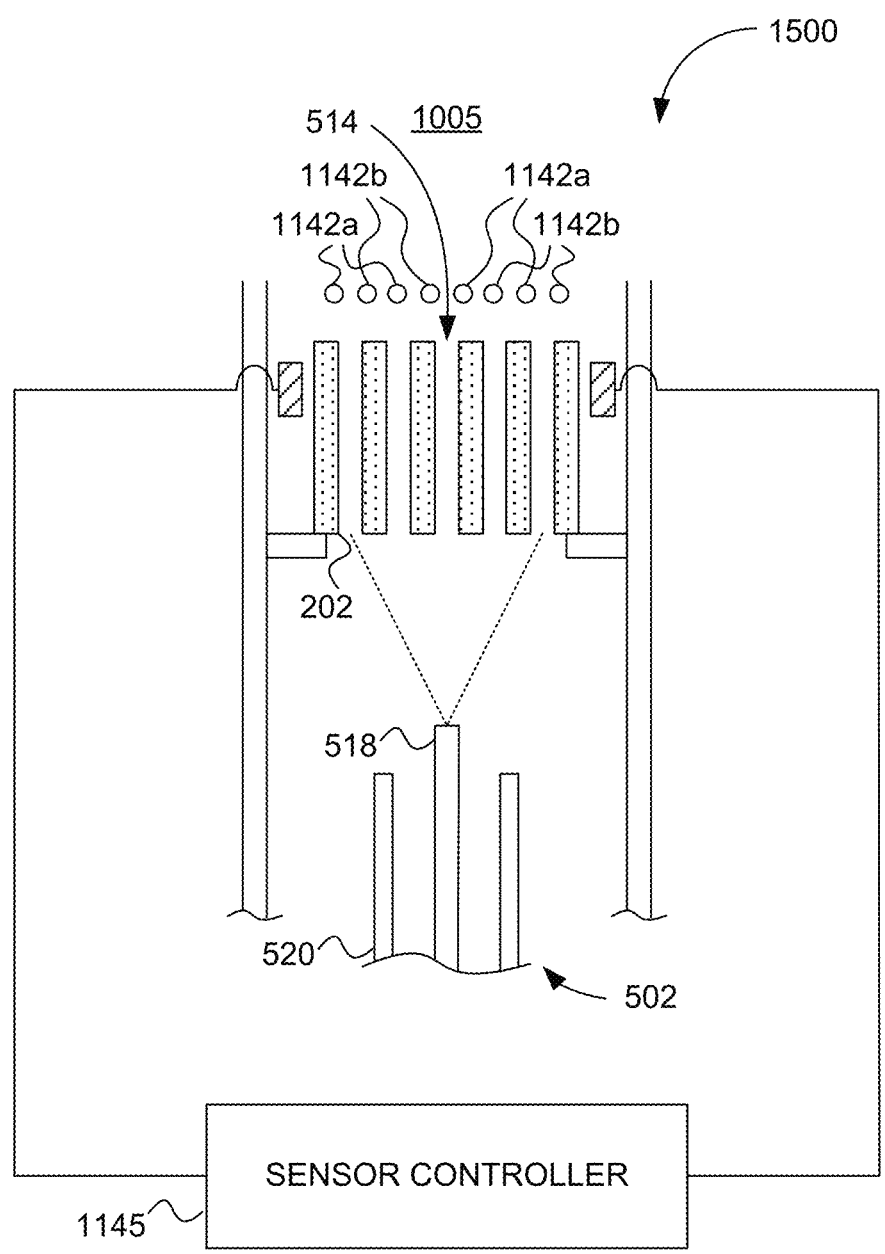
FIG. 15 illustrates a combustion system, according to an embodiment.

FIG. 15 illustrates a combustion system 1500 including another arrangement of the first and the second plasma generation electrodes 1142a, 1142b disposed adjacent to the output face 514 of the perforated flame holder 202.

Referring to FIGS. 11A-15, various compositions are contemplated for the first and the second plasma generation electrodes 1142a, 1142b. The first and the second plasma generation electrodes 1142a, 1142b may be formed at least partially from stainless steel or a superalloy, such as Hastelloy or Inconel.

According to an embodiment, the first and the second plasma generation electrodes 1142a, 1142b may be dielectric barrier discharge electrodes. The first and the second plasma generation electrodes 1142a, 1142b may include a plasma coated dielectric layer comprising zirconium oxide. The plasma coated dielectric layer may include a tie (adhesion enhancement) layer that includes titanium, molybdenum, chromium, aluminum, yttrium, nickel, and/or cobalt, for example. Alone or in combination, the tie layer material(s) may be formed or supplied in oxide form.

Figure 16A:
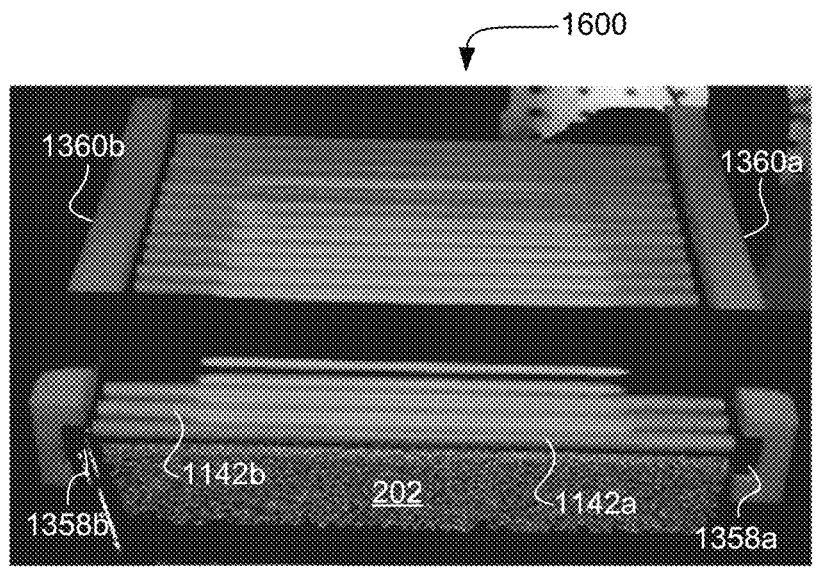
FIG. 16A and FIG. 16B are photographs showing a photonic discharge from dielectric barrier discharge electrodes, according to an embodiment.
Figure 16B:
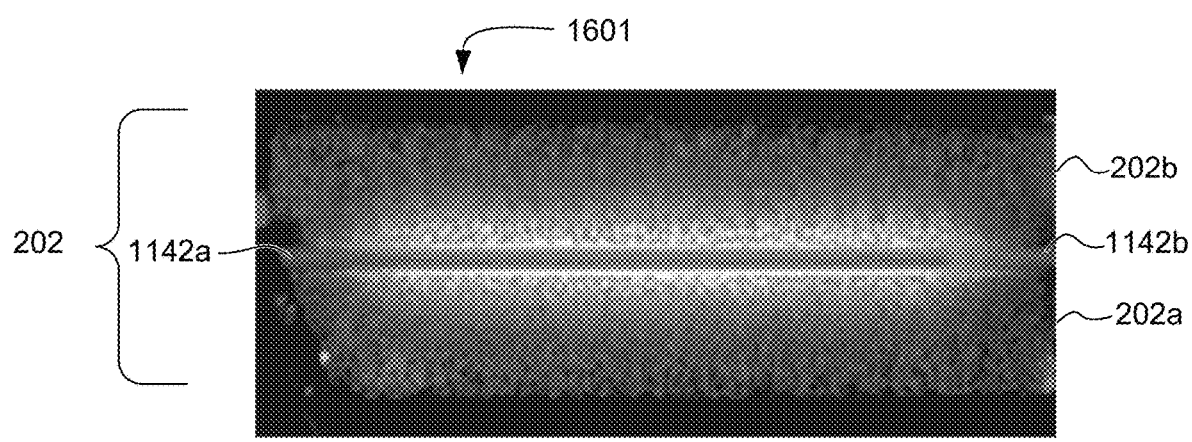

FIG. 16A and FIG. 16B are photographs 1600, 1601 showing a photonic discharge from the first and the second plasma generation electrodes 1142a, 1142b arranged as shown in FIG. 13. The first and second plasma generation electrodes can include dielectric barrier discharge electrodes. The first and the second plasma generation electrodes 1142a, 1142b were driven with approximately 150 watts (no more than 5 mA and between 10 kV-30 kV) with a radio frequency (kilohertz to megahertz) square wave on one electrode 1142a while holding the other electrode 1142b at ground. This frequency corresponds to vibrational excitation shown at the left end of FIG. 23. Alternatively, a chopped DC triangle wave can be used instead of a square wave.

Referring to FIG. 11A and FIG. 11B, the power source 1143 may be operated to output nanosecond pulses. The plasma responsively produced by the first and the second plasma generation electrodes 1142a, 1142b may produce plasma-enhanced ignition of the fuel and oxidant mixture 1003. The plasma-enhanced ignition may reduce a minimum stable fuel rate compared to the combustion systems 1100a, 1100b not using plasma enhanced ignition, such that a turndown ratio may be increased by 20% or more. The turndown ratio may be defined as a maximum stable fuel flow rate minus the minimum stable fuel flow rate divided by the maximum stable fuel flow rate. According to an embodiment, the turndown ratio may be increased from about 50% to about 60% or greater. In another embodiment, the turndown ratio may be increased by 30% or more.

The power source 1143 may operated to output nanosecond pulses such that a plasma responsively produced by the first and the second plasma generation electrodes 1142a, 1142b may produce plasma enhanced ignition of the fuel and oxidant mixture 1003. The plasma-enhanced ignition may reduce the maximum stable fuel rate compared to the combustion systems 1100a, 1100b not using plasma enhanced ignition, such that the turndown ratio may be increased by 5% or more. The turndown radio may be defined as the maximum stable fuel flow rate minus the minimum stable fuel flow rate, quantity divided by the maximum stable fuel flow rate. According to an embodiment, the turndown ratio may be increased by 10% or more. Alternatively, in another embodiment, the turndown ratio may be increased from about 50% to about 55% of greater.

Figure 17:
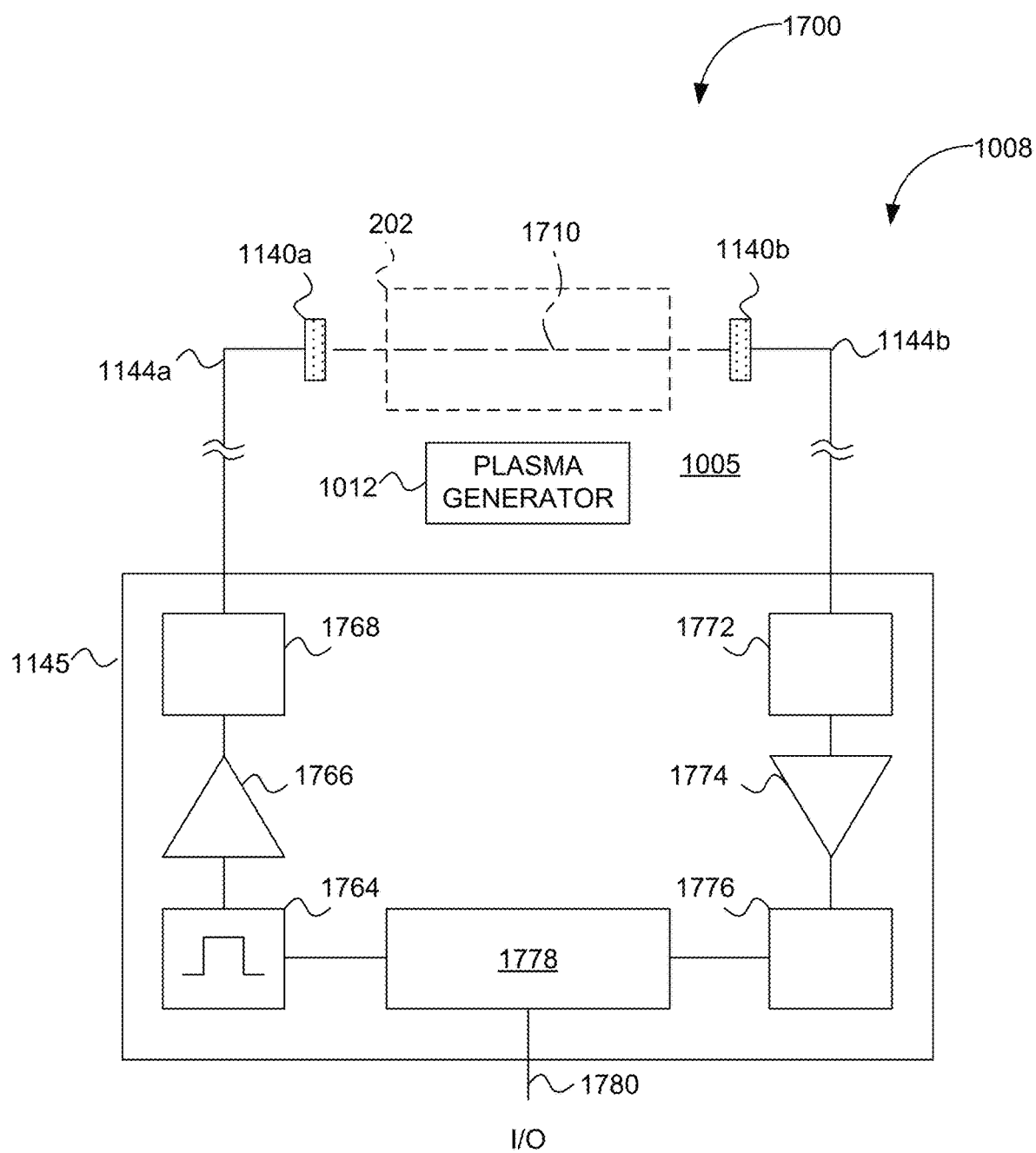
FIG. 17 is a diagram of a combustion system and combustion sensor, according to an embodiment.

FIG. 17 is a diagram of a combustion system 1700 including a combustion sensor 1008, according to an embodiment. The combustion sensor 108 may include a sensor controller 1145. The sensor controller 645 may include a waveform generator 1764 that may be configured to output a time-varying voltage. An amplifier 1766 (that can be inverting or non-inverting) may be operably coupled to the waveform generator 1764, and may be configured to amplify a logic-level voltage from the waveform generator 1764 to a broadcast voltage. In an embodiment, the broadcast voltage is formed as a sinusoidal waveform having a 15 volt peak-to-peak voltage. Smaller systems may operate at a lower voltage. Larger systems may operate at a higher voltage. An electrical filter 1768 may be operably coupled to the amplifier 1766, and may be configured to protect circuitry 1766, 1764, 1778, 1776, 1774 in the sensor controller 1145 from electrostatic discharge. The electrical filter 1768 may be operably coupled to the first sensor electrode 1140a via the first sensor electrical lead 1144a. The first sensor electrode 1140a may be configured to broadcast the amplified waveform to the second sensor electrode 1140b through a gap spanning a selected combustion location determined by a flame holder 202 as a broadcast signal, according to an embodiment. According to another embodiment, the first sensor electrode 1140a may be configured to broadcast the amplified waveform to the second sensor electrode 1140b through or adjacent to a gap spanning the selected location for the combustion reaction as a broadcast signal.

A second electrical filter 1772 (which may optionally be identical to the electrical filter 1768) may be operably coupled to the second sensor electrode 1140b via the second electrical lead 1144b, and may be configured to protect the circuitry 1774, 1776, 1778, 1764, 1766 from electrostatic discharge, according to an embodiment.

A second amplifier 1774 may be configured to raise a received voltage to a logic level voltage, according to an embodiment.

A receiver circuit 1776 may be operatively coupled to the second amplifier 1774, and may be configured to receive and digitize an amplified signal received by the second sensor electrode 1140b. A signal analyzer 1778 may be operatively coupled to the receiver circuit 1776, according to an embodiment. The signal analyzer 1778 may be configured to analyze digital data produced by the receiver circuit 1776, determine whether a flame is present in or absent from the selected combustion location, and report at least a change of state of the flame via a digital interface 1780, according to an embodiment.

In one embodiment, the waveform generator 1764 includes a direct digital synthesizer (DDS). In one embodiment, the waveform generator 1764 is integrated into the signal analyzer 1778. In one embodiment, the waveform generator 1764 includes an oscillator. In one embodiment, the waveform generator 1764 is configured to output a sinusoidal waveform. Additionally and/or alternatively, the waveform generator 1764 is configured to output a chopped DC waveform. In another embodiment, the waveform generator 1764 is configured to output a waveform having a frequency between 1 kHz and 100 kHz. In another embodiment, the waveform generator 1764 is configured to output a waveform having a frequency between 1 kHz and 10 kHz. In another embodiment, the waveform generator 1764 is configured to output a waveform having a frequency of about 5 kHz. In one embodiment, the amplifier 1766 is configured to output an amplified waveform having a peak voltage greater than 10 volts. In another embodiment, the amplifier 266 is configured to output an amplified waveform having a peak voltage less than 120 volts. Additionally and/or alternatively, the amplifier 1766 is configured to output an amplified waveform having a peak voltage of about 40 volts. In an embodiment, the amplifier 1766 is configured to output an amplified waveform having 15 volt peak-to-peak.

In one embodiment, the electrical filters 1768, 1772 each include a vacuum bipolar electrode emitter operatively coupled to ground. In another embodiment, the electrical filters 1768, 1772 each include an antiparallel pair of Schottky diodes operatively coupled to ground.

Figure 18:
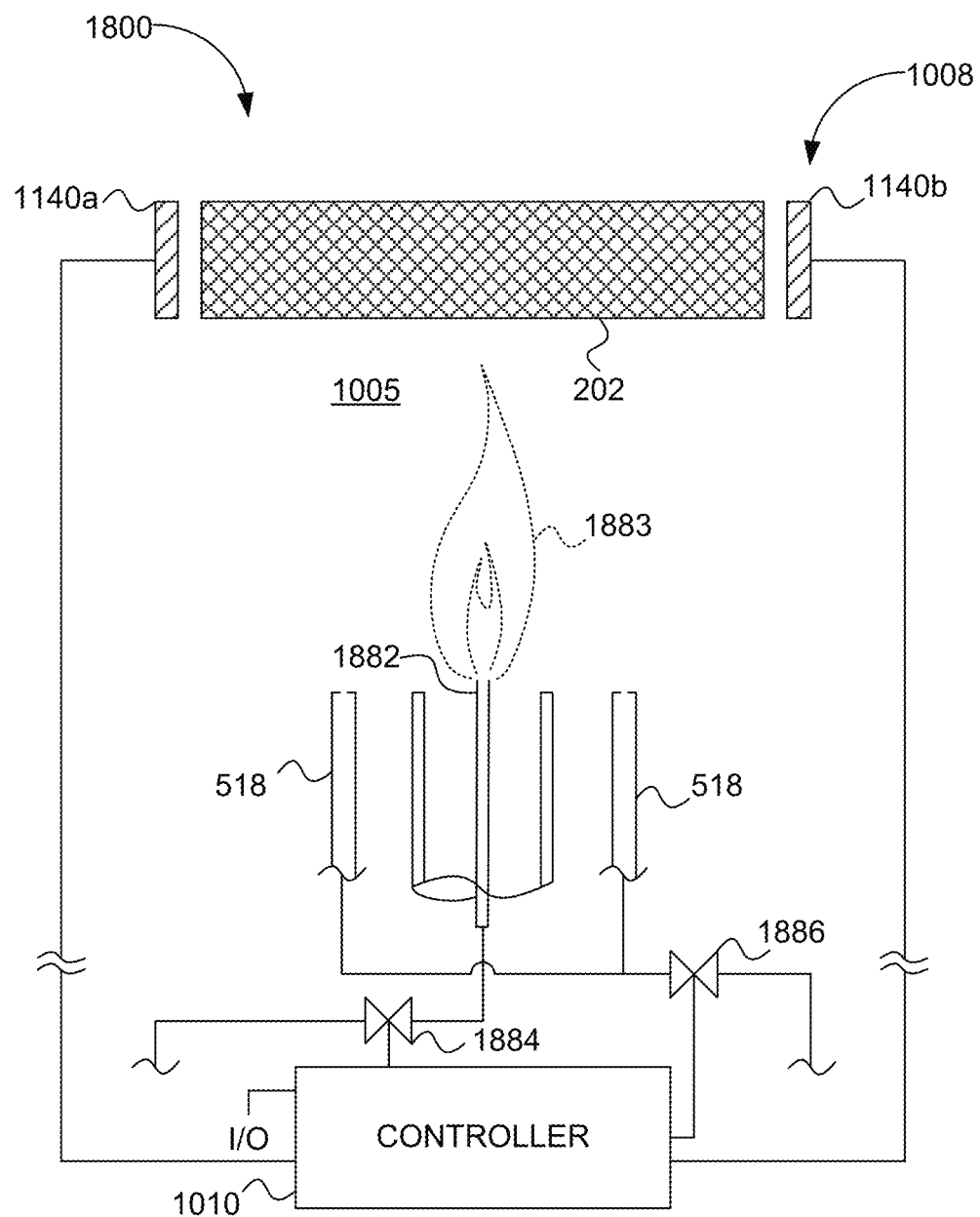
FIG. 18 is a diagram of a combustion system, according to an embodiment.

FIG. 18 is a diagram of a burner system 1800, according to an embodiment. The burner system 1800 includes a burner controller 1010 that may be operably coupled to the flame sensor 1008. A main fuel valve 1886 may be operably coupled to the burner controller 1010, and may be configured to control fuel flow to the main fuel source 518, according to an embodiment. The burner controller 1010 may be configured to actuate the main fuel valve 1886 to control the fuel flow to the main fuel source 518 responsive to data received from the flame sensor 1008, according to an embodiment. Additionally, or alternatively, the burner controller 1010 may be configured to actuate the main fuel valve 1886 to reduce or stop fuel flow responsive to receiving the data from the flame sensor 108 corresponding to an absence of a flame in the perforated flame holder 202. Additionally, or alternatively, a pilot fuel source 1882 may be configured to support a pilot flame 1883 capable of raising the temperature of the perforated flame holder 202 to the auto ignition temperature of the main fuel and oxidant mixture 1003, and a pilot fuel valve 1884 may be operably coupled to the burner controller 1010 and configured to control pilot fuel flow to the pilot fuel source 1882. The burner controller 1010 may be configured to actuate the pilot fuel valve 1884 to control the pilot fuel flow to the pilot fuel source 1882 responsive to data received from the flame sensor 1008, according to an embodiment. Additionally, or alternatively, the burner controller 1010 may be configured to actuate the pilot fuel valve 1884 to start or increase the pilot fuel flow responsive to receiving data from the flame sensor corresponding to an absence of a flame in the perforated flame holder 202. The first and the second sensor electrodes 1140a, 1140b may optionally include a superalloy, such as Hastelloy or Inconel, or may be formed from silicon carbide, for example.

Although not pictured, the combustion system 1800 may also include a plasma generator. The controller 1010 may control the plasma generator responsive to signals received from the combustion sensor to stabilize the combustion reaction.

In one embodiment, the controller 1010 may include multiple controllers configured to monitor and/or control aspects of the combustion system 1800.

In one embodiment, while FIG. 18 does not show a sensor controller, a sensor controller 1145 may also be present as shown in FIG. 11A. Alternatively, the sensor controller 1145 may be part of the controller 1010. Additionally, though a power source is not shown in FIG. 18, a power source may also be present.

Figure 19:
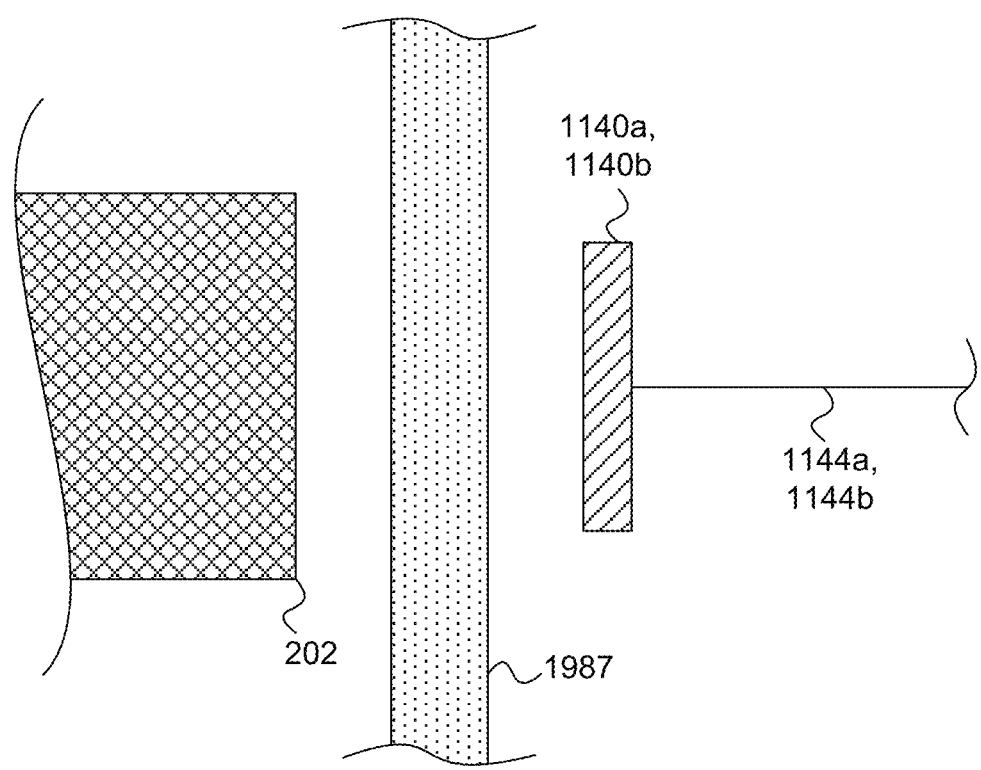
FIG. 19 is a diagram of an arrangement of a sensing electrode, according to an embodiment.

FIG. 19 is a diagram of an arrangement of a sensing electrode 1140a, 1140b, according to an embodiment. A dielectric wall 1987 may be formed from a ceramic material disposed between a flame holder 202 (which may include a perforated flame holder 202) and the first and/or the second sensor electrodes 1140a, 1140b and may be configured to shield the first and the second sensor electrodes 1140a, 1140b from high temperatures adjacent to the perforated flame holder 202. The dielectric wall 1987 may be formed from zirconium, for example. Additionally, or alternatively, the dielectric wall 1987 may be formed as a furnace wall defining a furnace volume 1005.

Figure 20:
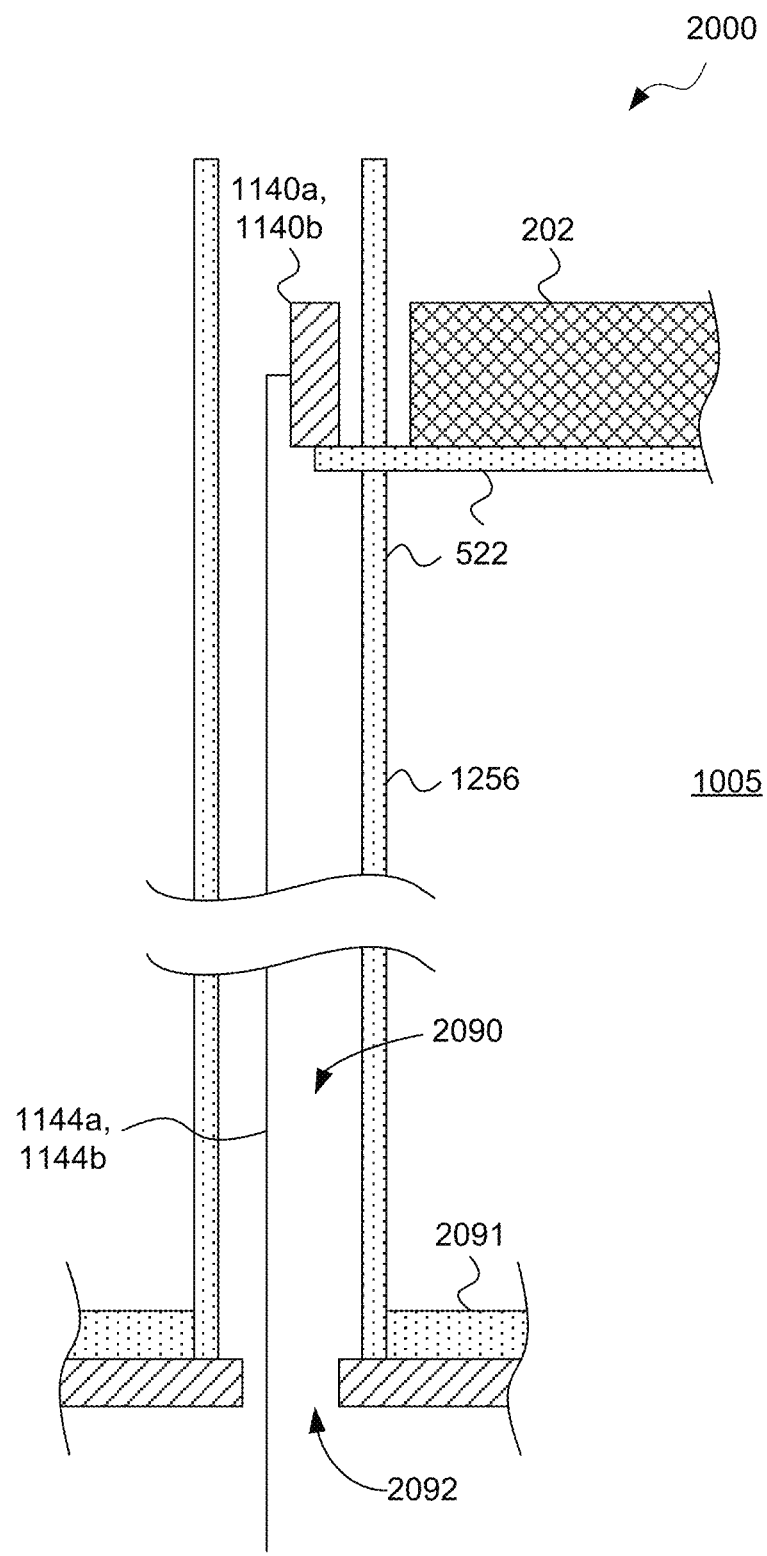
FIG. 20 is a diagram of a portion of a combustion system, according to an embodiment.

FIG. 20 is a diagram of a portion of a combustion system 2000, according to an embodiment. A perforated flame holder support structure 522 may be configured to support the perforated flame holder 202 away from the main fuel source (not shown) and the oxidant source (not shown), and the perforated flame holder support structure 522 may include a hollow support leg 1256, such as a ceramic tube defining a heat shielded volume 2090, according to an embodiment.

In one embodiment, the first and the second sensor electrical leads 1144a, 1144b may be inserted into a furnace volume 1005, in which the perforated flame holder 202 is disposed, through respective heat shielded volumes 2090. Additionally or alternatively, the first and the second sensor electrodes 1140a, 1140b may be disposed in corresponding heat shielded volumes 2090, as shown. Optionally, the ceramic tube 1256 may be supported by a furnace wall or floor 2091 and arranged to draw ambient air through an aperture 2092 whereby the temperature in the heat shielded volume 2090 may be reduced compared to the temperature of the furnace volume 1005.

In one embodiment, the first and the second sensor electrodes 1140a, 1140b may be resistively coupled through the perforated flame holder 202. The controller 1010 may be configured to compare an average level of the broadcast signal to a threshold. In an embodiment, the controller 1010 may be configured to output flame state data corresponding to flame presence when the average level of the received signal is greater than the threshold. In another embodiment, the controller 1010 may be configured to output flame state data corresponding to flame absence when the average level of the received signal is less than the threshold. The controller 1010 can control a plasma generator to stabilize the combustion reaction 1004 responsive to the sensor signals from the first and the second sensor electrodes 1140a, 1140b.

Figure 21:
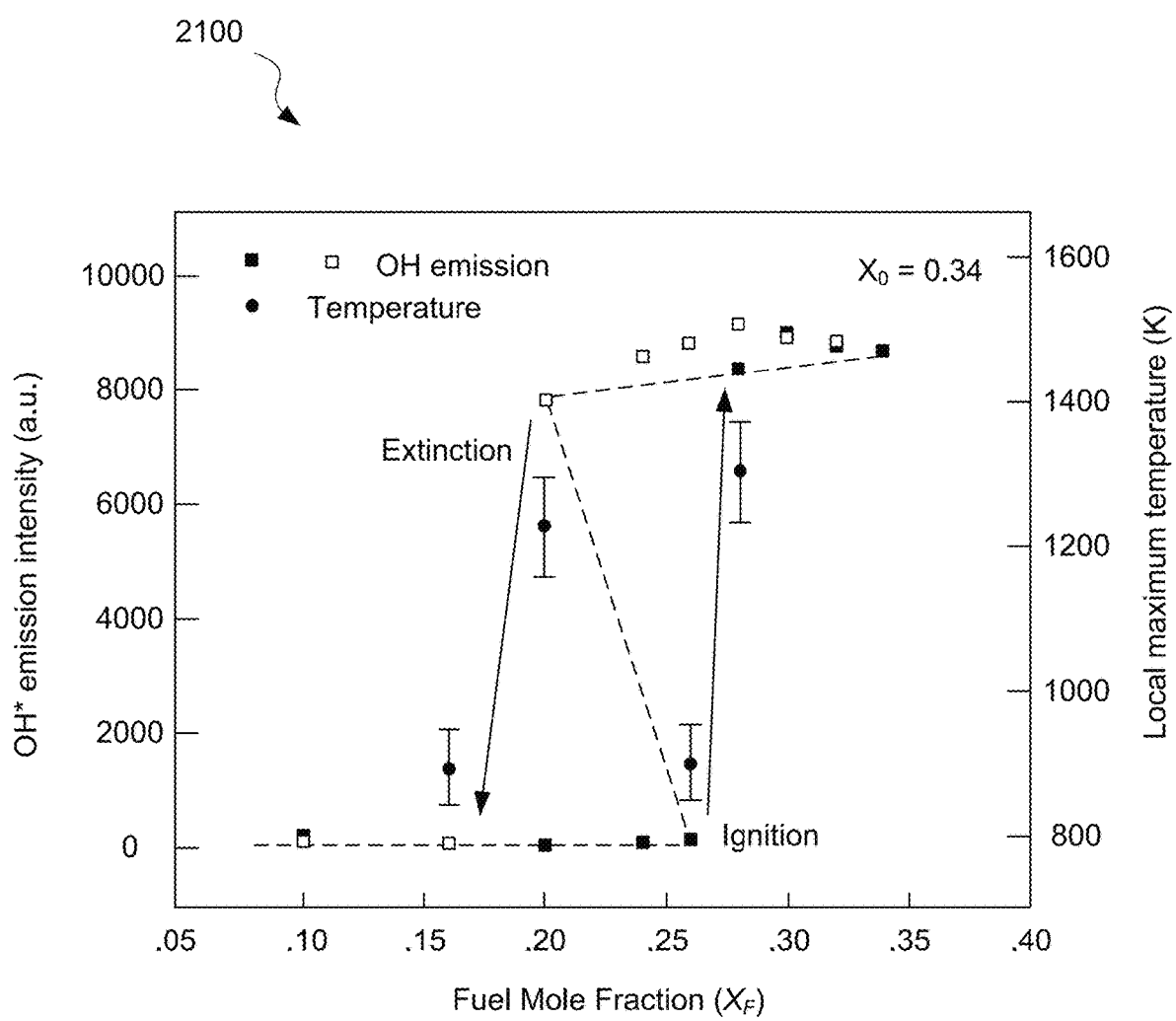
FIGS. 21 and 22 include graphs that illustrate relationships between OH* emission intensity, local maximum temperature and methane mole fraction for an excitation frequency of 24 kHz and oxygen fractions of $X_O$=0.34 and $X_O$=0.62 (solid square symbols: increasing $X_F$, open square symbols: decreasing $X_F$), according to various embodiments.
Figure 22:
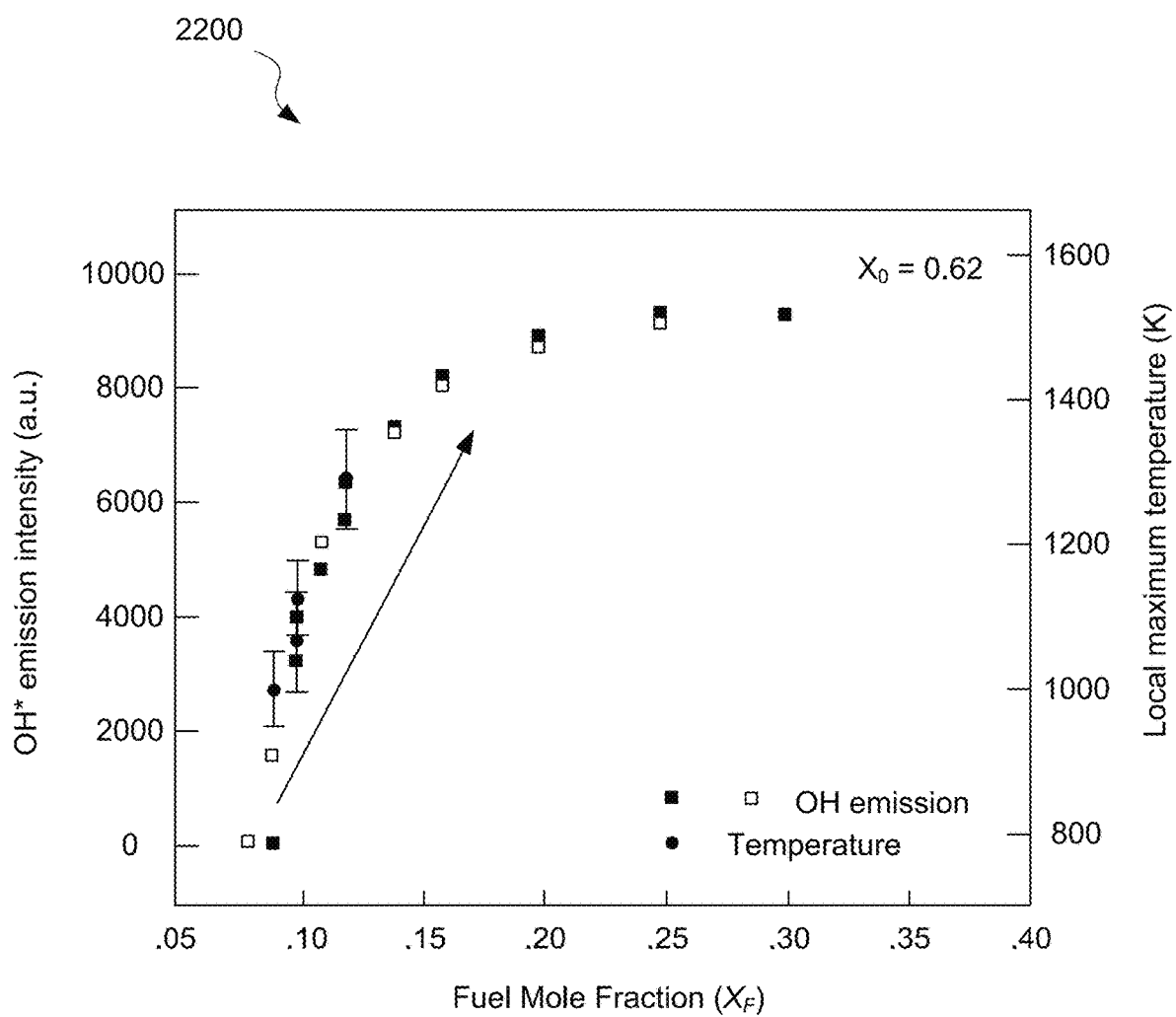

FIGS. 21 and 22 include graphs 2100, 2200 that illustrate relationships between OH* emission intensity, local maximum temperature and methane mole fraction for an excitation frequency of 24 kHz and oxygen fractions of $X_O$=0.34 and $X_O$=0.62 (solid square symbols: increasing XE, open square symbols: decreasing XE), according to various embodiments. The flame stabilization effect of low temperature plasma using in situ nanosecond pulsing was demonstrated for the case of a counter-flow methane/oxygen diffusion flame. The OH* dependence, which may be an indication of flame temperature, on the fuel mole fraction is shown in FIGS. 21 and 22. FIG. 21 shows that with a low oxygen mole fraction ($X_O$=0.34) in the oxidizer stream a clear ignition and extinction limit exist. However, when the oxygen mole fraction was increased to $X_O$=0.62 shown in FIG. 22, the ignition limit was reduced eliminating the classical combustion S-curve. Instead, a monotonic smooth ignition to flame transition curve may be observed. In this new plasma assisted flame stabilization regime, the flame does not have an extinction limit. Flame stabilization may be governed by plasma enhanced ignition via rapid low temperature plasma radical production by reactions such as $e+O_2 \rightarrow e+O+O(1D)$, which creates a new reaction pathway for the chain-branching process in combustion.

Arguably the most important parameter to consider in the instant system may be the electric field divided by the density, E/n, commonly referred to as the reduced electric field. The reduced electric field may be directly correlated to the electron temperature and may be a key parameter in determining the reactive species that may be produced by the plasma.

Figure 23:
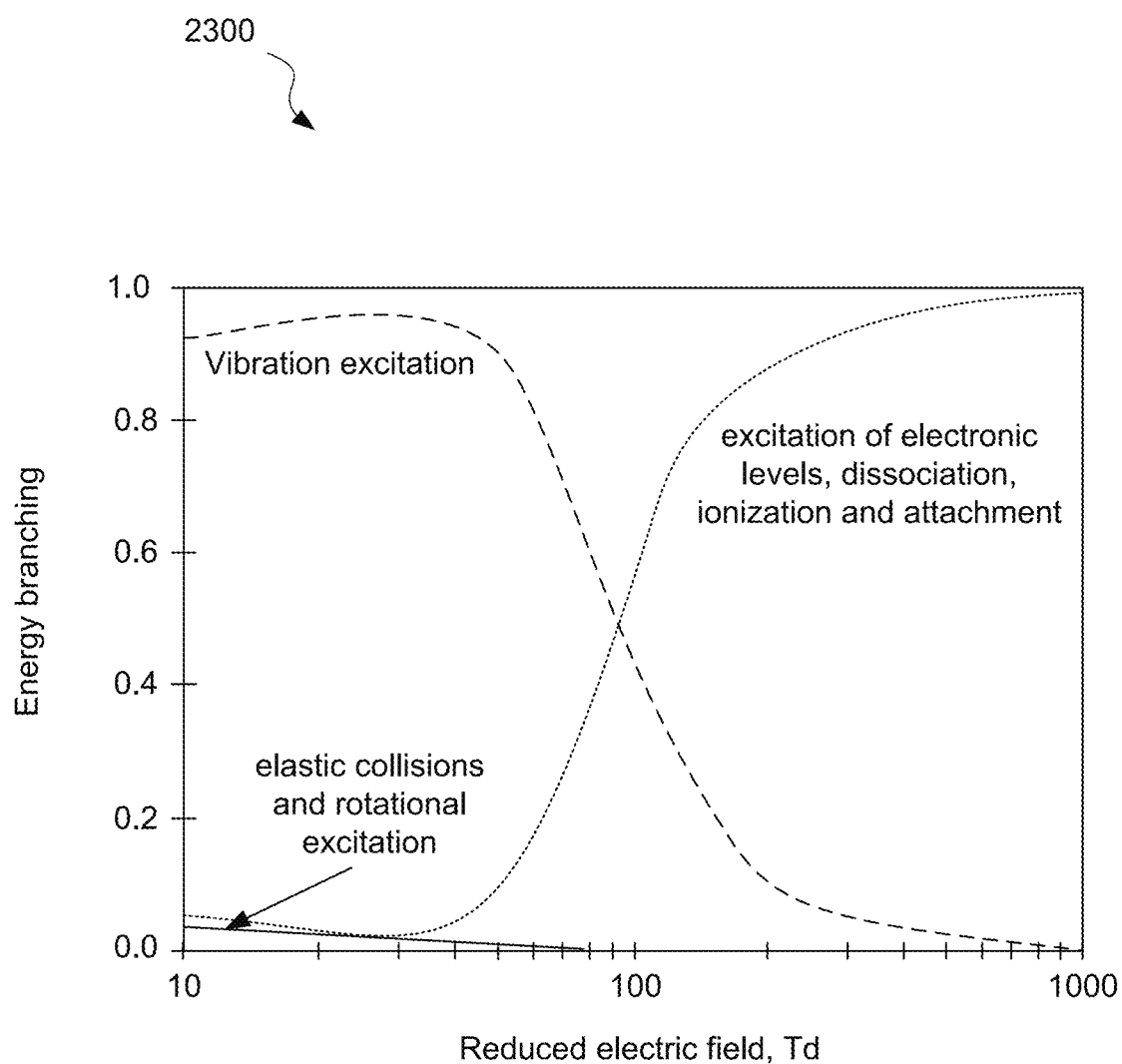
FIG. 23 includes a graph showing the effect of an electric field function, reduced electric field, on reactive species produced, according to an embodiment.

FIG. 23 includes a graph 2300 showing the effect a function of electric field strength, reduced electric field, on the reactive species produced, according to an embodiment.

Figure 24:
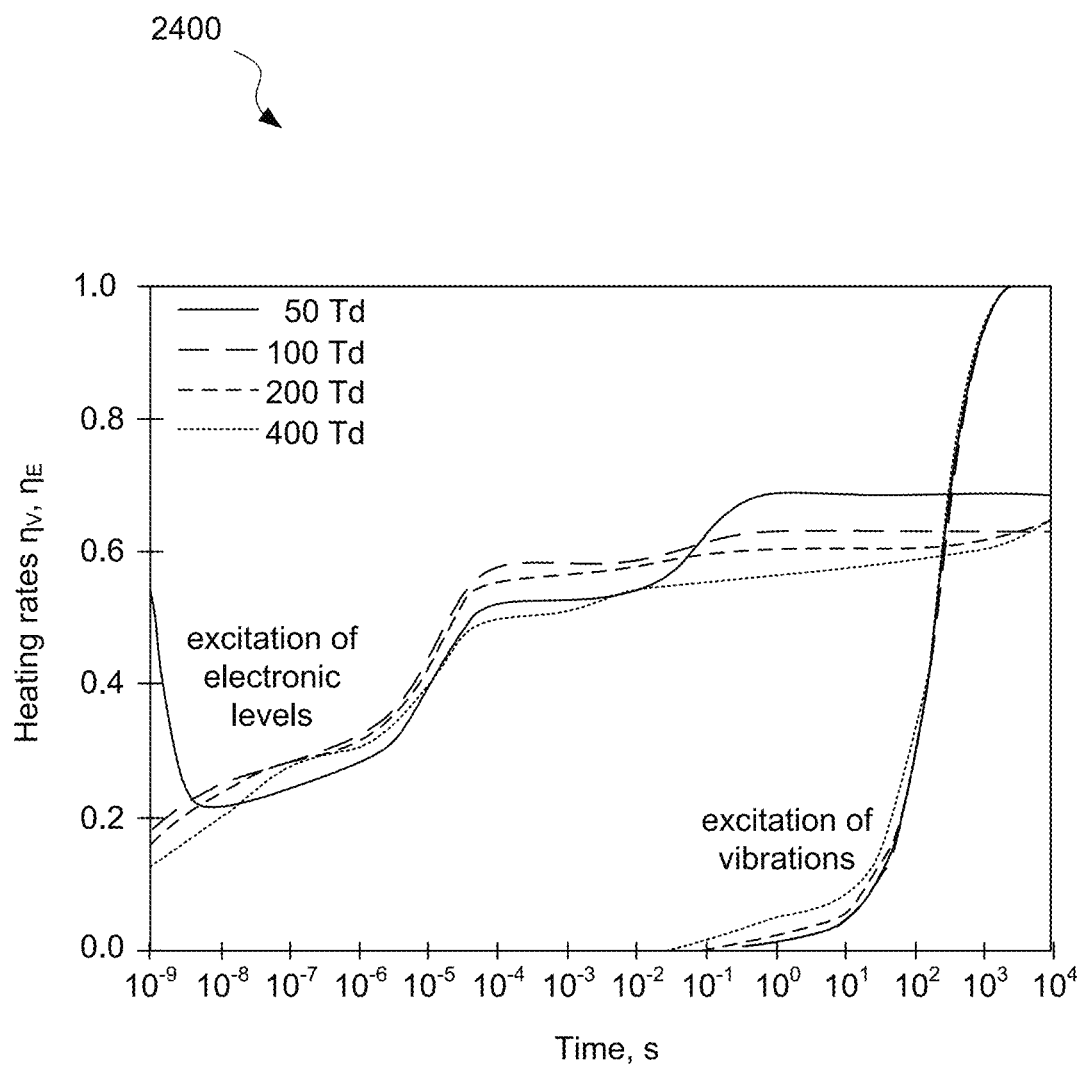
FIG. 24 includes a graph showing the effect of time on reactive species produced, according to an embodiment.

FIG. 24 includes a graph 2400 showing the effect of time on reactive species produced, according to an embodiment.

Figure 25:
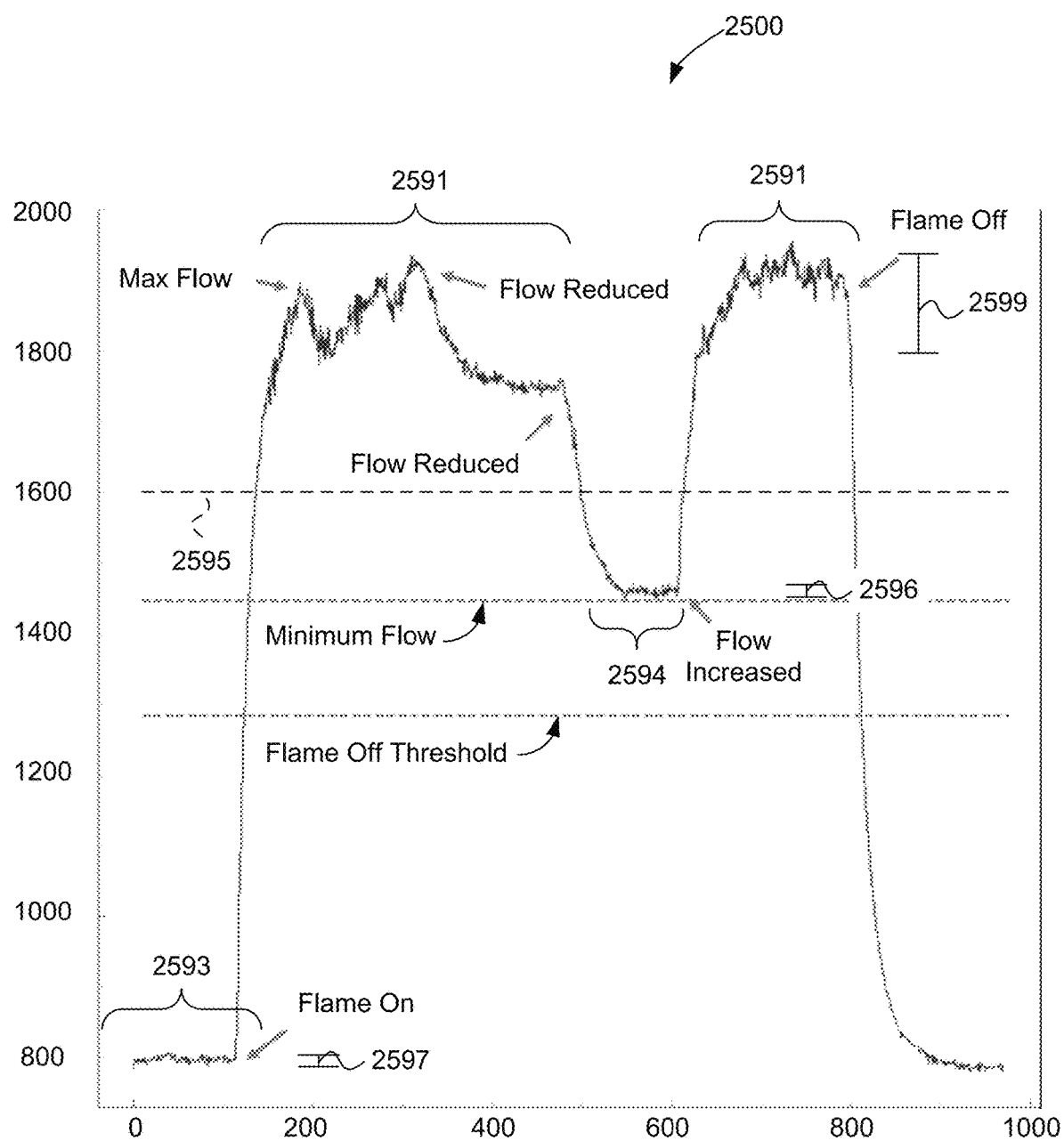
FIG. 25 is a plot of a signal received under conditions of flame presence and flame absence, according to an embodiment.

FIG. 25 is a plot 2500 of a signal that was received (during an experimental run) under conditions of flame presence and flame absence, according to an embodiment. The plot 2500 shows received voltage as a function of time, time being shown along the horizontal axis. According to an embodiment, the first and the second sensor electrodes may be capacitively coupled through the perforated flame holder. The controller may be programmed to recognize flame presence when the received waveform 2500 has a value 2594 less than a threshold 2595 and to recognize flame absence when the received waveform 2500 has a value 2593 greater than the threshold 2595. Additionally or alternatively, the controller may be programmed to recognize flame presence 2594 when the received waveform 2500 has a noise amplitude equal to or greater than a noise threshold 2596 larger than a noise threshold 2597 corresponding to flame absence 2593, and to recognize flame absence 2593 when the received waveform 2500 has a noise amplitude less than the noise threshold 2596. The inventors noted that higher fuel and oxidant flow rates (e.g., shown during periods 2591) exhibit a larger noise value 2599 compared to a lower noise value 2596 during a period 2594 corresponding to a lower fuel and oxidant flow rate.

Figure 26:
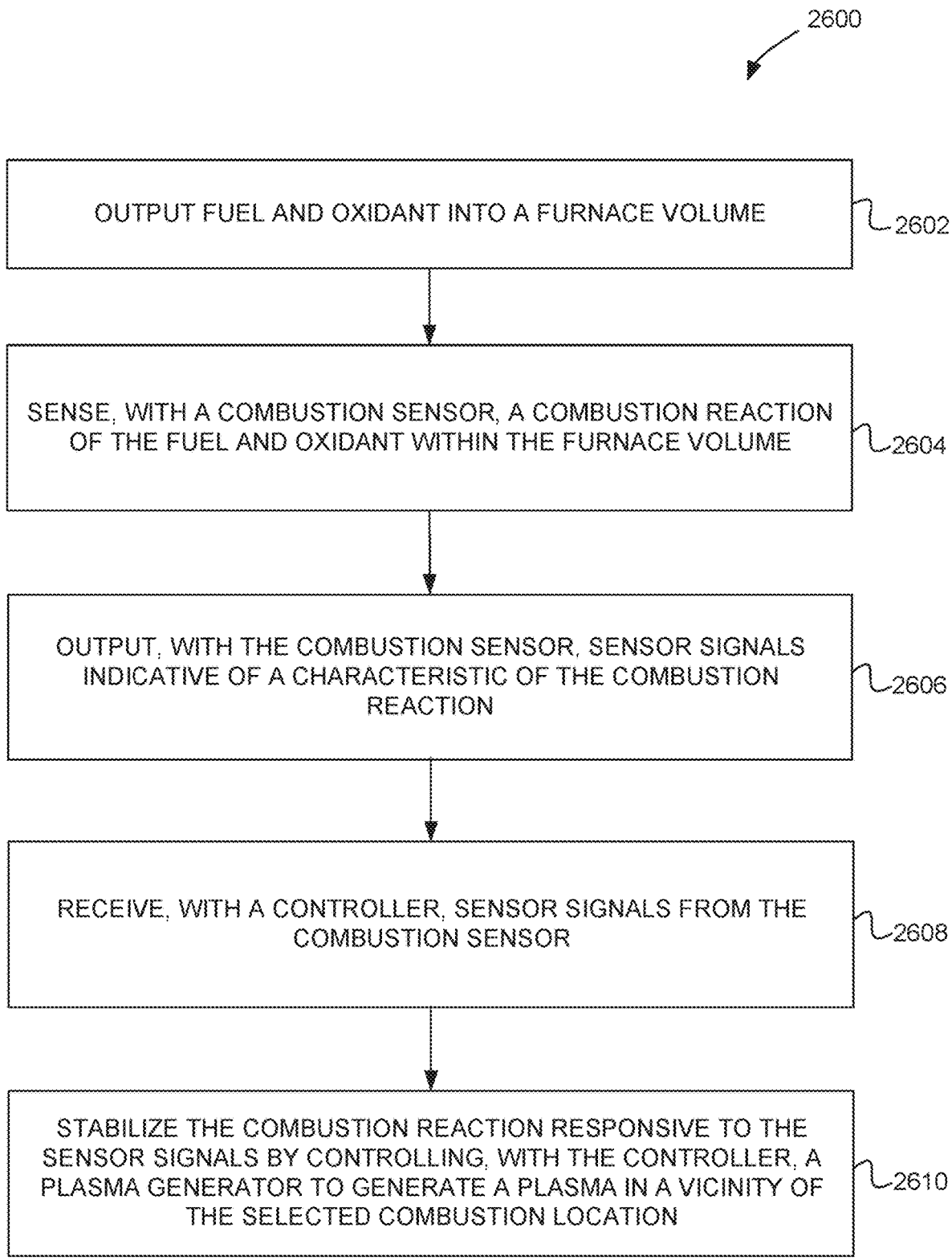
FIG. 26 is a flow chart showing a method, according to an embodiment.

FIG. 26 is a flow chart showing a method 2600, according to an embodiment. The method 2600 includes, in step 2602, outputting fuel and oxidant into a furnace volume. Step 2604 includes sensing, with a combustion sensor, a combustion reaction of the fuel and oxidant within the furnace volume. Step 2606 includes outputting, with the combustion sensor, sensor signals indicative of a characteristic of the combustion reaction. Step 2608 includes receiving, with a controller, sensor signals from the combustion sensor. Step 2610 includes stabilizing the combustion reaction responsive to the sensor signals by controlling, with the controller, a plasma generator to generate a plasma in a vicinity of the selected combustion location.

In one embodiment, the controller causes the plasma generator to generate the plasma responsive to the sensor signals indicating that the combustion reaction is unstable.

According to an embodiment, the method 2600 further includes refraining from causing the plasma generator to generate the plasma when the sensor signals indicate that the combustion reaction is stable.

According to an embodiment, the plasma is a low temperature plasma. In one embodiment, the low temperature plasma includes oxygen radicals. In another embodiment, the low temperature plasma has insufficient energy to ignite the combustion reaction when the combustion reaction is absent. Additionally and/or alternatively, the plasma has sufficient energy to ignite the combustion reaction. In an embodiment, the plasma is a hot plasma including a gas including ions and charged particles.

According to an embodiment, the method 2600 includes holding the combustion reaction with a flame holder positioned within the furnace volume, wherein the selected combustion location is within or adjacent to the flame holder.

According to an embodiment, the method 2600 includes imparting a swirling motion to the fuel and the oxidant with a swirler.

According to an embodiment, the plasma is a high temperature plasma. In an embodiment, the high temperature plasma is configured to ignite the fuel and the oxidant.

According to an embodiment, the power source is a pulsed power source. In an embodiment, the pulsed power source is operable to output nanosecond electrical pulses having a duration of between 100 picoseconds and 300 nanoseconds. In another embodiment, the pulsed power source is operable to output at least 10 kilovolt nanosecond electrical pulses. Additionally and/or alternatively, the pulsed power source is operable to output about 30 kilovolt nanosecond electrical pulses. In another embodiment, the pulsed power source is operable to output nanosecond electrical pulses at a duty cycle of between 1% and 50%. In another embodiment, the pulsed power source is operable to output pulses at a rate of 10 kilohertz to 100 kilohertz.

According to an embodiment, the power source includes a signal generator configured to drive a nanosecond pulse waveform operatively coupled to a voltage amplifier. In an embodiment, the voltage amplifier is operatively coupled to the first and the second plasma generation electrodes and configured to drive a permittivity-coupled signal therebetween. In another embodiment, the voltage amplifier includes a pair or more of inversely coupled voltage multipliers, the voltage multipliers being clocked at a frequency corresponding to the nanosecond pulse. Additionally or alternatively, the voltage amplifier includes a plural stage amplifier circuit configure to output the nanosecond pulse waveform. In one embodiment, the voltage amplifier is coupled to the first and the second electrodes to drive the first and the second electrodes as a synchronous push-pull driver.

According to an embodiment, the voltage amplifier is coupled to a common ground coupled through a sensor node with the second electrode and coupled to drive the first electrode.

According to an embodiment, the low temperature plasma is operable to stabilize a flame held by the perforated flame holder.

According to an embodiment, the flame holder support structure includes a ceramic material and includes at least two hollow legs. In one embodiment, the first and the second output terminals of the pulsed power source are respectively coupled to the first and the second plasma generation electrodes by first and second conductive electrical leads. The first and the second conductive electrical leads may be respectively routed from the power source to the first and the second plasma generation electrodes through the hollow legs.

Figure 27:
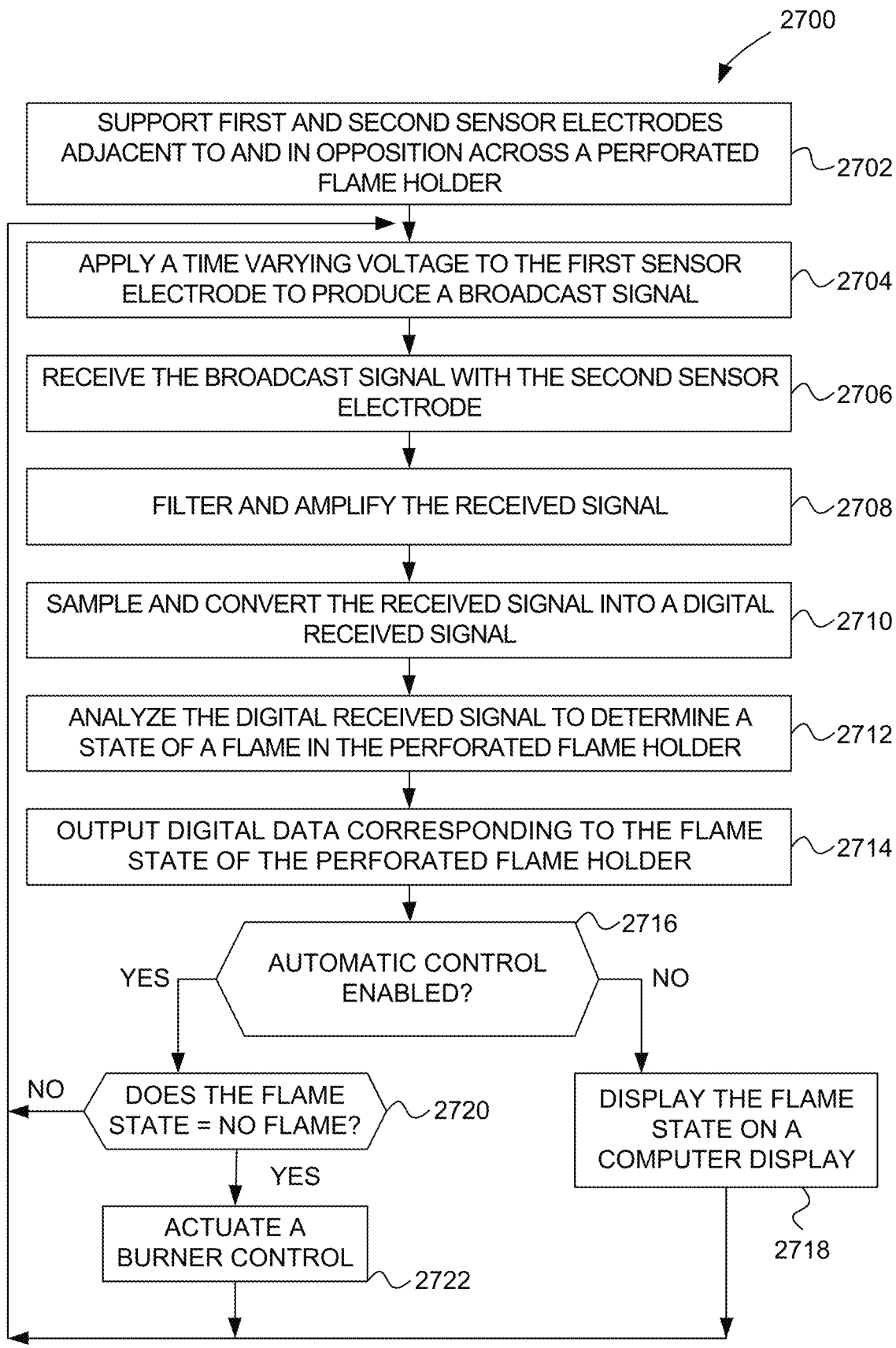
FIG. 27 is a flow chart showing a method for sensing the presence or absence of a flame in a perforated flame holder, according to an embodiment.

FIG. 27 is a flow chart showing a method 2700 for sensing the presence or absence of a flame in a perforated flame holder, according to an embodiment.

According to an embodiment, step 2702 includes supporting first and second sensor electrodes adjacent to a perforated flame holder, according to an embodiment.

Step 2704 includes applying a time varying voltage to the first sensor electrode to produce a broadcast signal that propagates through the perforated flame holder, according to an embodiment.

Step 2706 includes receiving the broadcast signal, modified according to the presence or absence of a flame in the perforated flame holder, with the second sensor electrode, according to an embodiment.

Step 2710 includes converting the received signal into a digital received signal, according to an embodiment.

Step 2712 includes analyzing the digital received signal with a signal analyzer to determine a state of a flame in the perforated flame holder, according to an embodiment.

Step 2714 includes outputting digital data corresponding to the state, according to an embodiment.

According to an embodiment, the term "state" means "presence" or "absence" of the flame.

According to an embodiment, supporting the first and second sensor electrodes in step 2702 may include supporting heat resistant electrodes. Additionally, or alternatively, it may include supporting superalloy electrodes, such as Inconel or Hastelloy superalloys. Additionally, or alternatively, supporting heat resistant electrodes may also include supporting silicon carbide electrodes. According to an embodiment, supporting the first and second sensor electrodes in step 2702 may include providing one or more heat resistant dielectric walls between the perforated flame holder and the sensor electrodes. Additionally, or alternatively, providing one or more heat resistant walls may include supporting the sensor electrodes in respective air-cooled volumes defined by perforated flame holder support structures. According to an embodiment, applying a time varying voltage to the first sensor electrode may include generating a sinusoidal constant frequency waveform corresponding to the time varying voltage. According to an embodiment, applying a time varying voltage may include generating a constant frequency square waveform or a constant frequency triangular wave corresponding to the time varying voltage.

According to an embodiment, applying a time varying voltage to the first sensor electrode in step 2704 may include amplifying the time varying voltage from a logic level to a broadcast level higher than the logic level. Amplifying the time varying voltage may include amplifying to greater than 10 volts peak voltage. Amplifying the time varying voltage may include amplifying to between 10 volts and 1000 volts peak voltage. Amplifying the time varying voltage may include amplifying to between 10 volts and 240 volts peak voltage. Amplifying the time varying voltage may include amplifying to between 10 volts and 120 volts peak voltage. In another embodiment, amplifying the time varying voltage may include amplifying to between 20 volts and 80 volts peak voltage. Amplifying the time varying voltage may include amplifying to between 40 volts peak voltage, plus or minus 4 volts.

Step 2708 may include filtering the received signal, and amplifying the received signal such as to a range compatible with a sampling capacitor, according to an embodiment.

At step 2710, converting the received signal to the digital received signal may include sampling the received signal with a sampling capacitor, and performing an analog-to-digital conversion with an analog-to-digital converter, according to an embodiment. Additionally, or alternatively, converting the received signal to a digital received signal may include sampling at twice or more times a constant frequency time varying voltage (to satisfy a Nyquist criterion). According to an embodiment, converting the received signal to a digital received signal may include receiving the received frequency according to a homodyne receiver architecture. Converting the received signal to a digital received signal may include receiving a time gate from a waveform generator that creates a waveform corresponding to the time varying voltage and triggering the sampling capacitor according to the received time gate. Converting the received signal to a digital received signal may include receiving the received signal according to a heterodyne receiving architecture.

At step 2712, analyzing the digital received signal may include determining an average level, comparing the average voltage level to a threshold voltage level, and determining a flame may be absent when the average voltage level may be higher than the threshold level, according to an embodiment.

At step 2712, analyzing the digital received signal may include determining an average voltage level, comparing the average voltage level to a threshold voltage level, and determining that a flame is present when the average voltage level is lower than the threshold voltage level, according to an embodiment.

At step 2712, analyzing the digital received signal may include determining an average noise amplitude, comparing the average noise amplitude to a threshold noise amplitude, and determining that a flame is absent when the average noise amplitude is less than the threshold noise amplitude.

At step 2712, analyzing the digital received signal may include determining an average noise amplitude, comparing the average noise amplitude to a threshold noise amplitude, and determining that a flame is present when the average noise amplitude is greater than the threshold noise amplitude.

Step 2716 is shown as a decision stem; however, both "alternative" processes may optionally be executed. If automatic control is not enabled, or in addition to the process that is executed when automatic control may be enabled, the method 2700 proceeds to step 2718. If automatic burner control is enabled, the method 2700 proceeds from step 2716 to step 2720. Steps 2704, 2706, optional step 2708, 2708, 2712, 2714, 2716, 2720, and optional step 2718 may be repeated. The method 2700 can proceed from step 2702 to step 2722.

According to an embodiment, step 2718 may include displaying information corresponding to the digital data corresponding to the flame state on a computer display. Optionally, displaying information on a computer display may include displaying a plot similar to the plot 2500 shown in FIG. 25.

According to an embodiment, at step 2712, determining the data corresponding to the flame state may indicate that a flame is present. The method 2700 may loop back to step 2704 of applying the time varying voltage to the first sensor electrode and the remaining steps. According to an embodiment, steps 2704, 2706, optional step 2708, 2710, 2712, 2714, 2716, 2720, and optional step 2718 are repeated.

Proceeding from step 2720 to step 2722, if the flame state indicates that the flame is absent, the method 2700 may include actuating a burner control to stabilize the flame or put the burner in a safe state, according to an embodiment. Additionally, or alternatively, actuating a burner control may include actuating a main fuel valve to reduce main fuel flow. Additionally, or alternatively, actuating a burner control may include actuating a main fuel valve to increase main fuel flow.

According to an embodiment, actuating a burner control may include actuating a main fuel valve to stop main fuel flow. Alternatively, actuating a burner control may also include activating a perforated flame holder heater.

According to an embodiment, the first and the second electrodes are positioned in opposition around the perforated flame holder.

Figure 28:
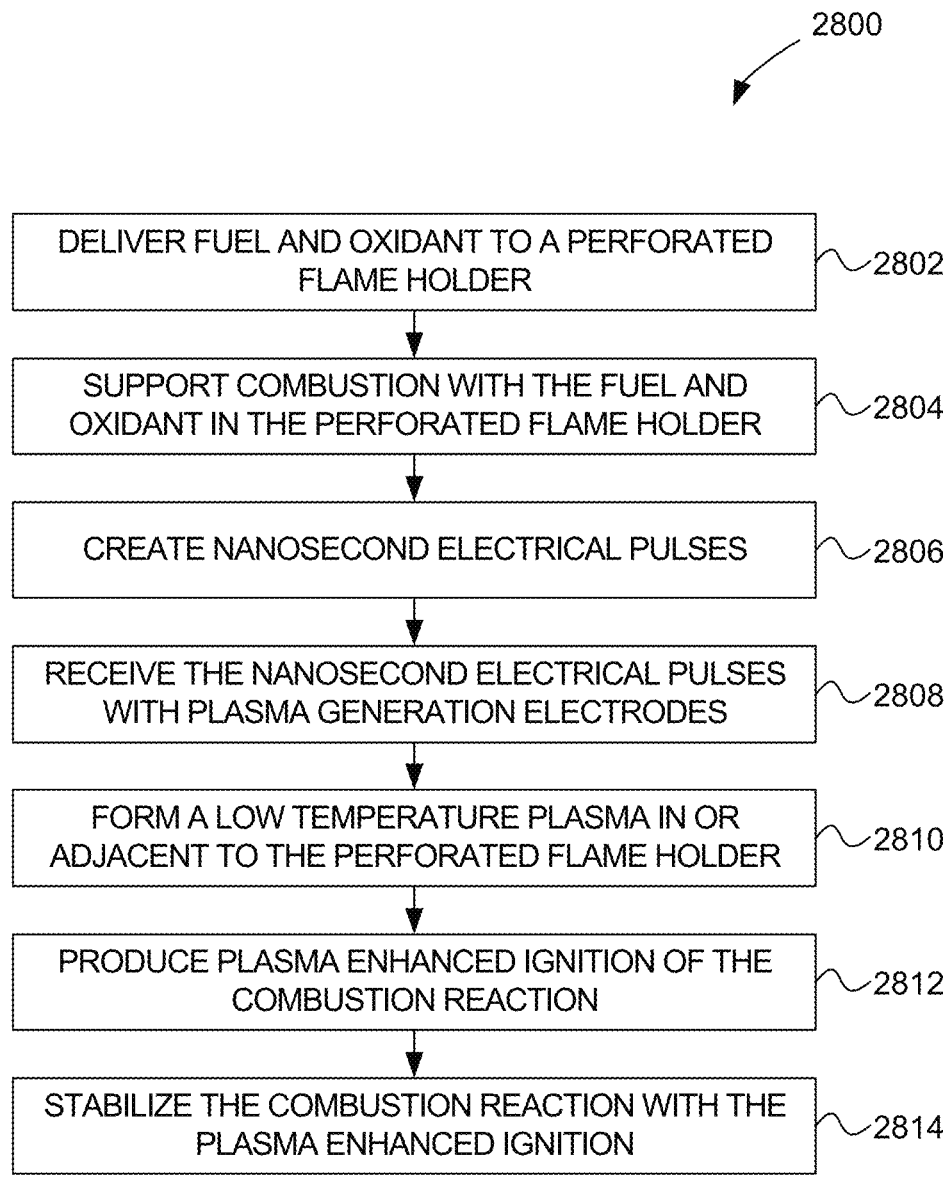
FIG. 28 is a flow chart showing a method for improving flame stability in a burner, according to an embodiment.

FIG. 28 is a flow chart showing a method 2800 for improving flame stability in a burner, according to an embodiment. Step 2802 may include delivering a fuel and oxidant mixture to a perforated flame holder. Step 2804 includes supporting a combustion reaction with the fuel and oxidant mixture in the perforated flame holder. Step 2810 includes forming a low temperature plasma in or adjacent to the perforated flame. Step 2812 includes producing plasma enhanced ignition of the combustion reaction.

According to an embodiment, step 2806 may include creating nanosecond electrical pulses. Step 2808 may include receiving the nanosecond pulses with plasma generation electrodes disposed within or adjacent to the perforated flame holder. According to an embodiment, step 2814 may include stabilizing the combustion reaction with the plasma enhanced ignition.

According to an embodiment, the plasma may be a low temperature plasma. In an embodiment, the low temperature plasma may be configured to stabilize the combustion reaction. According to an embodiment, forming the low temperature plasma may include converting an oxygen molecule to oxygen radicals. Additionally or alternatively, forming the low temperature plasma may include ejecting an electron from a dielectric barrier layer on a surface of at least one of the plasma generation electrodes. Additionally or alternatively, forming the low temperature plasma may include ejecting an electron from at least one of the plasma generation electrodes formed as a corona electrode. According to an embodiment, the plasma may be a high temperature plasma. In an embodiment, the high temperature plasma may be configured to ignite the combustion reaction.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A burner, comprising:
    a fuel source;
    an oxidant source;
    a plenum wall defining an air plenum, the air plenum configured to receive fuel and oxidant respectively from the fuel source and the oxidant source, the air plenum further configured to convey the fuel and oxidant to facilitate mixture of the fuel and oxidant into a fuel-oxidant mixture;
    an ignition source disposed at a distal portion of the air plenum and oriented to ignite the fuel-oxidant mixture to produce a flame in a flame region;
    at least a first electrode and a second electrode arranged adjacent to the flame region and configured to produce a time-varying electromagnetic field across the flame region substantially transverse to a flow direction of the fuel and oxidant; and
    a control circuit configured to generate an excitation signal and provide the excitation signal to the first electrode;
    wherein a change in electrical permittivity or electrical capacitance in the flame region is determined from the time-varying electromagnetic field,
    wherein at least the first electrode and the second electrode are disposed opposite each other across the flame region, the first electrode configured to broadcast the excitation signal to produce the time-varying electromagnetic field between the first and second electrodes, the second electrode being configured to receive a detection signal, the detection signal including the broadcast excitation signal as affected by the change in electrical permittivity between the first and second electrodes,
    wherein the control circuit is further configured to receive the detection signal from the second electrode and to determine a magnitude of the electrical permittivity of the flame region by measuring or calculating a signal characteristic from the detection signal,
    wherein the control circuit is further configured to identify a flame characteristic by comparing the determined magnitude of the electrical permittivity against an index of flame characteristics corresponding to respective electrical permittivity magnitudes,
    wherein the control circuit is further configured to drive the ignition source responsive to the identified flame characteristic, and
    wherein the identified flame characteristic is a presence or absence of the flame as determined by comparison of the magnitude of the electrical permittivity with a threshold electrical permittivity, and the control circuit drives the ignition source when the flame is indicated to be absent.

2. The burner according to claim 1, wherein the burner is a pilot burner.

3. The burner according to claim 1, wherein the control circuit is further configured to alter a supply rate of the fuel supplied by the fuel source based on the identified flame characteristic.

4. The burner according to claim 3, wherein the identified flame characteristic is a presence or absence of the flame as determined by comparison of the magnitude of the electrical permittivity with a threshold electrical permittivity, and the control circuit terminates the supply of fuel when the flame is indicated to be absent.

5. The burner according to claim 1, wherein the control circuit is further configured to compare the detection signal to a threshold detection signal, and to produce a binary result signal indicating presence or absence of the flame.

6. The burner according to claim 1, wherein the control circuit is configured to produce an output signal indicating a strength of the flame between the first and the second electrodes.

7. The burner according to claim 1, wherein the output signal is an analog signal.

8. The burner according to claim 7, wherein the analog signal corresponds to a strength of combustion activity between the first and the second electrodes.

9. The burner according to claim 8, wherein the output signal has a strength between 4 mA and 20 mA.

10. The burner according to claim 1, wherein the excitation signal is generated periodically.

11. The burner according to claim 1, wherein the control circuit includes an excitation signal source configured to control at least one or more of: wave shape, magnitude, and frequency of the excitation signal.

12. The burner according to claim 11, wherein the generated excitation signal is a square wave, and the excitation signal source is further configured to control at least one or more of: pulse width, duty cycle, and modulation.

13. The burner according to claim 11, wherein the generated excitation signal is sinusoidal and is generated by direct digital synthesis.

14. The burner according to claim 1, wherein the control circuit includes an amplifier configured to amplify the generated excitation signal provided to the first electrode.

15. The burner according to claim 1, wherein the first and second electrodes are patch electrodes.

16. The burner according to claim 1, further comprising:
a first conductor in electrical continuity between the first electrode and the control circuit, and at least partly disposed peripherally to the plenum defining the air plenum; and
a second conductor in electrical continuity between the second electrode and the control circuit, and at least partly disposed peripherally to the plenum defining the air plenum.

17. The burner according to claim 1, wherein the first or second electrode is in electrical continuity with a conductive tubular structure disposed axially within the air plenum.

18. The burner according to claim 1, wherein the first or second electrode is in electrical continuity with a conductive tubular structure disposed peripherally to the air plenum.

19. A method, comprising:
receiving, in an air plenum, a fuel and an oxidant;
forming a fuel-oxidant mixture by conveying the fuel and the oxidant in the air plenum;
producing a flame in a flame region by igniting the fuel-oxidant mixture with an ignition source disposed at an extent of the plenum;
producing a time-varying electromagnetic field across the flame region with a first and a second electrode arranged adjacent to the flame region, the first electrode broadcasting an excitation signal to produce the time-varying electromagnetic field between the first and second electrodes, the second electrode receiving a detection signal, the detection signal including the broadcast excitation signal as affected by the change in electrical permittivity between the first and second electrodes;
determining a change in electrical permittivity in the flame region based on the time-varying electromagnetic field;
controlling the flame based on the change in electrical permittivity,
determining a magnitude of the electrical permittivity of the flame region by measuring or calculating a signal characteristic from the detection signal,
identifying a flame characteristic by comparing the determined magnitude of the electrical permittivity against an index of flame characteristics corresponding to respective electrical permittivity magnitudes,
wherein the identified flame characteristic is a presence or absence of the flame as determined by comparison of the magnitude of the electrical permittivity with a threshold electrical permittivity, and the control circuit drives the ignition source when the flame is indicated to be absent.

* * * * *